US009022916B2

(12) United States Patent
Farnan et al.

(10) Patent No.: US 9,022,916 B2
(45) Date of Patent: *May 5, 2015

(54) TRANSSEPTAL CANNULA, TIP, DELIVERY SYSTEM, AND METHOD

(71) Applicant: Circulite, Inc., Teaneck, NJ (US)

(72) Inventors: Robert C. Farnan, Fort Lauderdale, FL (US); Scott A. Olson, Zimmerman, MN (US); Elizabeth Jung, Zimmerman, MN (US); Andrew J. Dusbabek, Dayton, MN (US); Robert G. Hudgins, Monticello, MN (US)

(73) Assignee: Circulite, Inc., Teaneck, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/319,549

(22) Filed: Jun. 30, 2014

(65) Prior Publication Data

US 2014/0336445 A1  Nov. 13, 2014

Related U.S. Application Data

(60) Continuation of application No. 13/788,863, filed on Mar. 7, 2013, now Pat. No. 8,821,366, which is a continuation-in-part of application No. 13/088,620, filed on Apr. 18, 2011, now Pat. No. 8,394,010, which (Continued)

(51) Int. Cl.
*A61N 1/362* (2006.01)
*A61F 2/00* (2006.01)
(Continued)

(52) U.S. Cl.
CPC .............. *A61M 1/10* (2013.01); *A61M 1/3653* (2013.01); *A61M 1/3666* (2013.01); *A61M 25/04* (2013.01);
(Continued)

(58) Field of Classification Search
USPC ........................ 600/16, 17; 607/101, 115, 130
See application file for complete search history.

(56) References Cited

U.S. PATENT DOCUMENTS

| 6,530,876 B1 * | 3/2003 | Spence ........................... 600/16 |
| 2004/0024435 A1 * | 2/2004 | Leckrone et al. ............. 607/101 |

(Continued)

FOREIGN PATENT DOCUMENTS

| JP | 2005530593 A | 10/2005 |
| JP | 2006500090 A | 1/2006 |

(Continued)

OTHER PUBLICATIONS

European Patent Office, International Search Report and Written Opinion in PCT Application Serial No. PCT/US2014/020474, Sep. 8, 2014.

(Continued)

*Primary Examiner* — Nicole F Lavert
(74) *Attorney, Agent, or Firm* — Wood, Herron & Evans, L.L.P.

(57) ABSTRACT

A cannula assembly, further comprising a cannula body for directing blood from the heart of a patient, having distal and proximal ends and a lumen therebetween. A tip coupled to the distal end of the body, the tip having an opening. A pump for drawing blood into the cannula assembly and dispensing the blood from the cannula assembly and into the patient circulatory system. The lumen of the cannula body further comprises a first inner diameter at the proximal end and a second inner diameter at the distal end, the first inner diameter being larger than the second inner diameter. A tapered portion defined as a decrease in inner diameter from the first inner diameter to the second inner diameter between the proximal and distal ends, the tapered portion configured to prevent cavitation of the blood within the cannula.

12 Claims, 40 Drawing Sheets

Related U.S. Application Data is a division of application No. 12/256,911, filed on Oct. 23, 2008, now Pat. No. 8,343,029.

(60) Provisional application No. 60/982,322, filed on Oct. 24, 2007.

(51) Int. Cl.
*A61M 1/10* (2006.01)
*A61M 1/36* (2006.01)
*A61M 25/04* (2006.01)
*A61M 25/10* (2013.01)
*A61M 25/02* (2006.01)

(52) U.S. Cl.
CPC ........ *A61M 25/10* (2013.01); *A61M 2025/0233* (2013.01); *A61M 1/1008* (2014.02); *A61M 1/3659* (2014.02)

(56) References Cited

U.S. PATENT DOCUMENTS

| | | |
|---|---|---|
| 2005/0033107 A1 | 2/2005 | Tsubouchi |
| 2005/0033396 A1* | 2/2005 | Ospyka .................... 607/130 |
| 2009/0182188 A1 | 7/2009 | Marseille et al. |

FOREIGN PATENT DOCUMENTS

| | | |
|---|---|---|
| JP | 2006509596 A | 3/2006 |
| JP | 2006522652 A | 10/2006 |
| JP | 2007510522 A | 4/2007 |
| JP | 2007523686 A | 8/2007 |
| JP | 2007526087 A | 9/2007 |
| JP | 2007534358 A | 11/2007 |
| JP | 2008504943 A | 2/2008 |
| JP | 2008512139 A | 4/2008 |
| JP | 2008513060 A | 5/2008 |
| JP | 2008519653 A | 6/2008 |
| JP | 2008534084 A | 8/2008 |
| JP | 2008538937 A | 11/2008 |
| JP | 2009504255 A | 2/2009 |
| JP | 2009518149 A | 5/2009 |
| WO | 2004019787 A2 | 3/2004 |
| WO | 2004058077 A1 | 7/2004 |
| WO | 2005/037345 A2 | 4/2005 |
| WO | 2006028813 A2 | 3/2006 |

OTHER PUBLICATIONS

Japanese Patent Office, Notice of Reasons for Rejection in JP Application No. 2013-139535, Jun. 16, 2014.

European Patent Office, Invitation to Pay Additional Fees in PCT Application Serial No. PCT/US2014/020474, Jul. 14, 2014.

* cited by examiner

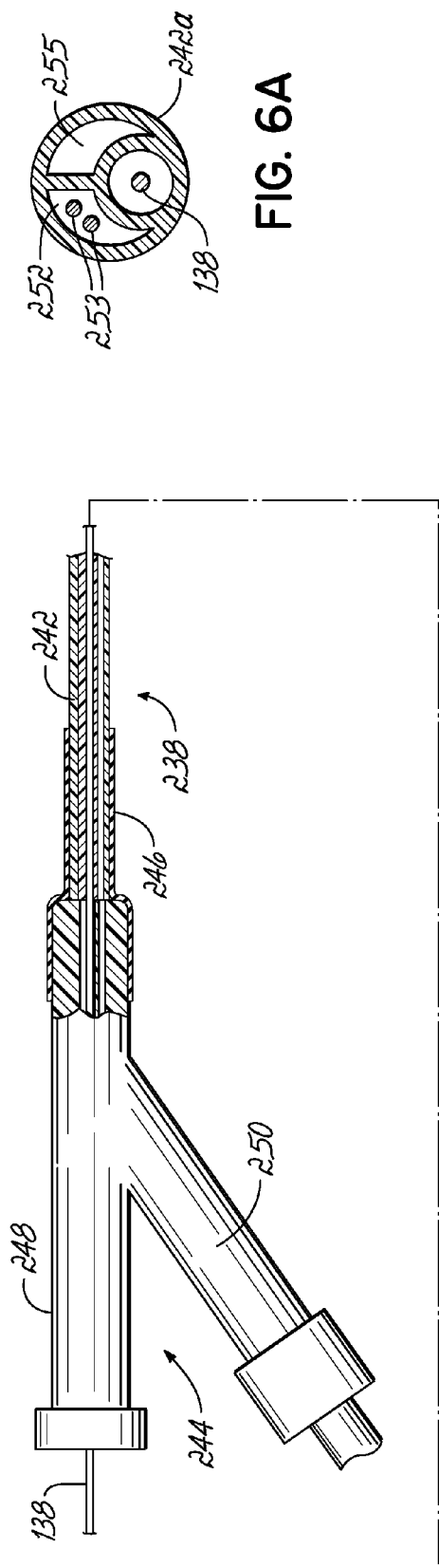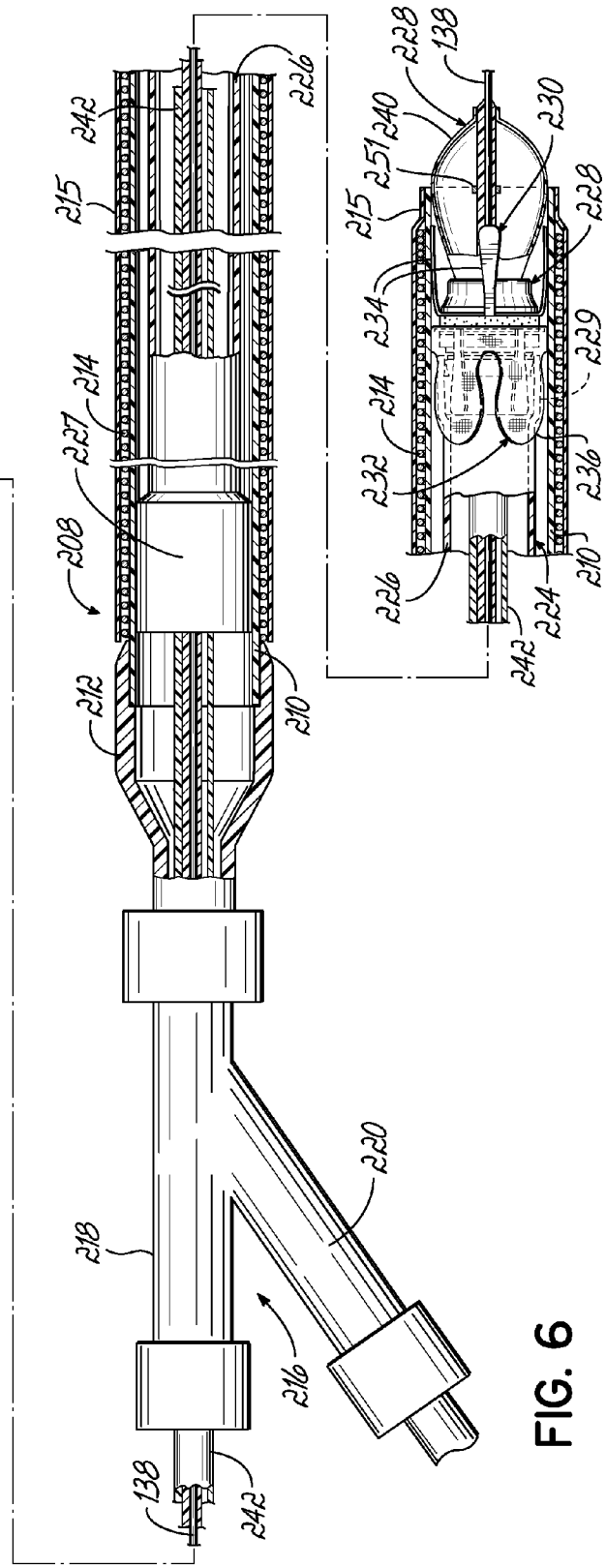

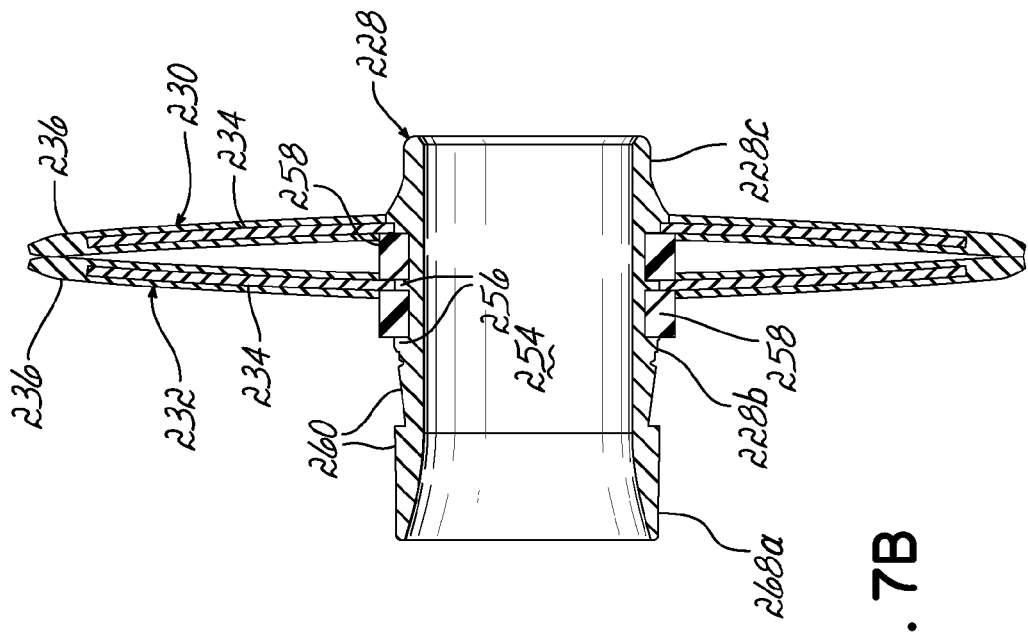
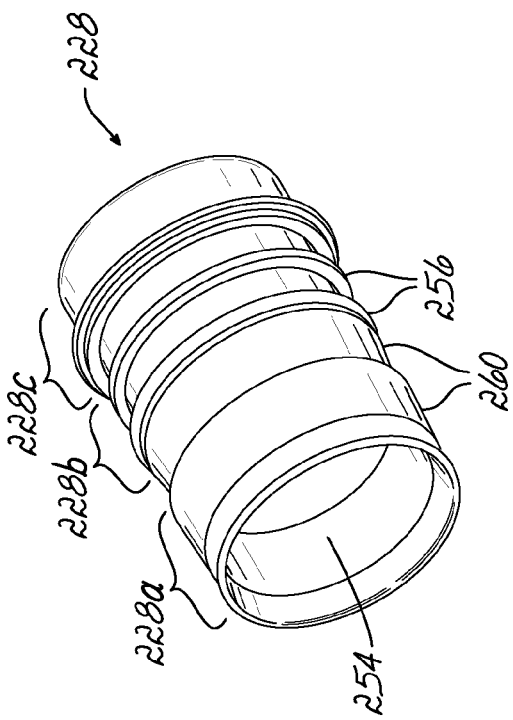
FIG. 7A
FIG. 7B

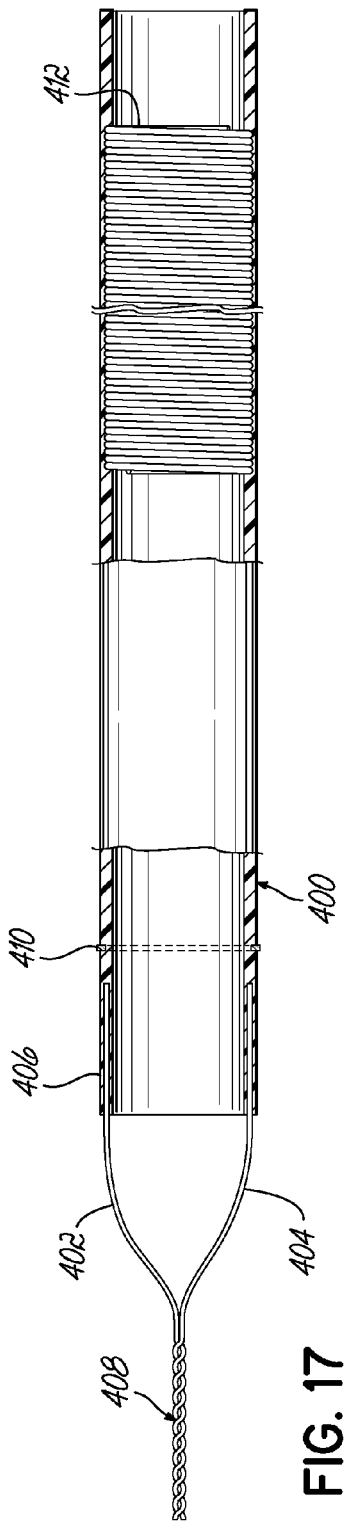
FIG. 17
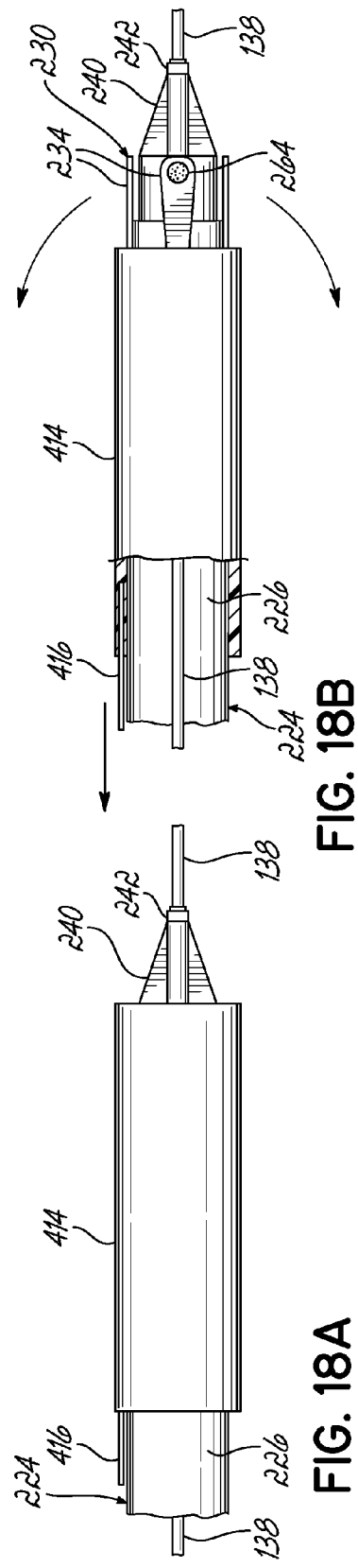
FIG. 18A
FIG. 18B

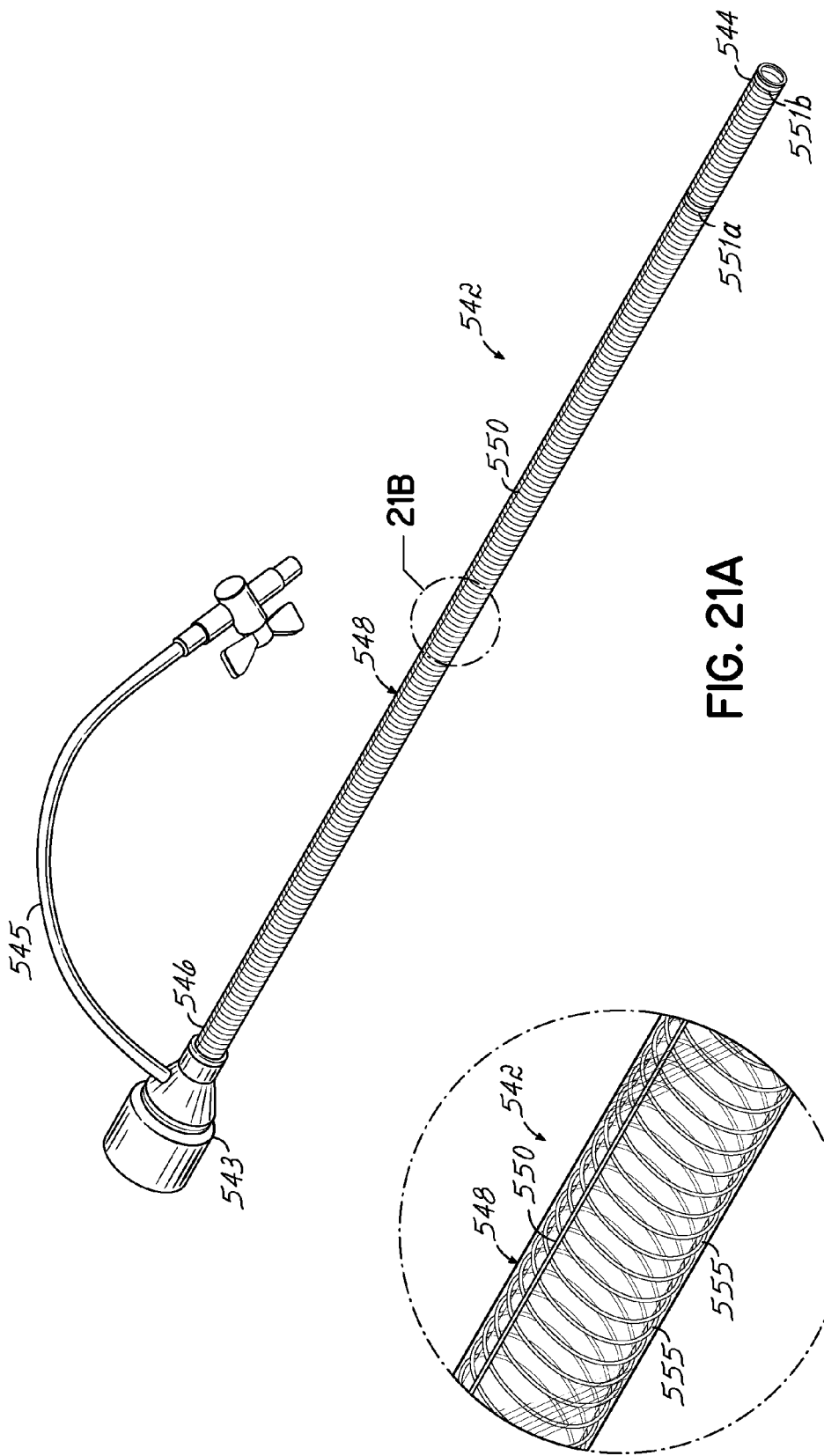

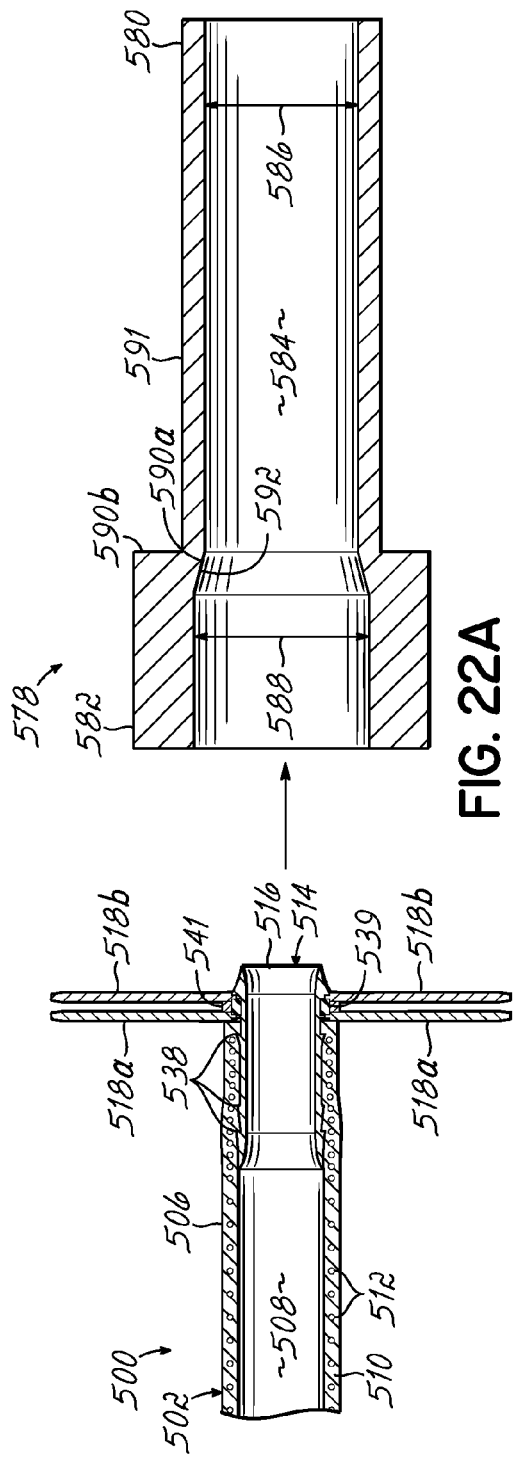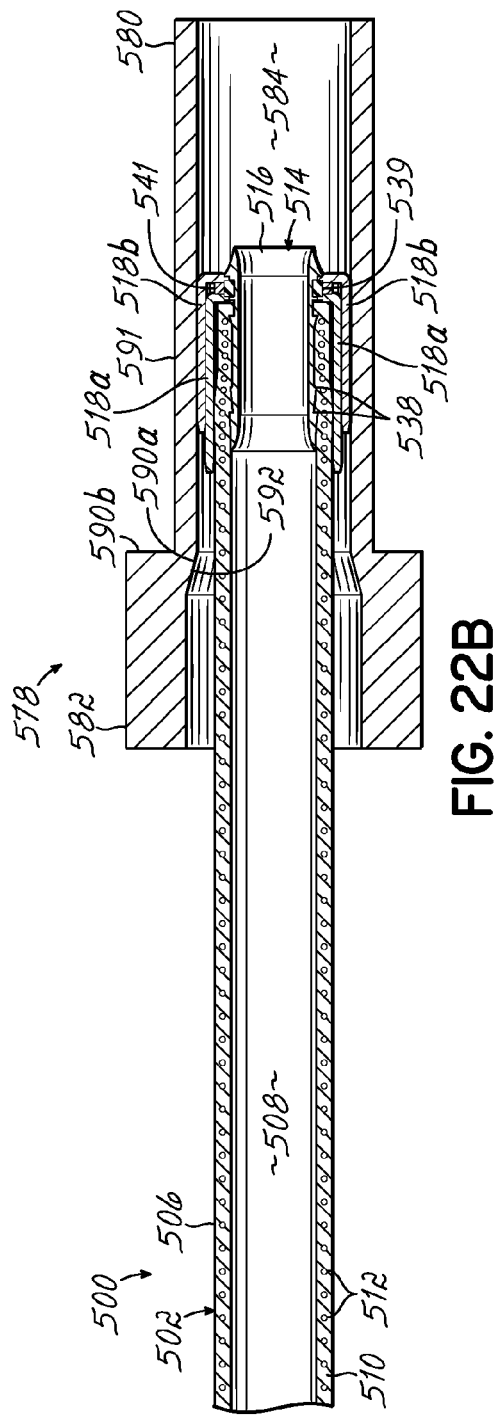

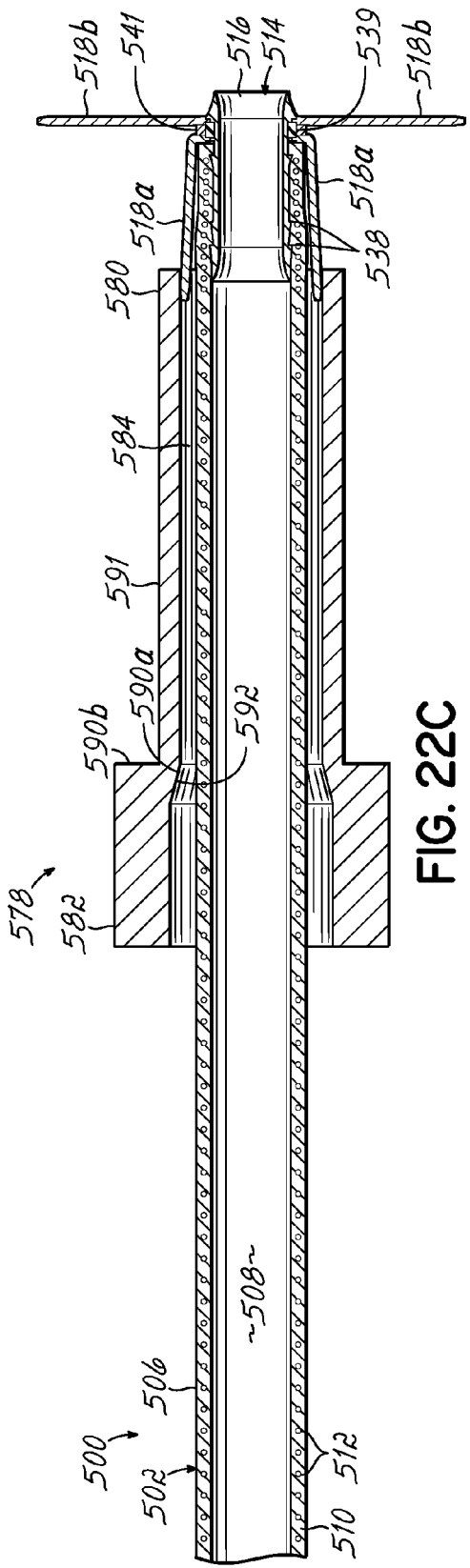
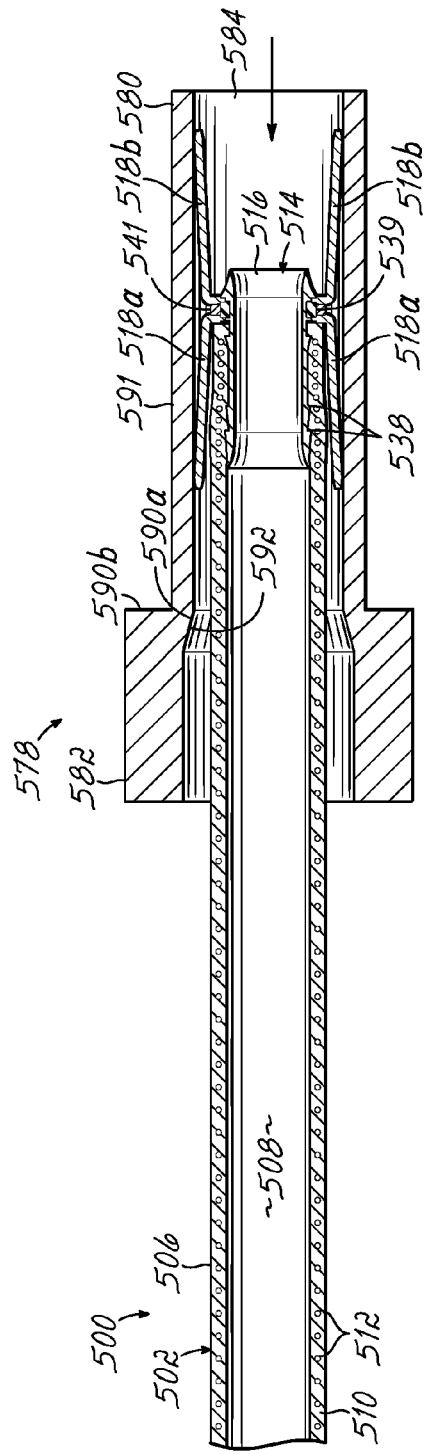
FIG. 22C
FIG. 22D

TRANSSEPTAL CANNULA, TIP, DELIVERY SYSTEM, AND METHOD

CROSS-REFERENCE TO RELATED APPLICATION

This application is a continuation of application Ser. No. 13/788,863, filed Mar. 7, 2013 which is a continuation-in-part of application Ser. No. 13/088,620, filed Apr. 18, 2011 (now U.S. Pat. No. 8,394,010) which is a divisional of application Ser. No. 12/256,911, filed Oct. 23, 2008 (now U.S. Pat. No. 8,343,029), which claims the benefit of Application Ser. No. 60/982,322, filed Oct. 24, 2007, the disclosures of which are incorporated by reference herein.

BACKGROUND

The human heart is the muscle that is responsible for pumping blood throughout the vascular network. Veins are vessels that carry blood toward the heart while arteries carry blood away from the heart. The human heart consists of two atrial chambers and two ventricular chambers. Atrial chambers receive blood from the body and the ventricular chambers, which include larger muscular walls, pump blood from the heart. A septum separates the left and the right sides of the heart. Movement of the blood is as follows: blood enters the right atrium from either the superior or inferior vena cava and moves into the right ventricle. From the right ventricle, blood is pumped to the lungs via pulmonary arteries to become oxygenated. Once the blood has been oxygenated, the blood returns to the heart by entering the left atrium, via the pulmonary veins, and into the left ventricle. Finally, the blood is pumped from the left ventricle into the aorta and the vascular network.

For the vast majority of the population, the events associated with the movement of blood happen without circumstance. However, for many people the heart fails to provide adequate pumping capabilities. These heart failures may include congestive heart failure (commonly referred to as heart disease), which is a condition that results in any structural or functional cardiac disorder that impairs the ability of the heart to fill with or pump blood throughout the body. Presently, there is no known cure for heart disease and long-term treatment is limited to a heart transplant. With only a little over 2,000 patients receiving a heart transplant each year, and over 16,600 more on the waiting list for a heart, there is a persisting need for a cure or at the minimum a means of improving the quality of life of those patients on the waiting list.

One such means of bridging the time gap while awaiting a transplant is a circulatory assist system. These systems, originally developed over a decade ago, provide assistance to the heart by way of a mechanical pump. In this way, blood is circulated throughout the vascular network despite the diseased heart tissue. Traditionally, these circulatory assist systems include an implantable or extracorporeal pump, a controller (internal or external), and inflow and outflow tubes connecting the pump to the vascular network. FDA approved circulatory assist systems partially relieve symptoms of breathlessness and fatigue associated with severe heart failure and drastically improve quality of life.

However, the surgical process associated with the circulatory assist system is highly invasive. At the very least the procedure involves a thoracotomy, i.e., the opening of the thoracic cavity between successive ribs to expose the internal organs. More typical is cardiac surgery, generally known as open-heart surgery, where the sternum is cut and split to expose the internal organs. Once the thoracic cavity is accessed, the surgeon must enter the pleural space and puncture both the pericardium and the myocardial wall. There are great risks and an extensive recovery time associated with the invasive nature of the implantation surgery. As such, some patients with severe symptoms are not healthy enough for surgery to receive a circulatory assist system.

There continues to be a need for improvements in this area. For example, there is a need to provide greater accessibility to the circulatory assist system by minimizing the invasiveness of the implantation surgery for those patients that would gain the most benefit while awaiting a heart transplant. Specifically, there continues to be a need to minimize the invasiveness of the procedure by at least removing the need to enter the pleural space or puncturing the pericardium and myocardial wall. Further, there is a need for the procedure to be easily performed within a cardiac suite or cardiac electrophysiology lab, rather than within an operating room, so as to increase the availability to patients.

SUMMARY

In one embodiment of the present invention, a circulatory assist system is provided. The system comprises a cannula assembly, further comprising a cannula body for directing blood from the heart of a patient, having distal and proximal ends and a lumen therebetween. The cannula assembly further comprises a tip coupled to the distal end of the body, the tip having an opening. A pump for drawing blood into the cannula assembly and dispensing the blood from the cannula assembly and into the patient circulatory system is provided. The lumen of the cannula body further comprises a first inner diameter at the proximal end and a second inner diameter at the distal end, the first inner diameter being larger than the second inner diameter, and a tapered portion defined as a decrease in inner diameter from the first inner diameter to the second inner diameter between the proximal and distal ends. The tapered portion configured to prevent cavitation of the blood within the cannula.

In another illustrative embodiment of the present invention, a circulatory assist system is provided. The system comprises a cannula body having distal and proximal ends and a lumen therebetween and a pump for drawing blood into the cannula assembly and dispensing the blood from the cannula assembly and into the patient circulatory system. The system further comprises a tip at the distal end of the cannula body in fluid communication with the lumen and configured to communicate the lumen with a cavity of the heart. The tip includes a distal portion having first and second ends, having first and second diameters, respectively, the second end more distal than the first end, and the second diameter larger than the first diameter. The tip is configured to prevent a drop of pressure of blood entering the tip and traveling through the cannula.

In another illustrative embodiment of the present invention, a circulatory assist system is provided. The system comprises a cannula assembly having distal and proximal ends and a lumen therebetween and a pump for drawing blood into the cannula assembly and dispensing the blood from the cannula assembly and into the patient circulatory system. The system further comprises a delivery sheath for delivering the cannula assembly through the patient circulatory system. The delivery sheath is configured to receive the cannula assembly and move relative thereto for deploying the cannula adjacent a heart cavity and further comprises a distal end, a proximal end, and a body therebetween. The body further comprises a longitudinally disposed tensile element embedded therein and configured to prevent deformation of the body when the cannula assembly moves relative to the delivery sheath.

In another illustrative embodiment of the present invention, a delivery system for delivering a cannula including an anchor to the heart of a patient is provided. The anchor has contracted and expanded states and the delivery system comprises a delivery sheath, the sheath configured to receive the cannula assembly and move relative thereto for deploying the anchor into the expanded state. The delivery system further comprises a loading device configured to receive the anchor in the contracted state and assist the delivery of the cannula into the delivery sheath with the anchor in the contracted state. The loading device further comprises a proximal end, a distal end and a lumen therebetween, the proximal end having a first inner diameter and the distal end having a second inner diameter, the first diameter being larger than the second diameter. The loading device further comprises a stepped portion in the lumen where the first inner diameter changes to the second inner diameter, and a taper at the stepped portion, defined as a decrease in inner diameter between the first inner diameter and the second inner diameter. The taper is configured to prevent damage to the anchor when the sheath receives the cannula assembly.

In another illustrative embodiment of the present invention, a circulatory assist system for assisting the flow of blood through a patient circulatory system is provided. The system comprises a cannula assembly for directing blood from the heart of a patient, the cannula assembly comprising a flexible cannula body including a proximal end and a distal end and a lumen therebetween. The system further comprises a pump for drawing blood into the cannula assembly and dispensing the blood from the cannula assembly and into the patient circulatory system, the pump further including an inlet and an outlet. The system further comprises an adaptor device between the inlet and the cannula assembly, thereby fluidicly communicating the inlet and cannula assembly. The system further comprises an outflow cannula fluidicly communicating the outlet and an artery of a patient. The inlet is disposed facing a generally lateral direction relative to the patient.

In another illustrative embodiment of the present invention, a method of deploying a circulatory assist system into a circulatory system of a patient is provided. The assist system includes a cannula assembly and a pump and assists the flow of blood through the circulatory system. The method comprises directing a cannula assembly into the circulatory system of a patient, wherein a distal end of the cannula assembly is in fluid communication with a chamber of the heart, and the body travels therefrom to the superior vena cava and the subclavian vein, whereby the cannula assembly exits from the subclavian vein at a point thereof. The method further comprises fluidicly communicating an outlet of the pump with an artery with an outflow cannula therebetween, and fluidicly communicating the cannula assembly with an inlet of the pump with a cannula adaptor therebetween, wherein the inlet is disposed facing a generally lateral direction relative to the patient.

DETAILED DESCRIPTION OF DRAWINGS

FIG. 6 is a side elevational view of the delivery apparatus with the transseptal cannula assembly, shown in partial cross-section.

FIG. 6A is a cross-sectional view of an alternative catheter shaft similar to the one shown in FIG. 6.

FIG. 7A is a perspective view of one embodiment of the tip of the transseptal cannula assembly.

FIG. 7B is a transverse cross section of a transseptal cannula embodiment where the anchor tips of right and left anchors are aligned with one another.

FIG. 17 is a side elevation view, in partial cross-section, of an alternate embodiment of the delivery device.

FIG. 18A is a side elevation view of the distal portion of another embodiment of the delivery device having a truncated sheath.

FIG. 18B is a side elevation view of the distal portion of the embodiment of FIG. 18A with the truncated sheath being retracted and before deployment of a first anchor.

FIG. 21A is a perspective view of one embodiment of a delivery sheath.

FIG. 21B is a detailed perspective view of the delivery sheath of FIG. 21A.

FIGS. 22A through 22D show side cross-sectional views of the steps involved in loading the cannula assembly into a loading device.

DETAIL DESCRIPTION

Figure 1A:
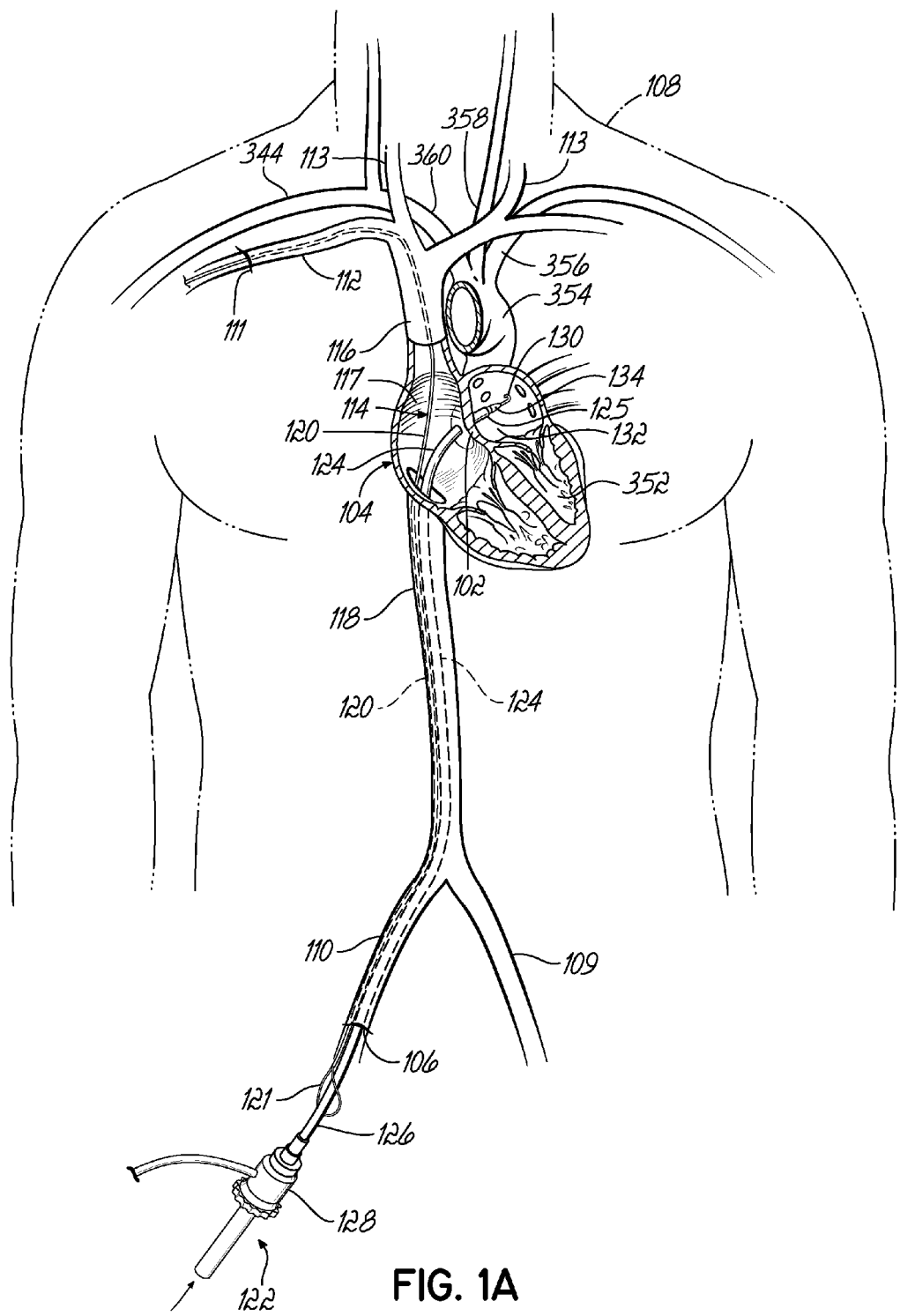
FIGS. 1A through 1E are diagrammatic views of an exemplary method of accessing the septum of the human heart, shown in cross-section.

Implanting a circulatory assist system can begin with a percutaneous transseptal crossing procedure. FIGS. 1A-1E illustrate a portion of the procedure according to one embodiment that involves the placement of an anchoring guide-element across the intra-atrial septum 102 of the heart 104. The method begins with the surgeon making a primary incision site 106 in the patient 108 that is substantially near a superficial vein. A suitable superficial vein for the primary incision site 106 can include a peripheral vein, on either of the right or left sides of the patient, such as the left or right femoral veins 109, 110, or others known by one skilled in the art. It is generally preferred that the primary incision site 106 is inferior to a secondary incision site 111, that is substantially near a suitable superficial vein, including peripheral veins such as the right subclavian vein 112, the jugular vein 113, at the junction between the right subclavian vein 112 and the jugular vein 113, or other suitable peripheral veins known by one skilled in the art. Similar veins or locations on the left side of the body could also be used.

The use of an inferior incision site is better suited for accessing the left atrium and the intra-atrial septum due to the angle of the heart and the septum with respect to the inferior and superior vena cava. Yet, some procedures, such as the implantation of a circulatory assist system, necessitate a more superiorly located incision site. As a result, the surgeon may find it beneficial to first access the septum and then transition to the secondary incision site, as will be described in detail.

The surgeon can begin the procedure as shown in FIG. 1A, by directing a standard snare device 114 from the secondary incision site 111, down the superior vena cava 116, the right atrium 117, the inferior vena cava 118, to the right femoral vein 110, and through the primary incision site 106. The standard snare device 114 can include a body 120 extending between the primary and secondary incision sites 106, 111 and a snare loop 121 upon the distal end of the body 120. Alternatively, snare loop 121 can remain within the right femoral vein 110 and not extend through the primary incision site 106, though this is not shown.

The surgeon may then access and cross the intra-atrial septum 102. A suitable device utilized for percutaneous transseptal crossing can be a transseptal access delivery system 122 having a percutaneous transseptal sheath 124 with a distal end 125, a proximal end 126, a lumen (not shown) extending therebetween, and a proximally located hub 128 upon the proximal end 126 of the percutaneous transseptal sheath 124. The distal end 125 of the percutaneous transseptal sheath 124 is directed through the snare loop 121, into the primary incision site 106, up the inferior vena cava 118, and into the right atrium 117.

Once the percutaneous transseptal sheath 124 enters the right atrium 117, a transseptal needle (not shown) with a guidewire 130 extending therethrough are back-loaded into the proximally located hub 128, through the lumen of the percutaneous transseptal sheath 124, and into the right atrium 117. The transseptal needle (not shown) punctures the intra-atrial septum 102 and allows the guidewire 130 to enter the left atrium 132. The distal end 125 of the percutaneous transseptal sheath 124 is advanced over the transseptal needle, through the puncture within the intra-atrial septum 102, and into the left atrium 132. This advancement of the percutaneous transseptal sheath 124 can be enabled by the use of an obturator 134; however, the method should not be considered so limited.

After the distal end 125 of the percutaneous transseptal sheath 124 is within the left atrium 132, the transseptal needle (not shown) and the guidewire 130 are retracted completely (see FIG. 1B) leaving only the percutaneous transseptal sheath 124 within the left atrium 132. The transseptal access delivery system 122 is now ready to receive an anchoring guide-element according to one of the embodiments herein and explained in detail below.

Generally, the anchoring guide-element includes a body portion having a proximal end and a distal end, wherein the distal end includes an anchoring portion. Additional features may be included and are provided in detail below.

Figure 2A:
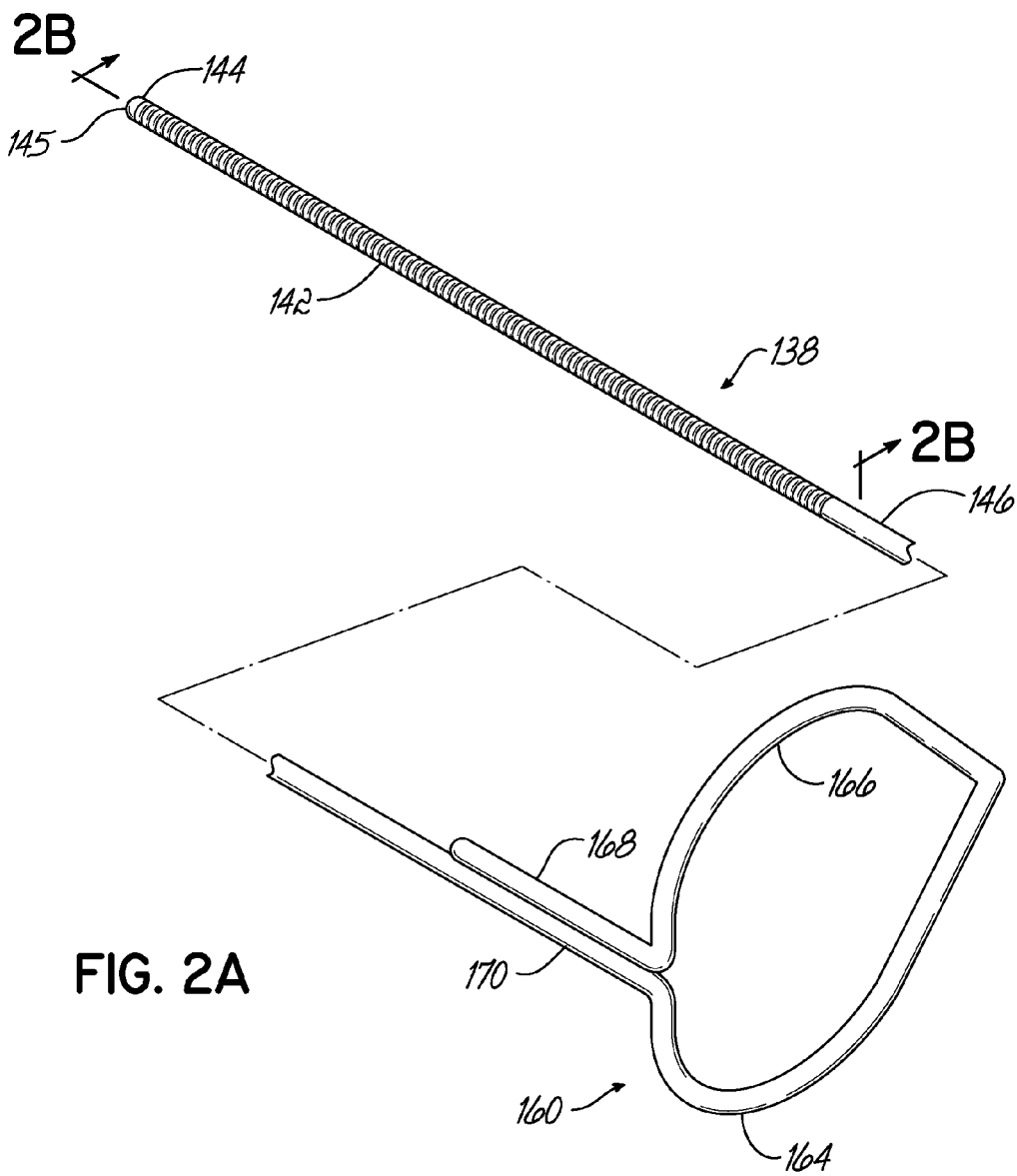
FIG. 2A is a perspective view of the anchoring guide-element.
Figure 2B:
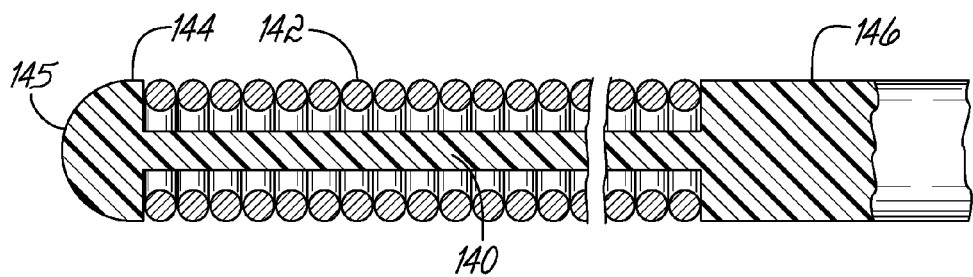
FIG. 2B is an enlarged cross-sectional view taken along line 2B-2B of the coil end of the anchoring guide-element.

As shown in FIGS. 2A and 2B, the body portion of the anchoring guide-element can be constructed as a wire 138 having an internal core wire 140 can be encased within a coil 142 and/or a polymeric jacket (not shown). The core wire 140 is constructed from a superelastic material (such as Nitinol, i.e. NiTi) and will range in diameter from approximately 0.127 mm to approximately 0.254 mm over the length of the wire 138. The core wire 140 can be tapered or stepped, depending on the desired level of flexibility (i.e. greater taper would increase the flexibility). The coil 142 can be constructed from a tight pitch coil of a metallic material, such as stainless steel or platinum, and can include a round or rectangular cross section, with an effective diameter ranging from approximately 0.0254 mm to approximately 0.127 mm. Typically, the entire length of the wire 138 can range from approximately 30 cm to approximately 300 cm, which will depend upon the distance between the heart and the incision site. This construction provides a flexibility that aids the surgeon in maneuvering the anchoring guide-element through the percutaneous transseptal sheath, as will be discussed below.

The coil 142 and the core wire 140 can be joined at the proximal end 144 in accordance with FIG. 2B, by an end radius 145, which can be formed by adjoining the coil 142 and the core wire 140 by a laser soldering process, a welding technique, or other known methods. After the coil 142 and the core wire 140 are adjoined, the wire 138 can then be coated with a polymeric material (not shown), such as a polyethylene or a fluorinated polymer, which will improve the movement of the wire 138 with respect to surgical devices directed coaxially over the wire 138.

Returning again to FIG. 2A, a distal end 146 of the wire 138 is illustrated as a straight portion, which can be an extension of the core wire material. The distal end 146 provides a stiff region that may be pre-formed as necessary to provide support to coaxially loaded devices as well as a transition between the body portion and an anchoring portion, which is described below. The distal end 146 ranges in length from approximately 1 cm to approximately 10 cm, as is necessary or desired.

The anchoring guide-element includes an anchoring portion upon the distal end of the body portion. While the anchoring portion can include any number of configurations, three are specifically described herein: a double bend 160 (FIG. 2A), a plurality of struts 150 (FIGS. 2C and 2D), and a loop 162 (FIG. 2E).

The double bend 160 of FIG. 2A can include first and second curved portions 164, 166 positioned at the distal end 146 of the wire 138. The first and second curved portions 164, 166 can be opposed, i.e. positioned substantially 180° apart, to optimize load-bearing benefits once it is positioned against the septum (not shown). An end portion 168 can extend proximally from the location of the double bend 160. The distal end 146 of the wire 138 is affixed to a proximal end 170 of the double bend 160 by a standard joining process such as welding or gluing. If desired, a thin polymeric sleeve (not shown) can be included to secure the end portion 168 to the proximal end 170.

The double bend 160 of FIG. 2A can be formed at the distal end 146 of the wire 138 by a secondary forming process of the core wire material, which is an extension of the body portion. Alternatively, the double bend 160 can be constructed separately, from like materials, and then the proximal end 170 of the double bend 160 can be attached to the distal end 146 of the wire 138 by welding or gluing.

Figure 2C:
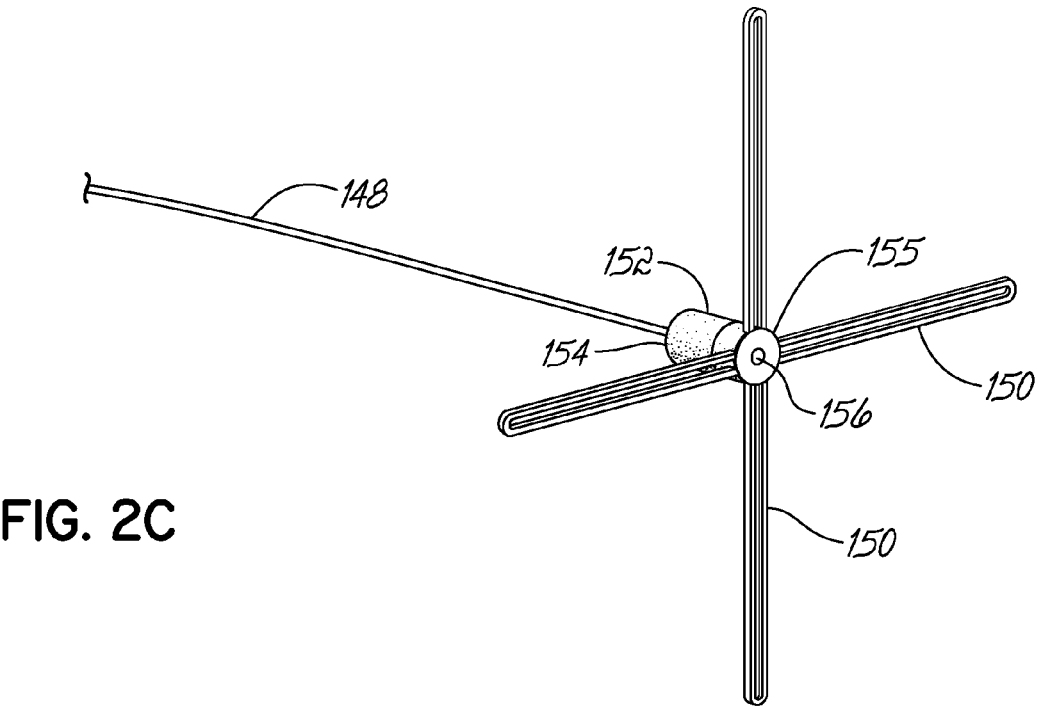
FIGS. 2C through 2E are perspective views of alternate embodiments of the anchoring feature of the anchoring guide-element.

In FIG. 2C, the anchoring portion is illustrated as the plurality of struts 150. Generally, the plurality of struts 150 extend substantially transverse to a central axis, which is represented by the body portion (illustrated as a fiber 148 that will be discussed below). While four struts 150 are shown, this number is not so limited. Rather, embodiments could be envisioned where two struts 150 or up to six or eight struts 150 may be necessitated for a particular surgeon's needs or preference. To soften the wire stock materials, coils (not shown) can be added to the distal portion of each strut 150. Alternatively, the struts 150 can be dip-coated with a polymer. Each of the plurality of struts 150 can be constructed into a desired shape from a flat sheet stock of superelastic material, such as NiTi or MP35N. The superelastic material allows each of the plurality of struts 150 to be folded and/or held in a position that is parallel to the central axis, although a parallel position is not shown in the figure. Once released, the plurality of struts 150 will automatically spring to a deployed state (FIG. 2C), where the deployed state is transverse to the central axis. Alternatively, each of the plurality of struts 150 are constructed from a wire stock of the desired material and formed into the desired shape. Each of the plurality of struts 150 can range in thickness from approximately 0.13 mm to approximately 0.25 mm, and in length from approximately 0.025 mm to approximately 0.51 mm. After formation, each of the plurality of struts 150 can undergo a secondary process, such as electropolishing, to remove rough edges generated when forming the desired curvature.

As further illustrated in FIG. 2C, the plurality of struts 150 are attached to a fiber 148. The fiber 148 can be made from a standard suture material, such as a polypropylene (for example etched polytetrafluoroethylene; ePTFE). Because the fiber 148 lacks a level of rigidity suitable to serve as a guidewire, an anchor magnet 152 is included to provide a means for attaching a reinforcement structure over the fiber 148, which will be discussed in detail below. The outer diameter of the anchor magnet 152 is approximately equal to the diameter of a conventional guidewire (i.e. approximately 0.127 mm to approximately 6.35 mm, generally) and has an overall length such that the proximal end 154 of the anchor magnet 152 will reside within the right atrium 117 (FIG. 1A) while the plurality of struts 150 (or other anchoring portion) resides within the left atrium 132 (FIG. 1A) and along the intra-atrial septum 102 (FIG. 1A). Generally, an anchor magnet length ranging from approximately 1 mm to approximately 5 mm is sufficient to accommodate a variety of septal thicknesses. The fiber 148 extends through an inner diameter (not shown) of the anchor magnet 152 and through a central portion 155 of the plurality of struts 150. The fiber 148 is secured at the distal end 156 by welding or other means.

Figure 2D:
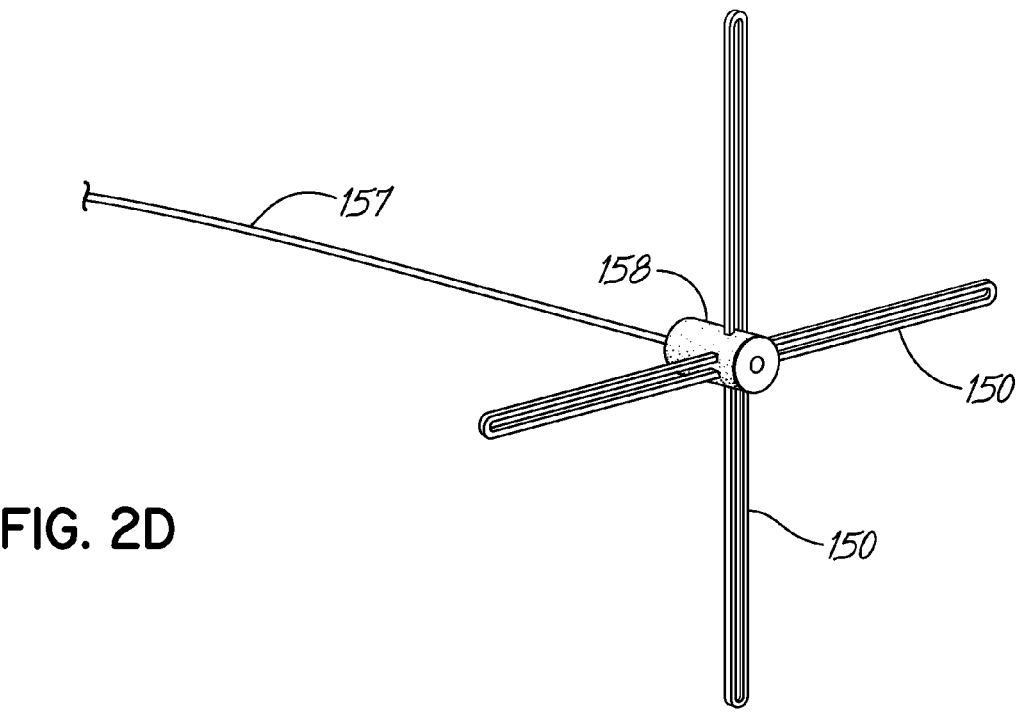
Figure 2E:
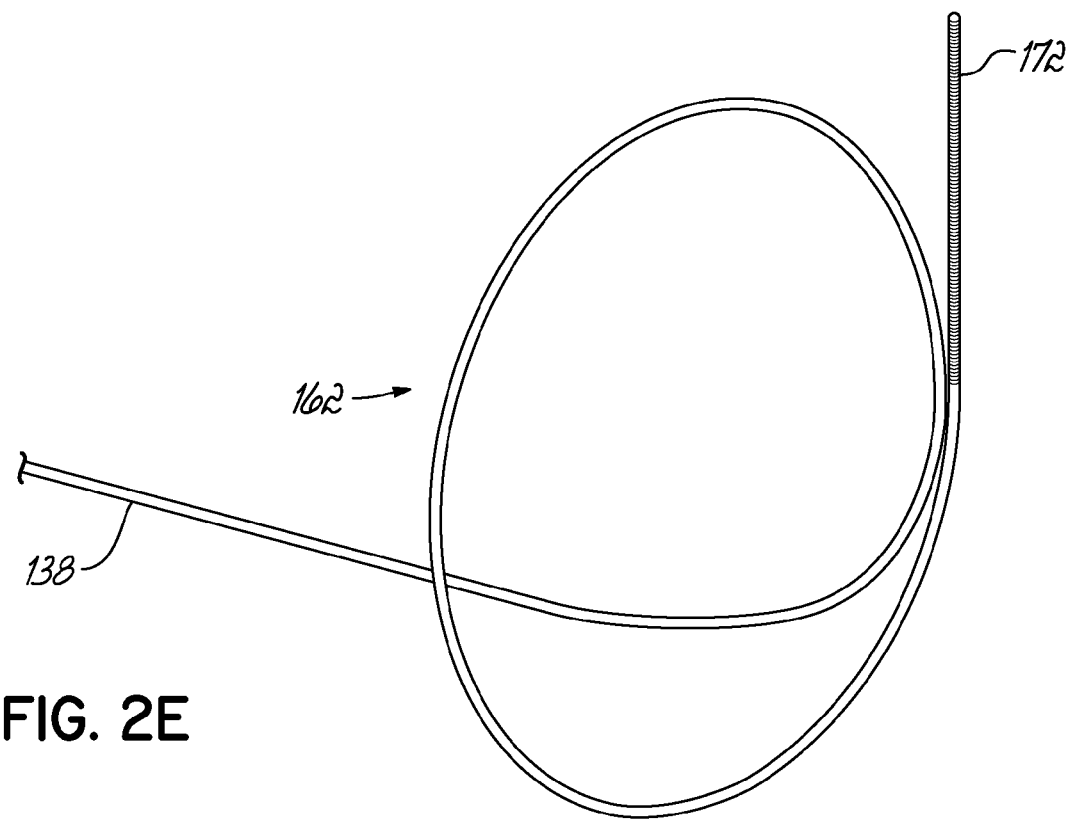
Figure 3:
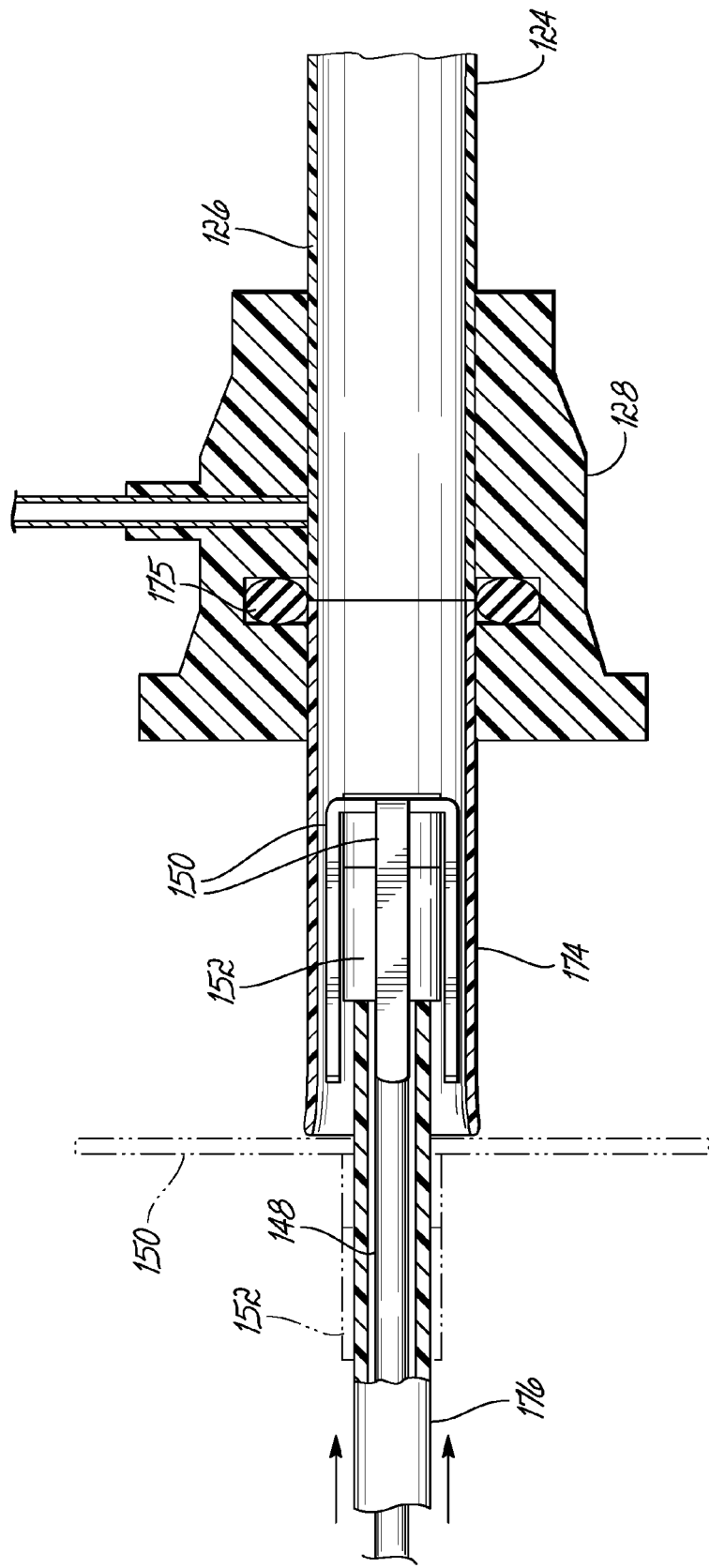
FIG. 3 is a longitudinal cross section of a method of loading an anchor device into the hub of the percutaneous transseptal sheath.

FIG. 2D illustrates an alternative embodiment in which a flexible wire 157, constructed from NiTi, for example, is welded to a hub 158 constructed, for example, of a radiopaque material for localization. The flexible wire 157 can be solution dipped or include TEFLON or other polymer layer that is suitable to lower the frictional coefficient. The proximal end (not shown) of the flexible wire 157 can be similar in construction to the coil 142 and core wire 140 of FIG. 2B. The plurality of struts 150 that extend substantially transverse to a central longitudinal axis are welded onto the hub 158. Though not specifically shown, each of the plurality of struts 150 can include a spring coil and an end radius upon each distal end, constructed similar to the body of FIG. 2B. Further, each of the plurality of struts 150 can include a curvature such that the outer end of each of the plurality of struts 150 is positioned more proximally than the inner end located near the hub.

FIG. 2E illustrates a third embodiment of the anchoring portion, namely the loop 162 having a distal end portion 172 and a proximal end (not shown). Formation of the loop 162 can be by heat treatment processing. The end portion 172 of the loop 162 can be a core and coil assembly that is similar in construction and materials to the wire of FIG. 2A to provide increased rigidity to the end portion 172, which aids the surgeon in maneuvering the apparatus. Herein, the end portion 172 can range in length from approximately 1 cm to approximately 5 cm depending upon the desired shape of the loop 162. That is, if a "straight" shape is desired, then a length of approximately 1 cm may be appropriate; however, "j" or other shapes may require at least 5 cm.

The anchoring portion, regardless of the embodiment employed, may further include a portion constructed from platinum or platinum-iridium stainless steel so as to change the radiopacity of the anchoring portion. Radiopaque materials, such as platinum-iridium, stainless steel, tungsten, or tantalum, allow for remote visualization of a device in vivo, by non-invasive devices such as X-ray, real-time fluoroscopy, or intracardiac echocardiograph.

Figure 1B:
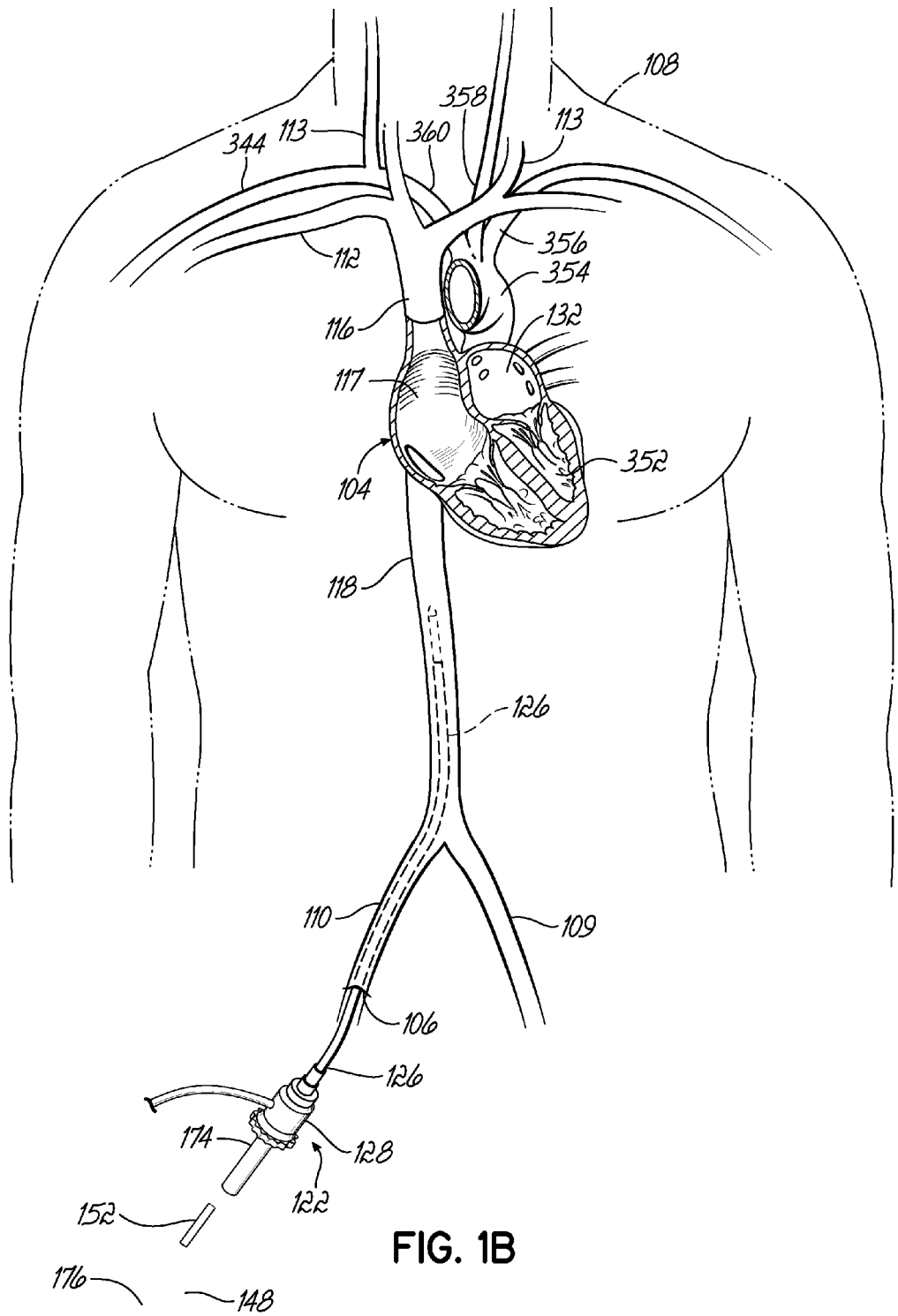
Figure 1C:
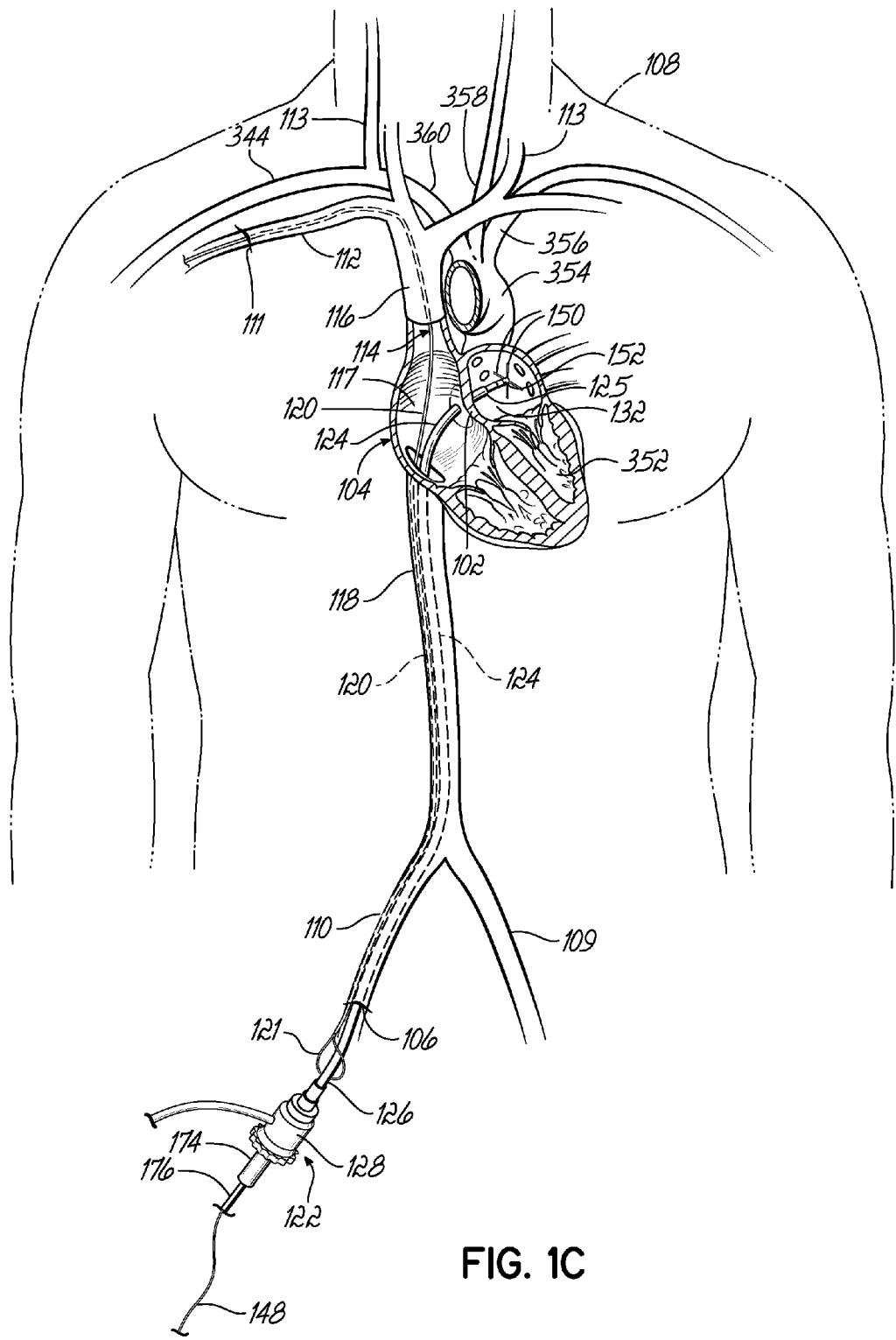
Figure 1D:
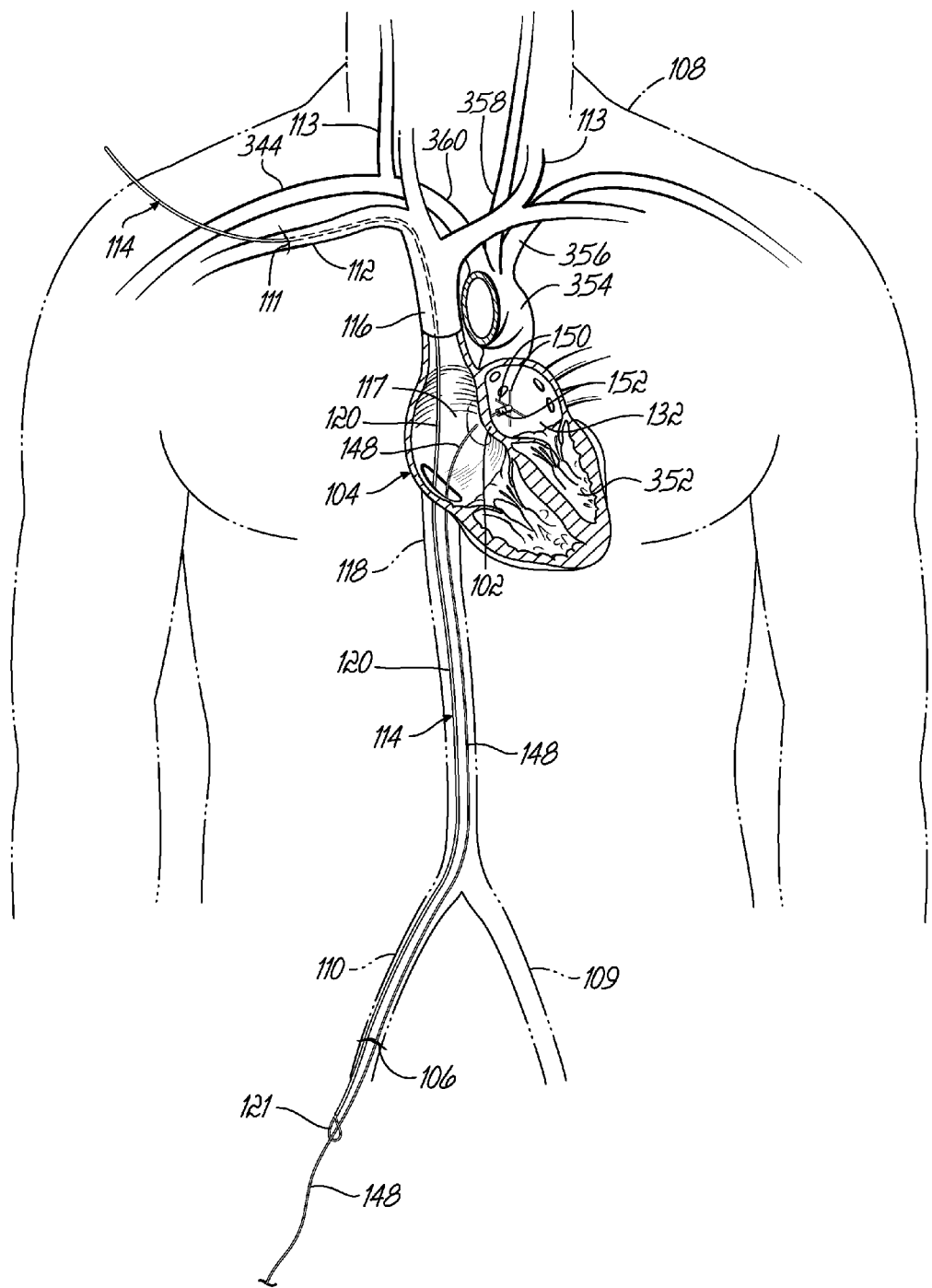

With the details of illustrative anchoring guide-elements described with some detail, the method of inserting the anchoring guide-element can continue with reference made to FIGS. 1B-1D. While these figures illustrate the anchoring guide-element particularly as the fiber 148 with the plurality of struts 150, it would be understood that other embodiments, such as any of the embodiments described above for the body portion and/or anchoring portion would be appropriate.

FIG. 1B illustrates the plurality of struts 150 back-loaded into the hub 128 via a loading tube 174. The loading tube 174 (see FIG. 2 for greater detail) will cause the plurality of struts 150 to be deflected from an expanded state (shown in phantom) and into a position that is substantially parallel to a central axis (as was described previously). The loading tube 174 can also act as a mechanism for opening a hemostatic valve (shown as an O-ring 175) within the hub 128. In operation, the plurality of struts 150 are positioned at a proximal end of the loading tube 174. By advancing the plurality of struts 150 into the loading tube 174 while maintaining the loading tube 174 stationary, the plurality of struts 150 are deflected such that the anchoring portion is deflected and enters the loading tube 174. If necessary, due to the non-rigid character of the fiber 148, advancing the struts 150 can be accomplished by a pusher tube 176. Accordingly, a distal end of the pusher tube 176 contacts the anchor magnet 152 and thereby directs the plurality of struts 150 into the loading tube 174 and the percutaneous transseptal sheath 124 (FIG. 1B), and eventually into the left atrium 132 (FIG. 1B) as described below. In construction, the pusher tube can be a hollow cylindrical structure that allows the fiber 148 to extend therethrough. In some instances, the pusher tube 176 can be constructed as a solid cylindrical structure of either a polymeric or a metallic material as in FIG. 1B.

In operation, and as will be appreciated by reviewing FIGS. 1B and 1C, the plurality of struts 150 are advanced through the lumen of the percutaneous transseptal sheath 124 by the pusher tube 176 until the plurality of struts 150 emerge from the distal end 125 of the percutaneous transseptal sheath 124 and thereby enter the left atrium 132. Continued advancement with the pusher tube 176 extends the plurality of struts 150 beyond the percutaneous transseptal sheath 124 causing each of the plurality of struts 150 to be deployed from the position parallel to the central axis to the position transverse to the central axis (as described previously).

As illustrated in FIG. 1C, once the plurality of struts 150 are deployed within the left atrium 132, the surgeon can then retract the percutaneous transseptal sheath 124 and the pusher tube 176 from the primary incision site 106 leaving the plurality of struts 150 in position within the left atrium 132, which is shown in FIG. 1D. A slight retraction or pulling of the proximal end (not shown) of the fiber 148 pulls the plurality of struts 150 within the left atrium 132 into contact with the intra-atrial septum 102 within the left atrium 132 while the fiber 148 extends from the primary incision site 106 and through the snare loop 121. The snare loop 121 is then operable to transition, or move, the fiber 148 from the primary incision site 106 to the secondary incision site 111.

Figure 1E:
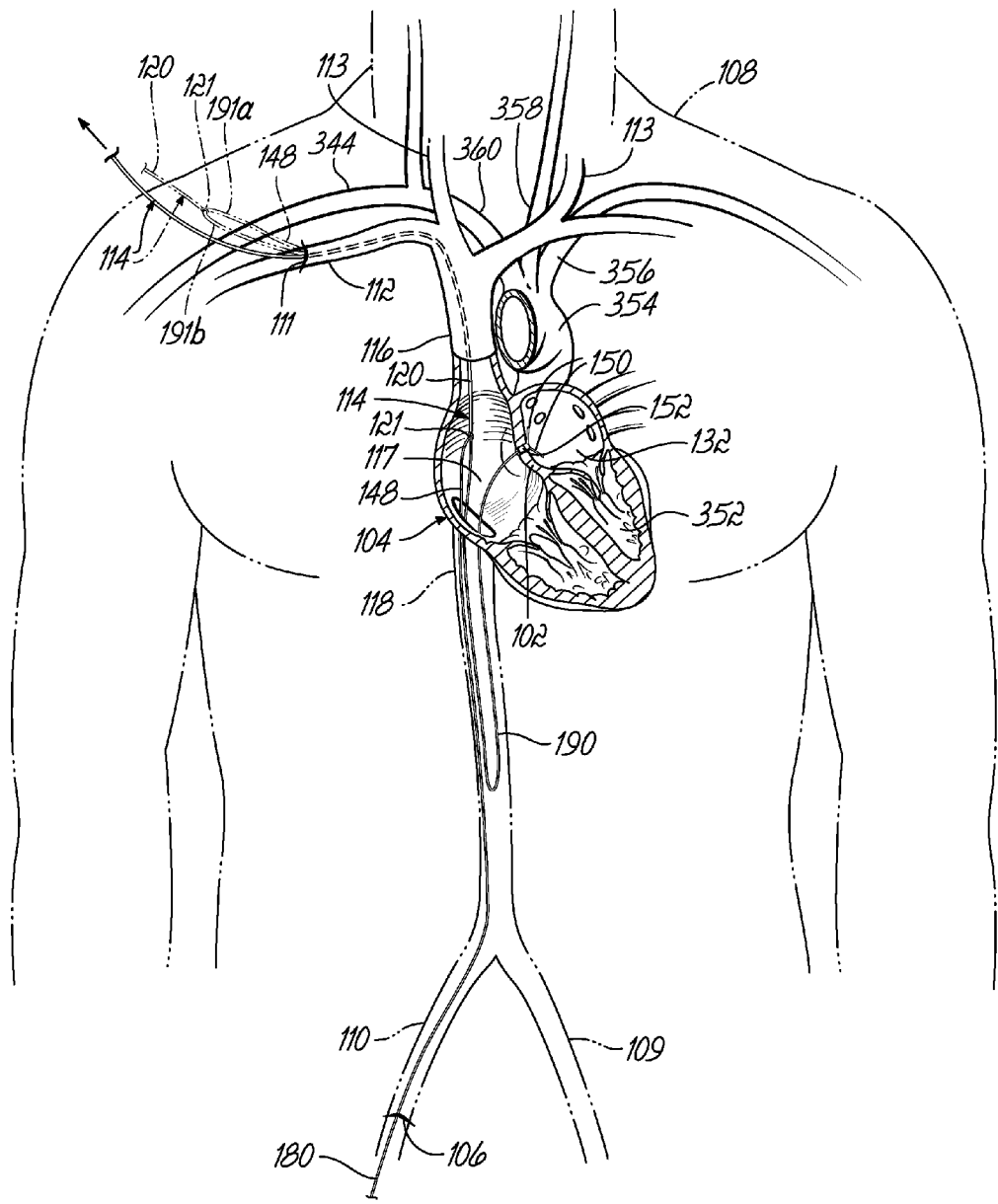

FIG. 1E shows the snare loop 121 as the surgeon begins retracting the snare device 114 and transitioning the fiber 148 from the primary incision site 106 to the secondary incision site 111. The plurality of struts 150 are secured to the intra-atrial septum 102 within the left atrium 132 and will resist the removal of the anchoring guide-element from the intra-atrial septum 102. By retracting of the snare device 114, a prolapsed portion 190 of the fiber 148 is formed while the proximal end 180 extends beyond the primary incision site 106. In some embodiments, the snare loop 121 can be locked about the proximal end 180 of the fiber 148.

FIG. 1E illustrates the snare device 114 after continuing the retraction, which results in the snare loop 121 (in phantom) and a loop portion of the fiber 148 (in phantom) extending externally from the secondary incision site 111. The proximal end 180 of the fiber 148 extends beyond the primary incision site 106. The loop portion of the fiber 148 will have a first side 191*a* that extends from the loop portion to the anchoring portion and a second side 191*b* that extends from the loop portion to the proximal end 180 of the fiber. The surgeon can then slightly pull on the first and/or second sides 191*a*, 191*b* of the loop portion of the fiber 148 to determine which extends to the anchor portion. That is, when the second side 191*b* is pulled, movement is visually detected at the proximal end 180; otherwise, if the first side 191*a* is pulled, then no movement is detected. In this way, the surgeon does not inadvertently apply too much force to the first side 191*a*, thereby causing the anchoring portion to pull through the intra-atrial septum 102.

With the proximal end of the anchoring guide-element extending from the secondary incision site, subsequent percutaneous transseptal procedures can ensue. However, as noted previously, the fiber 148 may not provide a sufficient level of rigidity to support the positioning of surgical devices coaxially over the fiber 148. Thus, it may be necessary to increase the rigidity of the fiber 148 by way of a reinforcement structure, such as an over-wire assembly, described below.

Figure 4A:
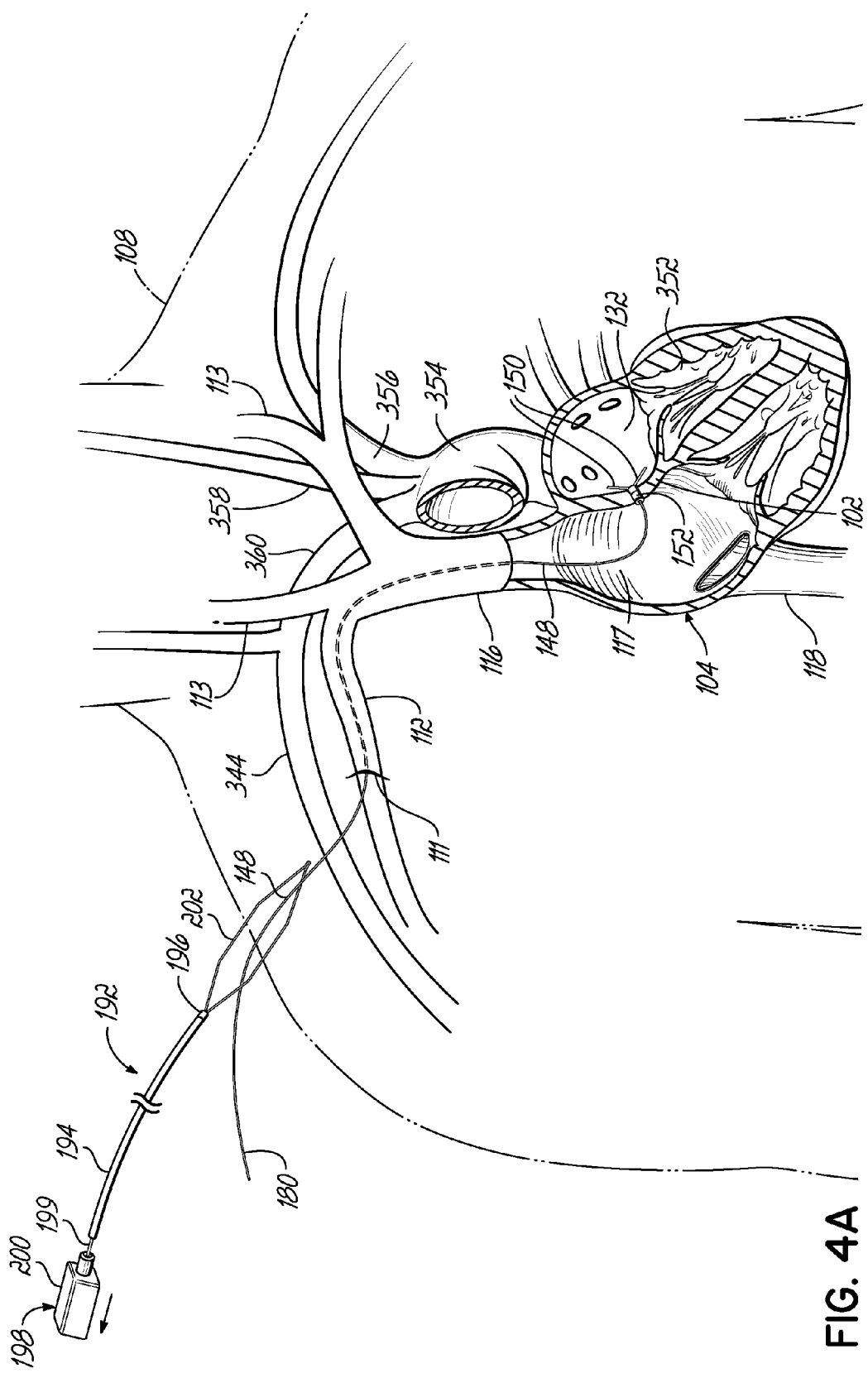
FIGS. 4A through 4D are diagrammatic views of a method of stabilizing the fiber of the anchoring guide-element, extending through a superior incision site.

FIG. 4A shows an over-wire assembly 192 to increase the strength of the anchoring guide-element. The over-wire assembly 192 includes a body 194 having a distally located magnet 196. The body 194 will be positioned over the fiber 148 to provide increased rigidity. The body 194 can be constructed of either a polymeric (e.g. polyimide or polyamide) or metallic (e.g. stainless steel or NiTi) material. When a polymeric material is used, the outer surface of the polymeric material may further be coated with material that reduces the frictional coefficient of the surface, such as a lubricious coating. When a metallic material is used, the body 194 may be a continuous coil made from either round or flat wire, or may be a hypotube having helical laser cuts directed toward the distal end of the body 194.

The magnet 196 is operable to attach the body 194 of the over-wire assembly 192 to the anchor magnet 152 at the plurality of struts 150. Thus, the magnet 196 is made of a material that is similar to the anchor magnet 152, described previously, but with an opposing magnetic polarity to facilitate coupling of the anchor magnet 152 to the magnet 196. The magnet 196 can be affixed to the distal end of the body 194 by welding, or glue, or other suitable means.

Further illustrated in FIG. 4A is a fiber capturing device 198 including a wire 199, a proximally positioned hub 200, and a distally positioned loop 202 for use in association with the over-wire assembly 192. In operation, the loop 202 can act as a needle for threading the fiber 148 through the body 194, but this method will be described in greater detail below. The wire 199 and loop 202 can be comprised of a wire material, similar to the materials of a standard snare device. The hub 200 can be any number of structures that provide a handle to the fiber capturing device 198 and to ensure that the proximal end of the fiber capturing device 198 does not enter the body 194. The wire 199 and loop 202 can be preloaded into the body 194 such that the loop 202 extends beyond the magnet 196 as illustrated.

Figure 4B:
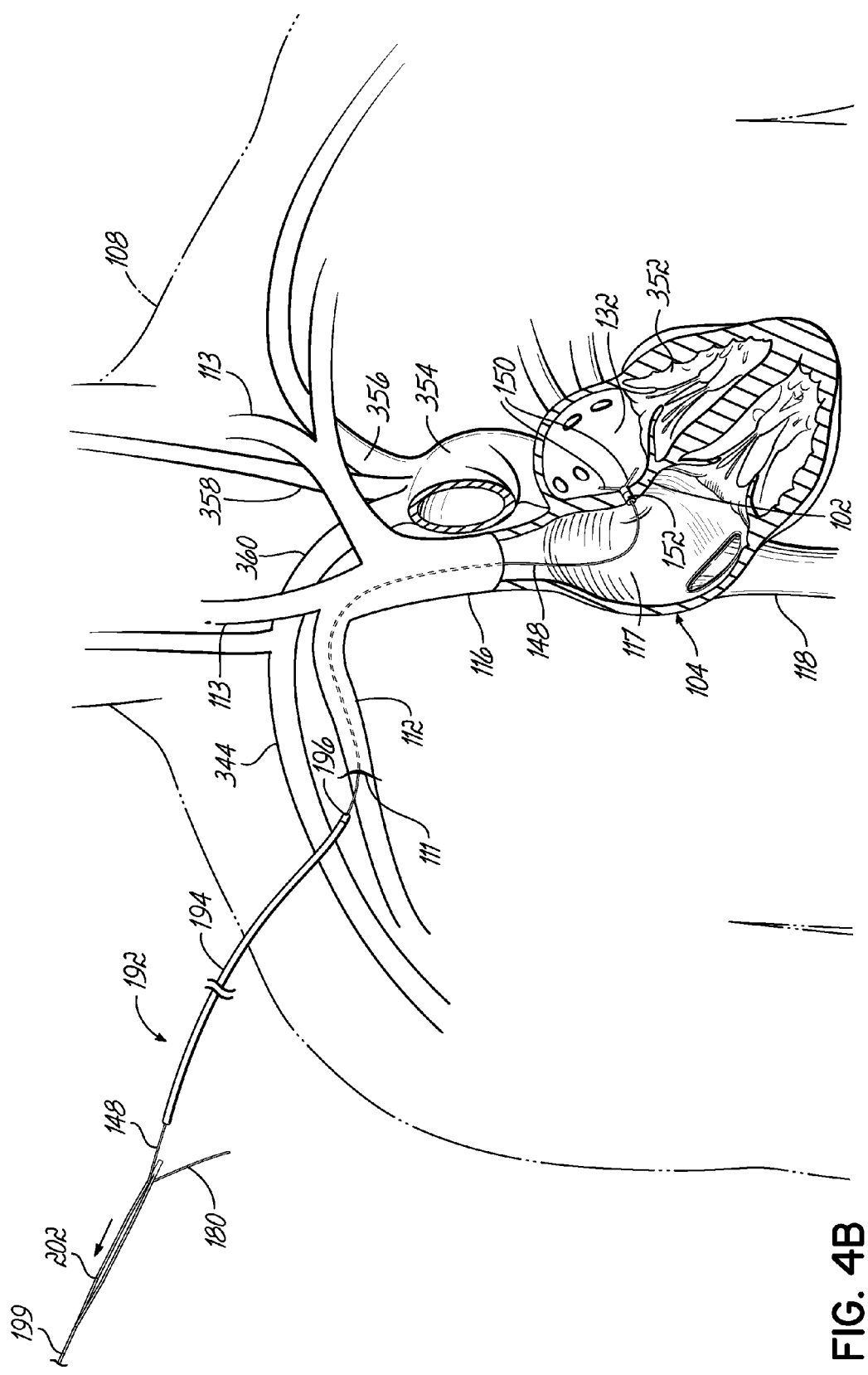

In operation and according to FIGS. 4A and 4B, the proximal end 180 of the fiber 148, while extending from the secondary incision site 182, is threaded through the loop 202 of the fiber capturing device 198. The hub 200 of the fiber capturing device 198 is then pulled away from the body 194, thereby pulling the loop 202, along with the fiber 148, through the lumen of the body 194, as shown in FIG. 4B. The fiber capturing device 198 is then fully removed from the body 194 such that the fiber 148 extends proximally from the body 194.

Figure 4C:
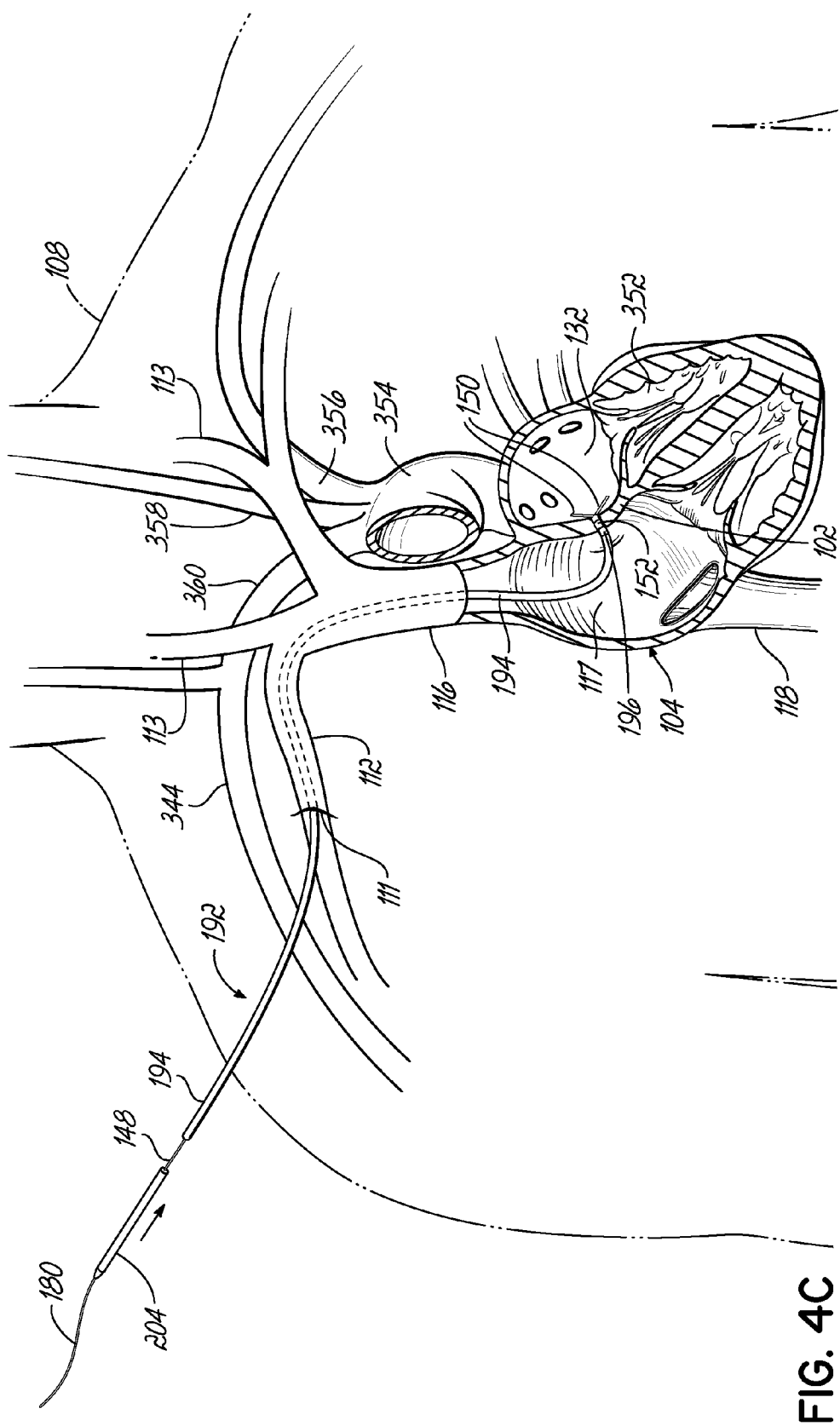

Continuing now to FIG. 4C, the body 194 can then be advanced over the fiber 148 while the surgeon maintains tension on the fiber 148 and the plurality of struts 150 within the left atrium 132. As the body 194 and the magnet 196 approach the intra-atrial septum 102, the magnet 196 and the anchor magnet 152 will magnetically couple to form a continuous platform that is stable for advancing additional devices to, and across, the over-wire assembly 192. In other embodiments, the anchor magnet 152 can further include a lead-in feature (not shown), which acts as a step for ensuring proper alignment and coupling of the anchor magnet 152 and the magnet 196.

To finalize the over-wire assembly 192 as illustrated in FIG. 4C, a one-way fiber clip 204 is directed over the proximal end 180 of the fiber 148 to prevent the proximal end 180 of the fiber 148 from reentering the body 194 of the over-wire assembly 192 and to ensure that tension is maintained between the anchor magnet 152 and the magnet 196, i.e. along the fiber 148. Once the fiber clip 204 contacts the body 194, the fiber clip 204 is clamped shut and the proximal end 180 of the fiber 148 extending proximally from the fiber clip 204 is trimmed.

Figure 4D:
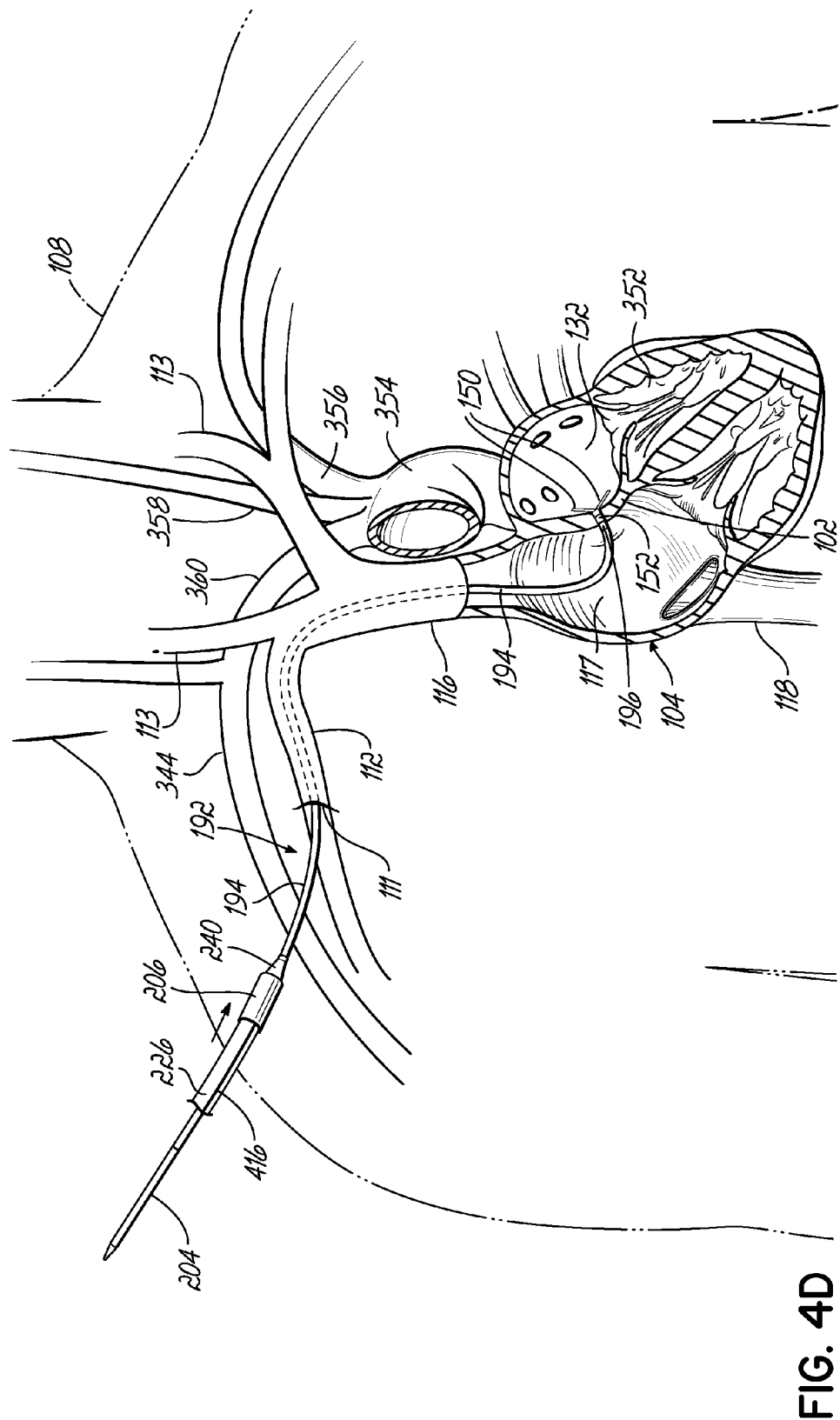

Then, as shown in FIG. 4D, the body 194 with the fiber clip 204 in place is ready to coaxially receive any suitable surgical apparatus. For example, a transseptal cannula apparatus is positioned coaxially over the fiber clip 204 and can follow the body 194 into the secondary incision site 182, down the right subclavian vein 112, the superior vena cava 116, and into the right atrium 117 of the heart 104.

While the method of directing the anchoring guide-element has been described and illustrated with some detail using a fiber, it would be readily understood that a wire could also be used. Likewise, while the method has been described and illustrated with some detail using the plurality of struts, it would be readily understood that a loop, double bend, or other anchoring portion could be deployed instead.

Though not specifically shown, it is possible for the surgeon to continue a surgical procedure from the primary incision site without transitioning the anchoring guide-element from the primary incision site to the secondary incision site. In this way, the snare device would not be used.

It is further possible for the surgeon to directly access the intra-atrial septum from a single incision site without creating the primary and secondary incision sites and utilizing the snare device. In this way, a single incision site is located substantially near the secondary incision site, which has been described above. The surgeon can direct a standard guidewire, obturator, and a steerable sheath into the single incision site. By using the steering wires of the steerable sheath, the surgeon can direct the assembly through the right subclavian vein, the superior vena cava, and into the right atrium. Upon reaching the right atrium, the surgeon directs the standard guidewire across the septum and into the left atrium.

Finally, in some situations the surgeon may desire exchanging the anchoring guide-element with a standard guidewire before proceeding in the surgery rather than using a reinforcement structure, such as the over-wire assembly. In that regard, the surgeon would therefore insert a sheath through the secondary incision site, down to the right atrium, across the septum, and into the left atrium. By pulling on the body portion of the anchoring guide-element while holding the sheath stationary, the surgeon can cause the anchoring portion to be contracted into the lumen of the sheath. Continued pulling of the body portion will retract the anchoring guide-element from the secondary incision site while the sheath is held in place within the left atrium. The surgeon may then insert a standard guidewire through the sheath and to the left atrium. After confirming that the guidewire is within the left atrium, the surgeon can retract the sheath from the secondary incision site.

Figure 5:
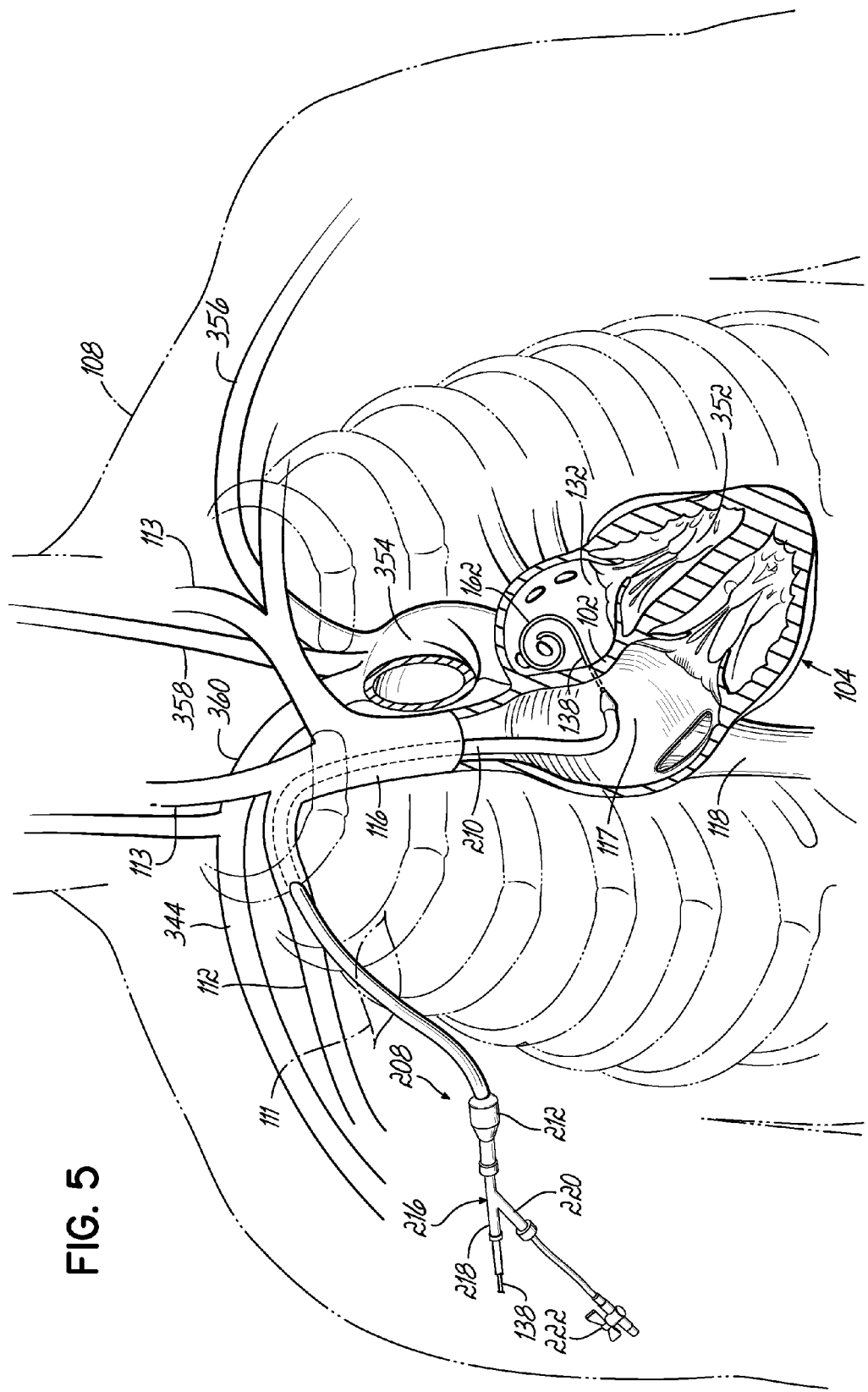
FIG. 5 is a diagrammatic view of an exemplary method of implanting the transseptal cannula assembly in a human heart, shown in cross-section.

After gaining access to the septum, the procedure for implanting a transseptal cannula assembly for the circulatory assist system can proceed in accordance with the method shown in FIG. 5 illustrating the anchoring guide-element as the loop 162 and wire 138. However, it would be understood that any of the anchoring guide-element embodiments described previously could be used.

As is shown in FIG. 5, a transseptal cannula assembly (not shown), by way of a delivery device 208, is loaded coaxially over the wire 138, into the secondary incision site 111, through the right subclavian vein 112, the superior vena cava 116, and into the right atrium 117. The delivery device 208 is operable to deliver the transseptal cannula assembly contained inside a delivery sheath 210, described in detail below, along the wire 138 and to the intra-atrial septum 102.

The delivery device 208 as shown in FIG. 5, and with greater detail in FIG. 6, includes the delivery sheath 210 and a hub 212 coupled with the proximal end of the delivery sheath 210. The delivery sheath 210 is preferably constructed as three thin-layer walls, though it is illustrated as a single-walled structure in FIG. 6. An exterior layer can be constructed of polyurethane, Nylon-11, Nylon-12, or PEBAX; an interior layer can be a liner made from an ePTFE, urethane, or Nylon with hydrogel coating; a mid-layer can be constructed from a braided material, such as stainless steel wire, Nitinol, or polyetheretherketones (PEEK) fibers to provide structural stability to the delivery sheath. The interior layer or an interior liner may be extruded and placed upon a mandrel with the mid-layer and the exterior layer respectively formed or otherwise placed over the interior layer. Polyurethane is then placed over the entire assembly and heat shrink wrapped over the tube for stability. Alternatively, the delivery sheath 210 can be laminated by a reflow process. In some instances, a superelastic coil 214 can be included around the delivery sheath 210 to increase the rigidity of the delivery sheath 210. Alternatively, a metallic braid (not shown) could be included around the delivery sheath 210. A polymeric layer 215 can surround the superelastic coil 214 to reduce friction as the delivery sheath 210 moves within the vascular network. It would also be permissible for the delivery device 208 to include a lubricious material, such as HYDROMED or a polyamide, to reduce friction as the transseptal cannula assembly moves within the delivery device 208.

The hub 212 is attached to the proximal end of the delivery sheath 210 by gluing, welding, or other means. The hub 212 generally includes a means for attaching to a Y-shaped connector 216. The Y-shaped connector 216 is operable for receiving other surgical instruments through a main port 218, such as a balloon catheter (see below), while preventing the back-flow of bodily fluid during the surgical procedure. A side port 220 permits limited fluidic access via a valve 222 (FIG. 5). Though not shown, the hub 212 can attach to any suitable hemostatic seal for preventing the back-flow of bodily fluid and should not be limited to the Y-shaped connector illustrated.

Continuing now to FIG. 6 for greater detail of the delivery device 208 and the transseptal cannula assembly 224, the delivery device 208 delivers the transseptal cannula assembly 224 across the intra-atrial septum for later operation with the circulatory assist system. The transseptal cannula assembly 224 includes a flexible cannula body 226, a tip 228 coupled to the distal portion of the flexible cannula body 226, and first and second anchors 230, 232 coupled to the tip 228. Each anchor 230, 232 is comprised of a plurality of struts 234. As illustrated, the second anchor 232 is further comprised of a porous polymeric structure 236 over the struts 234. The complete transseptal cannula assembly 224, once properly implanted, will create a shunt for oxygenated blood to flow from the left atrium of the heart to an implantable pump, and the vascular network beyond.

In constructing the transseptal cannula assembly 224, the walls of the flexible cannula body 226 are preferably designed from a biodurable, low durometer thermoplastic or thermoset elastomer material. Specifically, this may include an extruded aliphatic, polycarbonate based polyurethane; aliphatic polyether polyurethane; aromatic polyether polyurethane; aromatic polycarbonate based polyurethane; silicone modified polyurethane; or silicone. Antimicrobial agents may be embedded within the flexible cannula body material prior to the forming process to effectively reduce or eliminate the presence of bio-film and reduce the potential for infection. Alternatively, the antimicrobial agent may be applied to the surface of the flexible cannula body 226 after the molding process is complete. Further, the flexible cannula body 226 can be constructed as multiple layers, though this is not specifically shown.

Once the flexible cannula body 226 is properly formed, it is cut to the desired length. The proximal and distal portions 227, 229 can be formed to be about twice the thickness of the remainder of the flexible cannula body 226, which can assist in coupling the flexible cannula body 226 to the pump of the circulatory assist device and the tip 228, respectively. Other thicknesses for the proximal and distal portions can also be used and are limited to the inner diameter of the delivery sheath 210. The thicker proximal portion 227 of the flexible cannula body 226 can further aid in closing the space between the flexible cannula body 226 and the delivery sheath 210 so that when a balloon catheter is back-loaded, the balloon catheter cannot move to the space between the delivery sheath 210 and the flexible cannula body 226. Alternatively, the proximal and distal portions 227, 229 can be flared for coupling the flexible cannula body 226 to a pump of the circulatory assist device and the tip 228, respectively.

In some embodiments, a lubricious coating or layer can be included on the exterior of the flexible cannula body 226. Such a lubricious layer would aid in the movement of the flexible cannula body 226 with respect to a delivery device 208. Suitable materials for the layer can include ePTFE, fluorinated ethylene propylene (FEP), ethylene vinyl acetate (EVA), polyvinylidene difluoride (PVDF), high density polyethylene (HDPE), PEBAX, or polyamide materials coated with a lubricious coating similar to HYDROMED.

Referring again to FIG. 6, a balloon catheter 238 is illustrated for use in conjunction with the delivery device 208 when implanting the transseptal cannula assembly 224. The balloon catheter 238 for use in this method would include a balloon 240 constructed of a compliant to non-compliant material, including Nylon-11, Nylon-12, polyurethane, polybutylene terephthalate (PBT), PEBAX, or polyethylene terephthalate (PET). The balloon 240 is coupled to the distal portion of a catheter shaft 242, which can be constructed of the same or a different material as the balloon 240. Coupling of the balloon 240 to the catheter shaft 242 can be by thermal bonding, adhesives, solvent, or covalent bonding. A Y-connector valve 244 can be included upon the proximal portion of the catheter shaft 242 with a strain relief 246 for transitioning between the rigid Y-connector valve 244 to the flexible catheter shaft 242. The Y-connector valve 244 can include a main port 248 and a side port 250, wherein the side port 250 can include a stop cock (not shown) for inflating or deflating the balloon 240. A marker band 251 can be included upon the distal end of the catheter shaft 242 for providing in vivo location and alignment of the balloon 240.

In some embodiments, such as the alternate cross-section shown in FIG. 6A, the balloon catheter shaft 242a can further include at least one lumen 252 containing at least one steering wire 253 for steering the balloon 240. The at least one steering wire 253 will extend from a distal end point (not shown) within the balloon 240 (FIG. 6) through the lumen 252 and to a steering mechanism (not shown) that is attached to the y-connector valve 244. The steering mechanism will include a slide (not shown) operable for pulling on the steering wire and thereby cause the distal end of the balloon 240 to be laterally deflected. Once released, the balloon 240 will return to the undeflected position. The balloon catheter 238 will also include an inflation lumen 255 for passing a fluid for inflating or deflating the balloon 240.

Turning now to FIG. 7A, the tip 228 of the transseptal cannula assembly is illustrated and described with greater detail. Generally, the tip 228 includes a proximal portion 228a, a medial portion 228b, and a distal portion 228c. An opening 254 extends through the proximal, medial, and distal portions 228a-c and provides fluidic communication between the left atrium and the flexible cannula body 226 (FIG. 6). In a preferred embodiment, the proximal, medial, and distal portions 228a-c are constructed from titanium alloy, such as TiAl 6Va EL 1, by standard turning, wire electrical discharge machining (EDM), or other machining processes.

As further shown in FIG. 7A, the distal portion 228c of the tip 228 can include a shape that will reduce fluidic drag, but the tip 228 should not be considered to be limited to the shape specifically shown. Likewise, the proximal portion 228a may be shaped according to fluidic needs and the means of coupling the flexible cannula body to the tip 228.

Continuing with FIGS. 7A and 7B, the tip 228 can further include one or more rings 256, provided for several reasons. These rings 256 may act in a manner as to engage the anchors 230, 232 (see FIG. 7B). In this way, rings 256 may act in conjunction with clamps 258 (FIG. 7B) to affix the anchors 230, 232 upon the tip 228. Further, the rings could be used to seat the anchors 230, 232 and can be keyed in a way so as to maintain an orientation of the anchor. Suitable clamps 258 may include configurations as shown or others such as, but not limited to, swage or crimp-style clamps. The clamps 258 could alternately be attached to the tip 228 by an adhesive, welding, or tying. The tip 228 may further include one or more barbs 260 upon the proximal end 228a of the tip 228. Barbs 260 provide resistance against the undesired removal of the flexible cannula body 226 (FIG. 6) from the tip 228.

In construction, the rings 256 and barbs 260 can advantageously be molded as a portion of the tip 228. Alternatively, the rings 256 are swaged or crimped into place after the tip 228 is constructed. In some embodiments, the rings 256 may optionally be constructed of radiopaque materials such as to aid in localization of the transseptal cannula assembly 224 (FIG. 6). Alternatively, a separate radiopaque band (not shown) may be constructed and placed sufficiently near the rings 256.

Turning now to FIGS. 8A-8E, the details of the anchors 230, 232 of the transseptal cannula assembly are explained with greater detail. Specifically shown in FIG. 8A, each anchor 230, 232 includes a plurality of struts 234 extending from a central ring portion 262. The plurality of struts 234 and central ring portion 262 may be etched as a single unit from the same piece of superelastic material to form internal support structure for each of the anchors 230, 232. Alternatively, it would be possible to permanently affix each strut 234 to a separately manufactured central ring portion 262, such as by welding or other means. It should be appreciated that while four struts 234 are shown per anchor 230, 232, this number is not so limited. Rather, embodiments could be envisioned where fewer or more struts 234 may be necessitated or desired for a particular surgeon's needs or preference. Providing at least three struts can result in greater stability of the implanted tip 228 (FIG. 7B).

The struts 234 and ring portion 262 can be at least partially constructed from a superelastic NiTi material by chemically etching the parts from flat sheet stock, electropolishing the etched parts to remove rough edges generated during the formation process, and then heating the parts to a superelastic state. While the preferred materials are specifically taught herein, other suitable biocompatible, non-compliant, flexible material would be sufficient for the tip or the anchors.

Figure 8A:
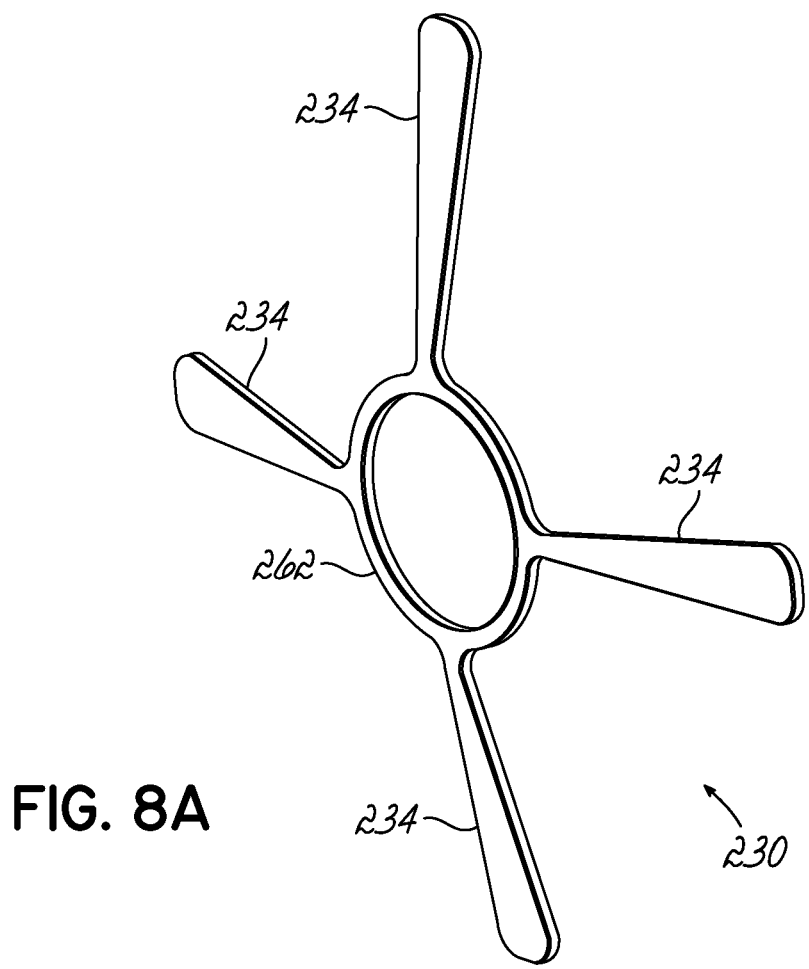
FIG. 8A is a perspective view of one embodiment of an anchor used in conjunction with tip shown in FIG. 7A.
Figure 8C:
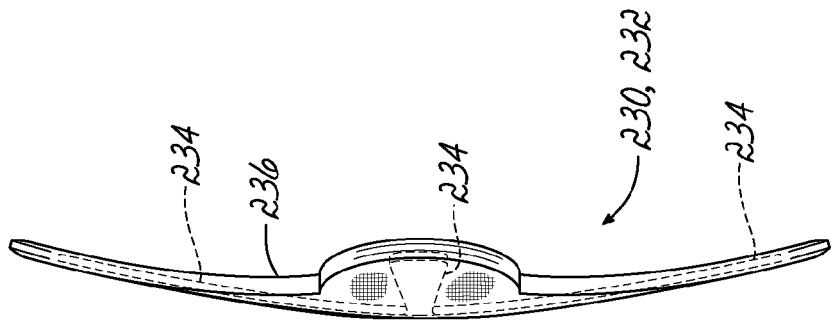
FIG. 8C is a side elevation view of the anchor illustrated in FIG. 8B.
Figure 8B:
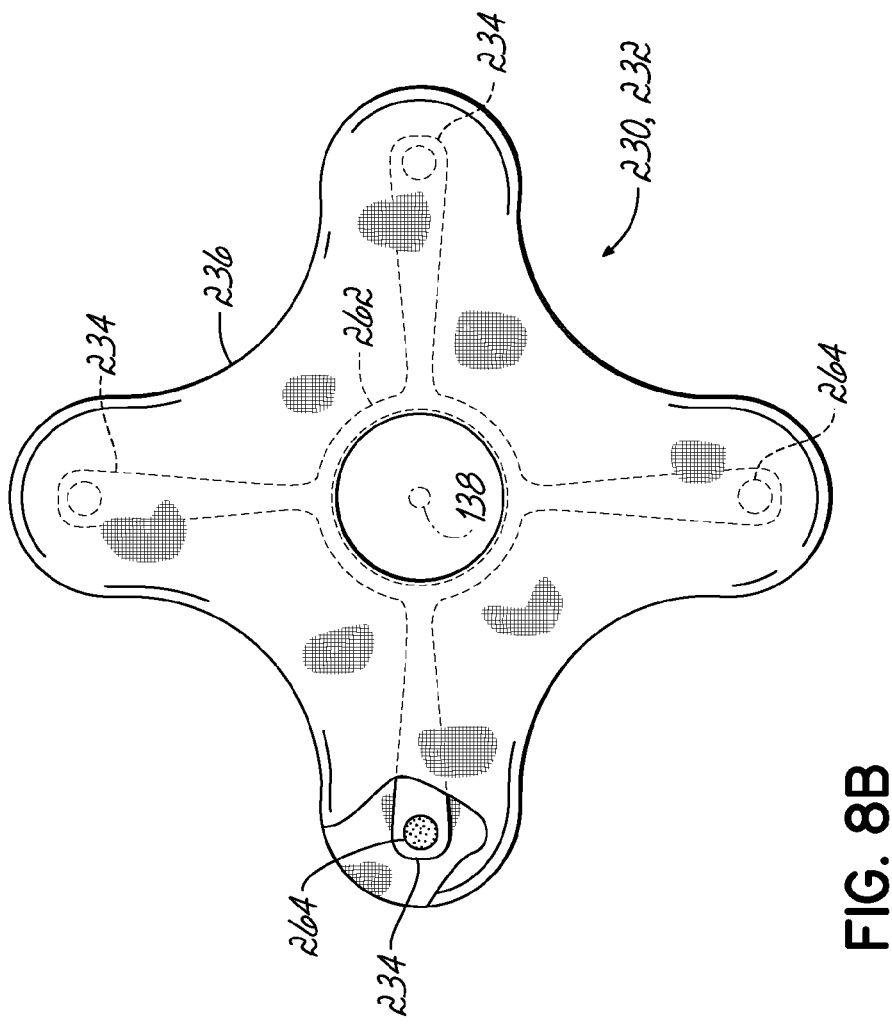
FIG. 8B is a front elevation view of another embodiment of the anchor partially cut away.

FIG. 8B illustrates, with some detail, the anchors 230, 232 further including the porous polymeric structure 236. In function, the porous polymeric structure 236 provides a larger surface to engage the septum (not shown) than the plurality of struts 234 alone. Further, the porous polymeric structure 236 allows for tissue in-growth, wherein tissue from the septum may grow and embed within the porous polymeric structure 236 to provide greater structural stability and sealing capacity. While either or both of the anchors 230, 232 can include the porous polymeric structure 236, it is generally preferred that only the second anchor 232, which will reside along the septum (not shown) within the right atrium (not shown), will include the porous polymeric structure 236. This configuration is preferred because the right atrium is larger in volume than the left atrium; however, the invention should not be considered so limited.

Suitable materials for the porous polymeric structure 236 may include, but are not limited to, polyester monofilament or multifilament yarn; ePTFE monofilament or multifilament yarn; or fluorinated polyolefin fibers or yarns, which can be woven, braided, knitted, or felted into a proper configuration. The porous polymeric structure 236 may further include various intrinsic configurations including weaves, braids, or knits having two or three-dimensional honeycombs, circular, flat, or tri-axial tubular structures. In other embodiments, the porous polymeric structure 236 may be constructed from an ePTFE piece in tubular, cylindrical, or sheet form. Generally, the porous polymeric structure 236 will be constructed by etching or laser cutting a shape from two sheets of a stock material (such as those described above). The shaped polymeric structures 236 are then ultrasonically welded together such that the shaped polymeric structures capture the anchor therebetween.

As is further shown in FIG. 8B, each strut 234 can include a marker 264. The marker 264 can be constructed from a fluoroscopic paint such that the location of the anchor 230, 232 is visible by intracardiac echocardiography. In this way, the marker 264 enables the surgeon to differentiate between an anchor 230, 232 that is parallel to the lengthwise central axis, represented by the wire 138, from one that is transverse to the same axis. Thus, the surgeon is capable of determining the state of deployment of the first and second anchors 230, 232, in vivo. Other suitable materials for the marker 264 may include radiopaque or similar materials.

FIG. 8C shows the deployed anchors 230, 232 in a side elevation view. The plurality of struts 234 cause the anchors 230, 232 to have a slight concave curvature. Because the actual size, shape, and structure of the heart and intra-atrial septum may change from patient-to-patient, this slight concave curve, which is directed toward the septum, permits a single transseptal cannula assembly design to be adaptable to a wide range of anatomies. Additionally, the slight curve provides a greater elastic clamping action against the septum.

Figure 8D:
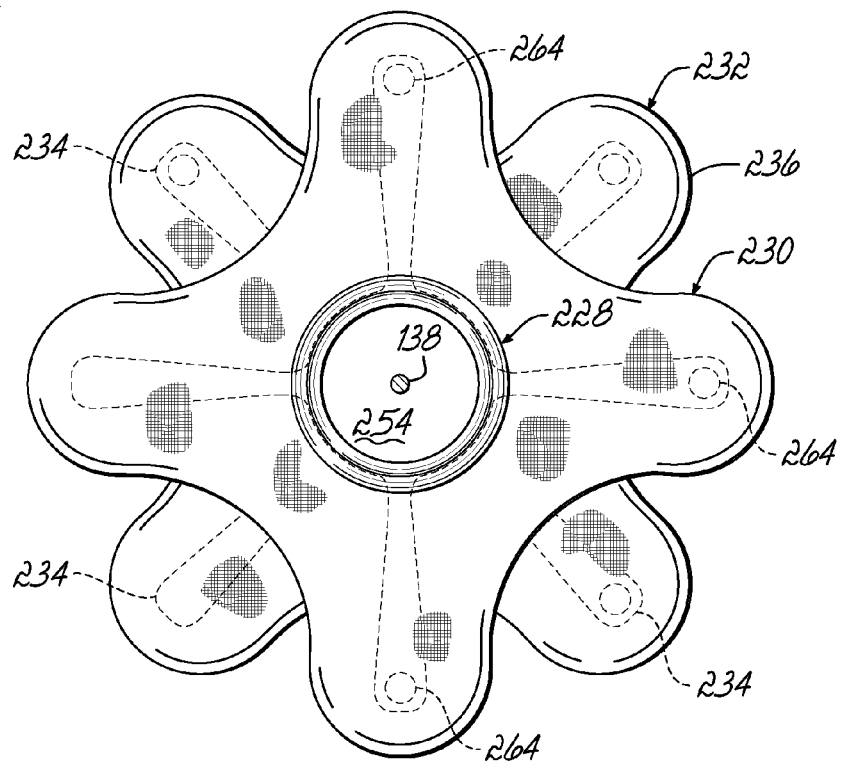
FIG. 8D is a front elevation view of the first and second anchors shown in the deployed state and mounted on the cannula tip of FIG. 7A.
Figure 8E:
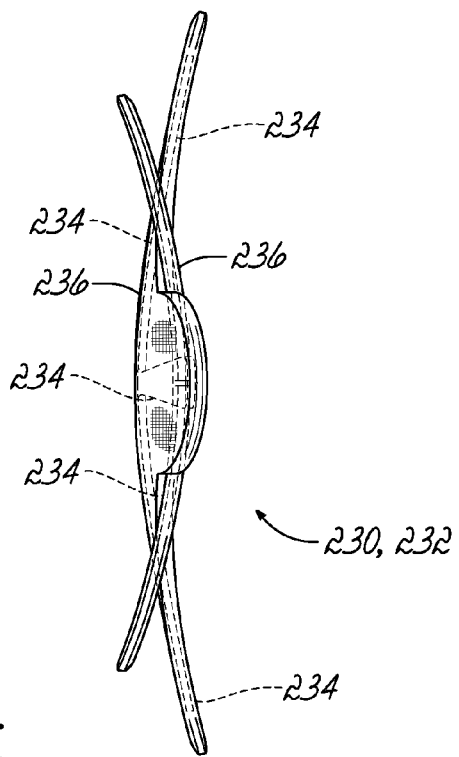
FIG. 8E is a side elevation view of the first and second anchors shown in the deployed state without the septum shown, taken along line 8E-8E of FIG. 8D.

FIGS. 8D-8E illustrate that the anchors 230, 232 can be positioned such that the first anchor 230 is offset with respect to the second anchor 232. This is the preferred configuration of the deployed anchors 230, 232 because of the particular load-bearing benefits. However, it would also be possible to include anchors with no offset if the particular need would arise. Additionally, it is possible to construct the anchors 230, 232 in a way such that the second anchor 232 is larger than the first anchor 230 to provide larger surface contact area, as is shown in FIG. 8E. This configuration is more desirable than the reverse because the right atrium is larger in volume than the left atrium; however, the invention should not be considered so limited. For example, in some embodiments, it may be preferred to include only the first anchor 230 on the tip 228. In this embodiment, the first anchor could include the porous polymeric structure 236, or could remain bare.

As shown in FIG. 8E, the slight concave curve can cause the first and second anchors 230, 232 to cross in their freestanding deployed state when mounted upon the tip 228 (FIG. 6).

Because the anchors are transverse to the lengthwise central axis in the natural state, it is necessary to fold the anchors to a position that is generally parallel to the lengthwise central axis and suitable for loading the anchors into the delivery sheath.

Figure 9A:
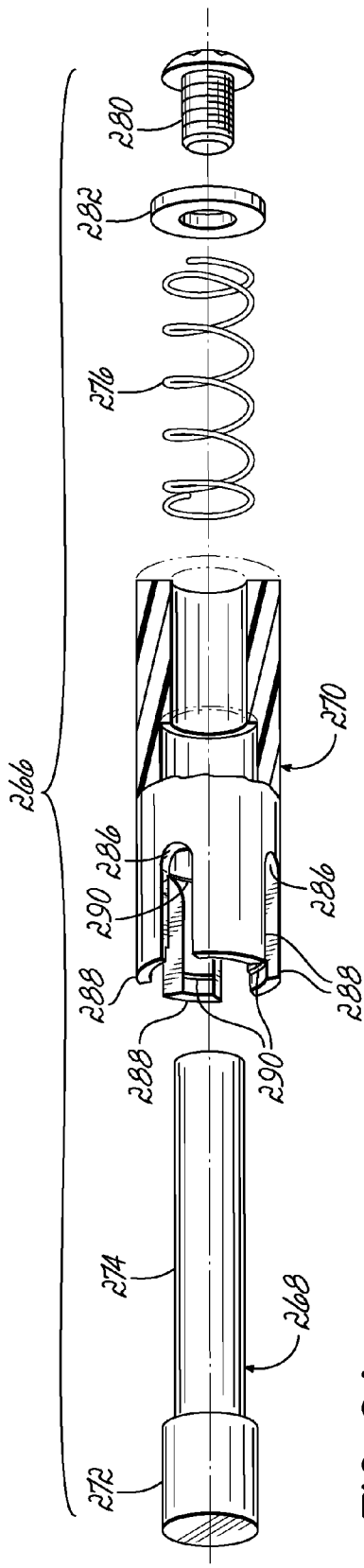
FIG. 9A is a disassembled perspective view of the distal loading apparatus in partial cross-section.
Figure 9B:
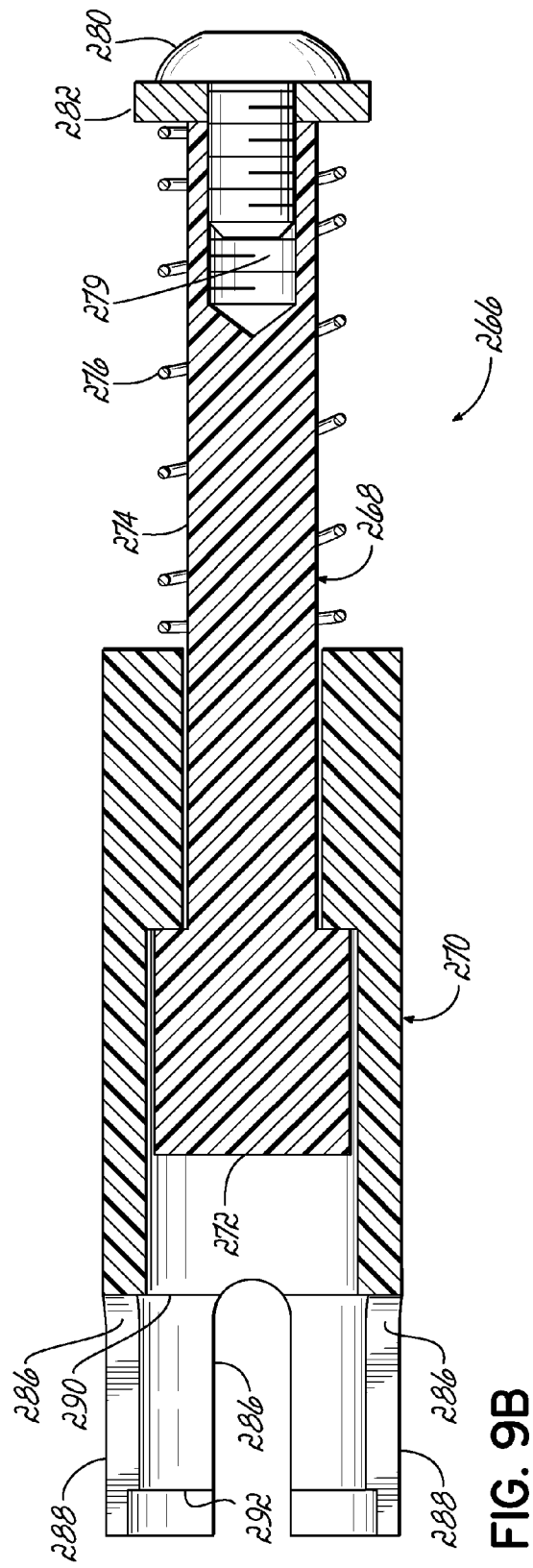
FIG. 9B is an assembled cross-sectional view of the distal loading apparatus of FIG. 9A, in partial cross-section.

FIGS. 9A and 9B illustrate a cannula loading device 266 for loading the transseptal cannula assembly 224 into the delivery device 208 as shown in FIG. 6. The cannula loading device 266 includes a plunger 268 within a plunger housing 270. The plunger 268 includes large and small diameter portions 272, 274. The small diameter portion 274 receives a spring 276. The proximal end of the plunger 268 can include internal screw threads 279 (FIG. 9B) for receiving a screw 280 and washer 282 and thus maintain the spring 276 on the small diameter portion 274.

FIGS. 9A-9B and 10A-10D illustrate a distal end of the plunger housing 270 including a plurality of slots 286 and a plurality of fingers 288. The number of slots 286 corresponds with the number of struts 234 of the first anchor 230; the number of fingers 288 corresponds with the number of struts 234 of the second anchor 232. The plunger housing 270 further includes interiorly located first and second steps 290, 292, wherein the first step 290 is located proximal to the second step 292.

Figure 10A:
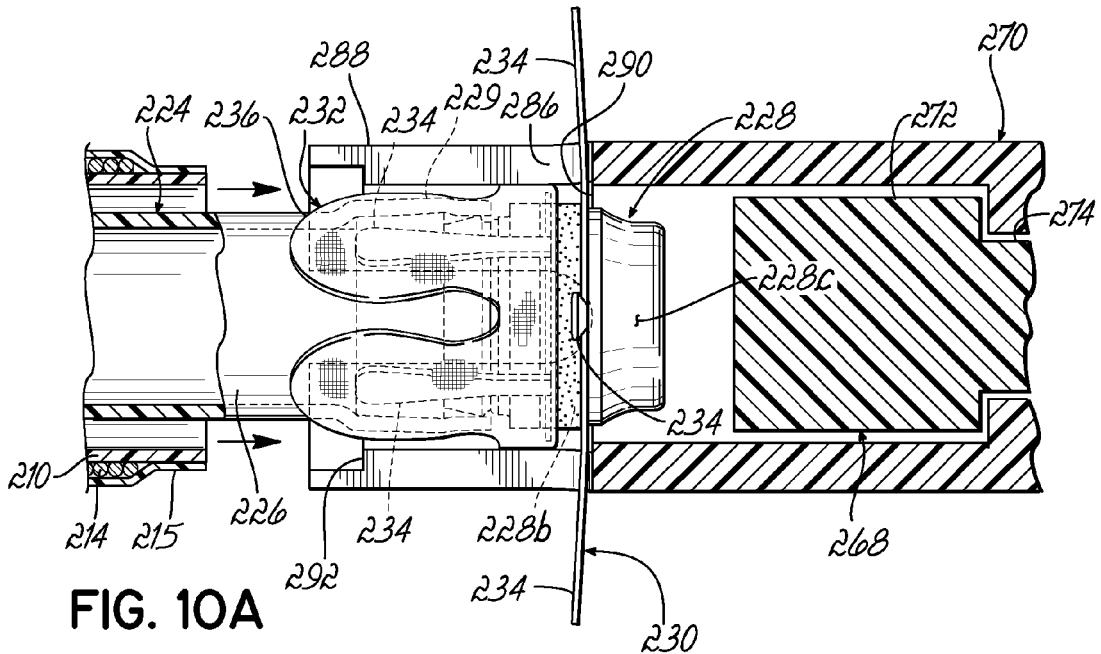
FIGS. 10A through 10D illustrate the transseptal cannula assembly being loaded into the delivery apparatus by the distal loading apparatus, shown in partial cross-section.

In operation, and as illustrated in FIGS. 10A-10D, the transseptal cannula assembly 224, leading with the tip 228, is inserted into the distal end 284 of the plunger housing 270 such that the struts 234 of the first anchor 230, align with the plurality of slots 286 and thereby remain in a deployed state as shown in FIG. 10A. As the tip 228 is positioned further within the plunger housing 270, each strut 234 of the second anchor 232 will align with each of the plurality of fingers 288 and the corresponding second step 292, thereby causing each strut 234 of the second anchor 232 to collapse into a contracted state that is smaller in diameter than the inner diameter of the delivery sheath 210.

From FIGS. 9A-9B and 10A-10D, it will be understood that the relative positions of the first and second steps 290, 292 can aid in determining the depth at which the transseptal cannula assembly 224 will be inserted within the delivery sheath 210. For example, if the second step 292 is positioned close to the first step 290, then a larger portion of the delivery sheath 210 will be inserted over the second anchor 232. The opposite would also be true. Thus, upon depressing the plunger 268, the transseptal cannula assembly 224 will be positioned further within the delivery sheath 210.

Figure 10B:
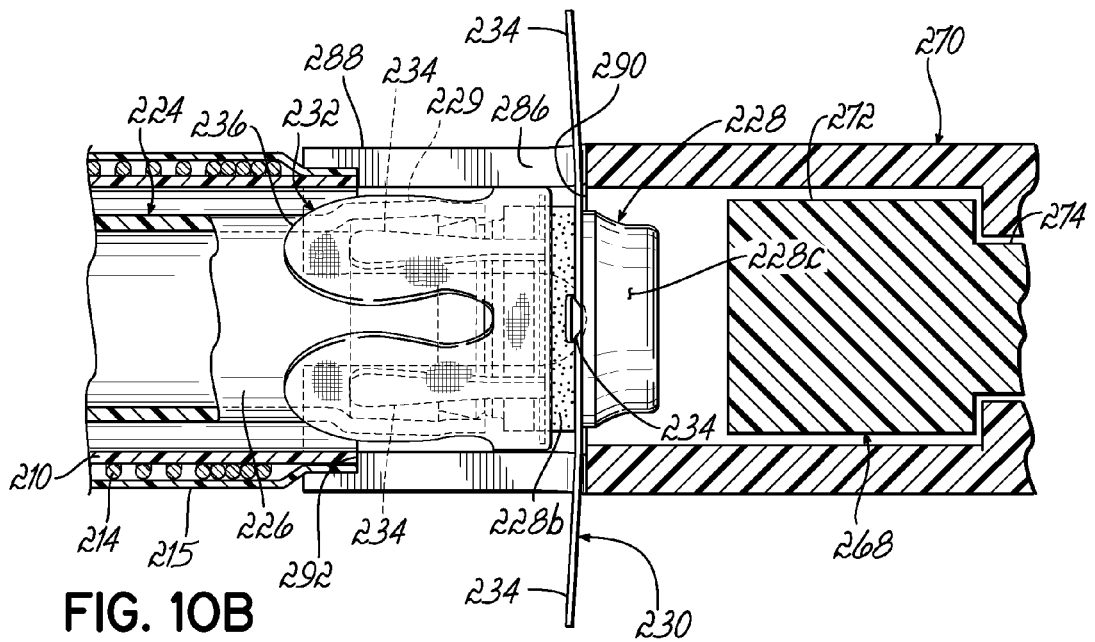

Referring specifically now to FIGS. 10A and 10B, once the tip 228 of the transseptal cannula assembly 224 is fully inserted within the plunger housing 270 (i.e. the first anchor 230 contacts the first step 290) and the flexible cannula body 226 extends distally from the cannula loading device 266, the delivery sheath 210 can be directed over the flexible cannula body 226 and up to the second step 292. Because the second anchor 232 is deflected (as shown) to a diameter that is smaller than the inner diameter of the delivery sheath 210, the delivery sheath 210 can pass between the second anchor 232 and the plurality of fingers 288 to make contact with the second step 292.

Figure 10C:
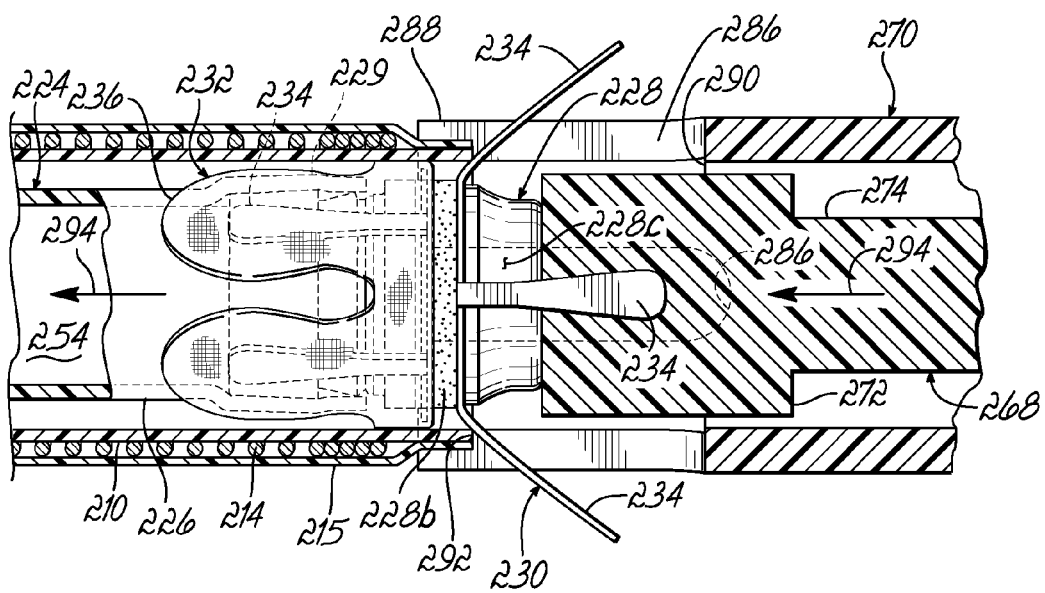
Figure 10D:
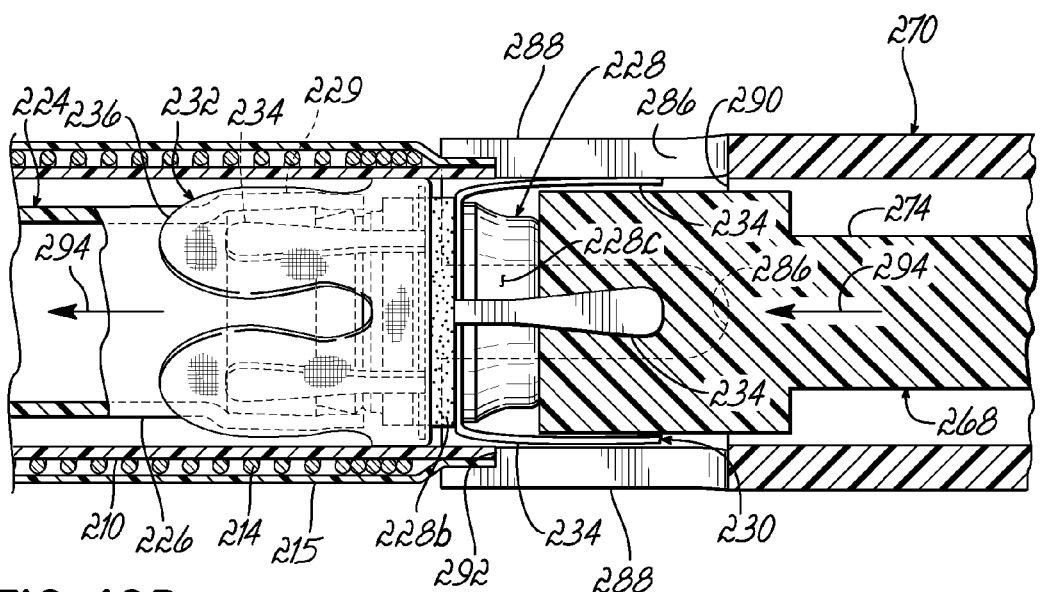

FIGS. 10C-10D, illustrate loading of the transseptal cannula assembly 224 into the delivery sheath 210 by transferring the tip 228 from the cannula loading device 266 to the delivery sheath 210. The surgeon then presses against the screw 280 (FIG. 9B) of the proximal end 278 (FIG. 9B) of the plunger 268, thereby depressing the spring 276 (FIG. 9B) and advancing the large diameter portion 272 of the plunger 268 in the direction of arrow 294. After the plunger 268 makes contact with the tip 228, further pressing of the plunger 268 in the direction of arrow 294 will cause the second anchor 232 to enter the delivery sheath 210 as shown in FIG. 10C. Further movement of the plunger 268 will cause the tip 228 to enter the delivery sheath 210 and initiate folding of the first anchor 230 as in FIG. 10D.

Once the plunger 268 has reached the end of its stroke, the transseptal cannula assembly 224 will be loaded within the delivery sheath 210 such that the second anchor 232 is deflected and extends proximally while the first anchor 230 is deflected and extends distally. When the spring 276 (FIG. 9B) is released, the plunger 268 will return to a rest position and the cannula loading device 266 is removed from the transseptal cannula assembly 224 and the delivery sheath 210.

Figure 11A:
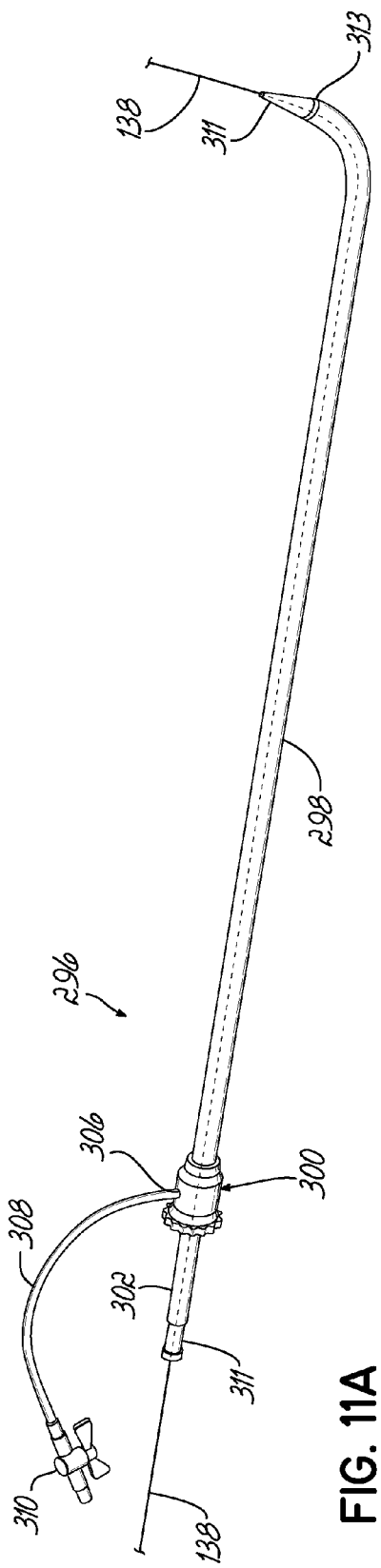
FIG. 11A is a perspective view of an alternate embodiment of the delivery device.

FIG. 11A illustrates an alternate delivery device 296 for use with a transseptal cannula assembly. The delivery device 296 includes a delivery sheath 298 and a proximally located hub 300, such as a hemostasis valve. The hub 300 can further include a side port 306 having a tube 308 and a valve 310 for fluidic access. A removable loading tube 302 is pressed into the proximal end of the hub 300 to open the hemostasis valve and allow an obturator 311 to extend through the delivery sheath 298 for dilating the opening within the intra-atrial septum created by the wire 138. The obturator 311 and loading tube 302 are removed before loading the transseptal cannula assembly (not shown). Finally, a distally located marker band 313 can be used for localization, in vivo.

Figure 11B:
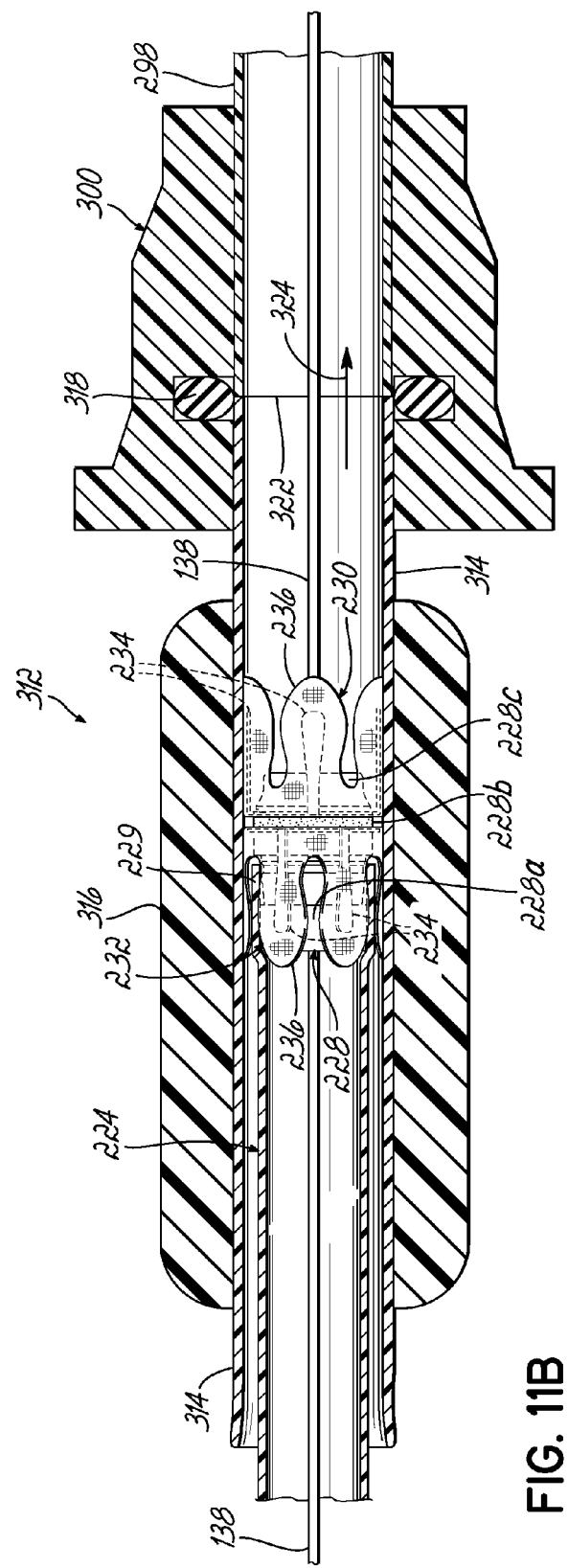
FIG. 11B is a longitudinal cross-sectional view of a portion of the delivery device illustrated in FIG. 11A showing the loading of a transseptal cannula assembly.

FIG. 11B illustrates the use of a proximal loading device 312 for loading of the transseptal cannula assembly 224 into the delivery device 296. The proximal loading device 312 includes a tube structure 314, preferably constructed from ePTFE or FEP, and a handle 316 constructed of a stiff material to assist the surgeon in manipulating and docking the proximal loading device 312 with the delivery device. Suitable materials for the handle 316 can include acrylonitrile butadiene styrene (ABS) or a polycarbonate. While not specifically shown in FIG. 11B, the handle 316 may include a bonding ring proximate to and circumferentially surrounding the tube structure 314 and an access port for injecting an adhesive suitable for coupling the handle 316 to the tube structure 314. Alternative manners of adjoining the handle 316 and tube structure 314 may also be used.

Continuing with FIG. 11B, the surgeon has docked the proximal loading device 312 with the delivery sheath 298 (FIG. 11A) at the hub 300. The hub 300 includes an O-ring 318 as part of the hemostasis valve capable of forming a fluid tight seal around the delivery sheath 298. A transition point 322 between the tube structure 314 of the proximal loading device 312 and the delivery sheath 298 should be made substantially without interruption such that the transseptal cannula assembly 224 moves smoothly and freely from the proximal loading device 312 and into the delivery device. Transfer of the transseptal cannula assembly 224 to the delivery device can then be accomplished by pushing the flexible cannula body 226 in a distal direction, shown with arrow 324.

Turning now to FIGS. 12A-12D, once the transseptal cannula assembly 224 has been loaded into the delivery sheath 298, the surgeon back-loads the balloon catheter 238 through the proximal portion of the transseptal cannula assembly 224. The balloon catheter 238 is then positioned within the tip 228 such that the marker band 251 aligns with the distal end of the delivery sheath 298. The balloon 240 is then inflated with a fluid (FIG. 12A), which is typically saline with or without a contrast agent. When fully inflated, the distal end of the balloon 240 expands radially beyond the first anchor 230 and engages the inner diameter of the delivery sheath 210 and the inner diameter of the tip 228, thereby securing the tip 228 and the delivery sheath 210.

The balloon catheter 238, the transseptal cannula assembly 224, and the delivery device 208, as a unit, are then positioned over the proximal end (not shown) of the wire 138 and advanced into the secondary incision site 182 (FIG. 5). The delivery device 208, with the transseptal cannula assembly 224 and balloon catheter 238 will follow the wire 138 through the right subclavian 112 (FIG. 5), the superior vena cava 116 (FIG. 5), and into the right atrium 117 (FIG. 5).

Figure 12A:
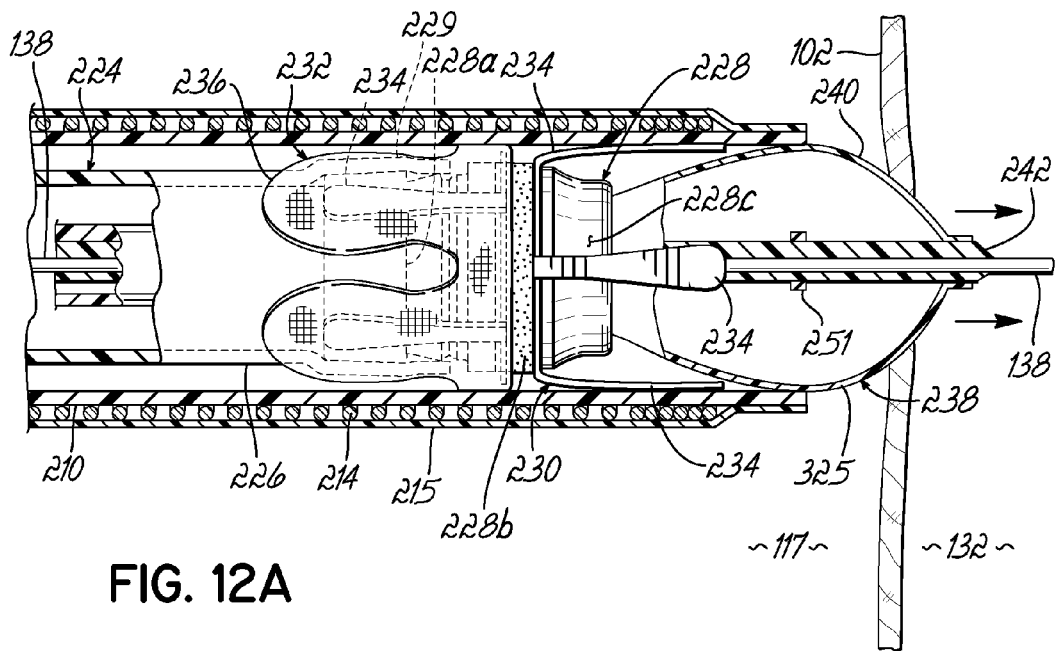
FIGS. 12A through 12D are side elevational views in partial cross section of an exemplary method of deploying the anchors of the transseptal cannula assembly.

As shown in FIG. 12A, once the delivery device 208 and the transseptal cannula assembly 224 are within the right atrium 117, the surgeon can advance the delivery device 208 with the transseptal cannula assembly 224 and balloon catheter 238, as a unit, over the wire 138 such that a proximal cone 325 of the inflated balloon 240 dilates the opening created by the wire 138 through the intra-atrial septum 102.

Figure 12B:
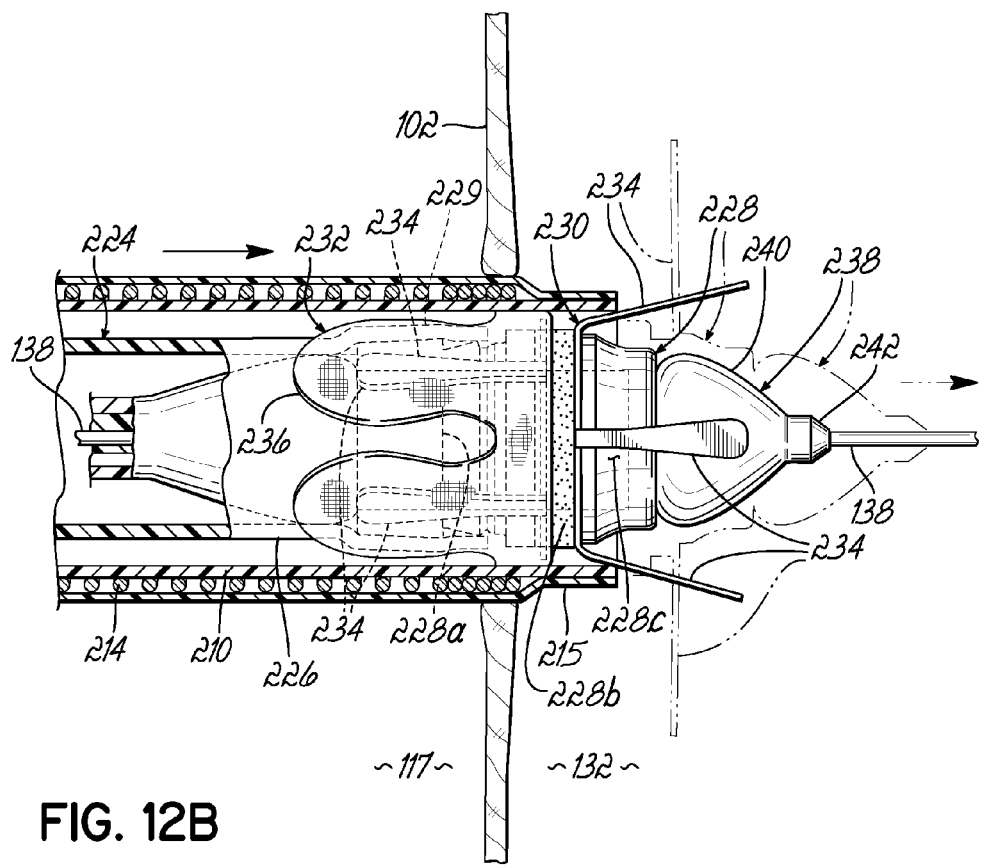

Continuing now to FIG. 12B, where the opening through the intra-atrial septum 102 has been dilated and the delivery device 208 has been advanced in the direction of arrow through the dilated opening through the intra-atrial septum 102. Thus, the balloon 240, the first anchor 230, and the distal end 228c of the tip 228 reside within the left atrium 132. The surgeon then deflates the balloon 240 and realigns balloon 240 with the tip 228 by aligning the marker band 251 (FIG. 12A) with markers (not shown) on the tip 228. The balloon 240 is then re-inflated to engage the inner diameter of the tip 228 while permitting relative movement between the tip 228 and the delivery sheath 210.

In FIG. 12B, the surgeon advances the balloon catheter 238, with the tip 228 beyond the delivery sheath 210, such that the first anchor 230 is moved beyond the delivery sheath 210 and into the left atrium 132. In this way, the first anchor 230 is deployed (spring outward) from the contracted state (in phantom) to the deployed state (in solid), within the left atrium 132. The second anchor 232 remains in the contracted state and within the delivery sheath 210. The balloon catheter 238 can then be retracted, thereby retracting the tip 228 and such that the first anchor 230 contacts the intra-atrial septum 102.

Figure 12C:
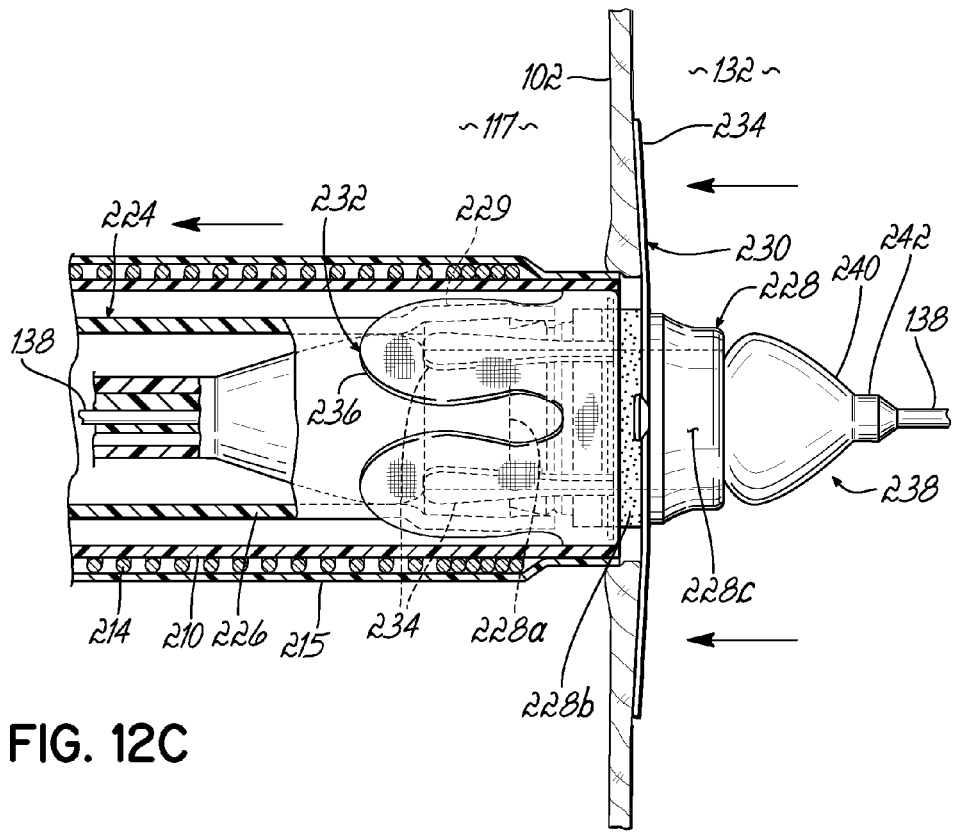

FIG. 12C illustrates the retraction of the balloon catheter 238 along with the tip 228 and the delivery sheath 210 until the deployed first anchor 230 contacts the intra-atrial septum 102 within the left atrium 132.

Figure 12D:
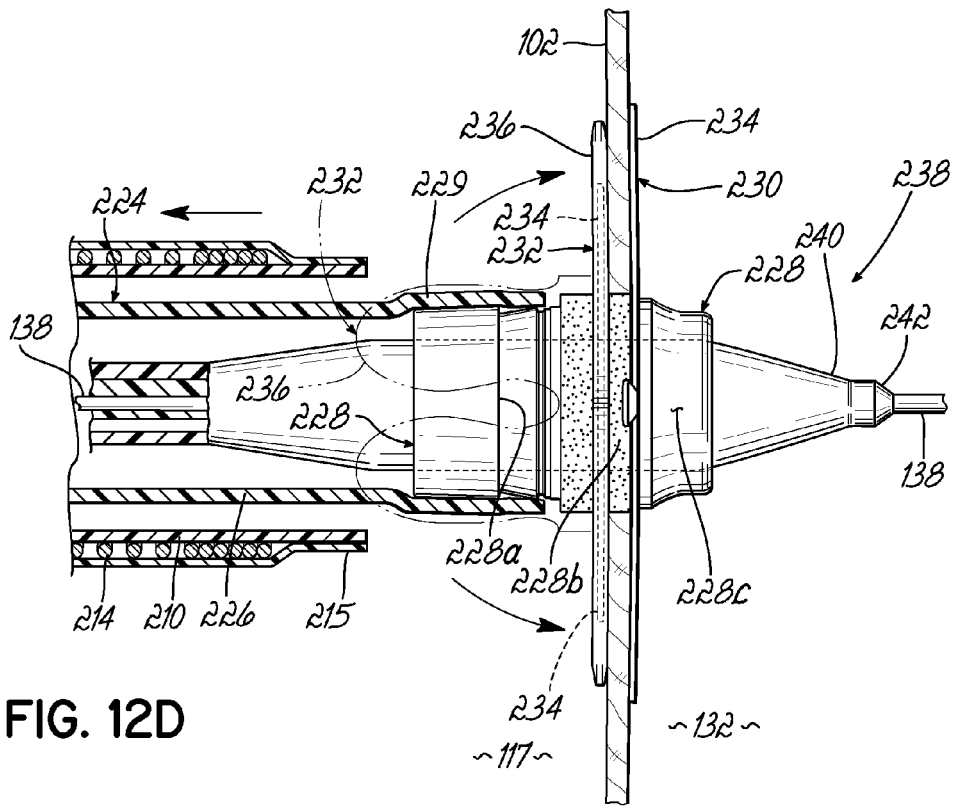

Finally, as shown in FIG. 12D, the surgeon continues to retract the delivery sheath 210 in the direction of the arrow while the balloon catheter 238 and tip 228 are maintained in position. This deploys the second anchor 232 in a manner similar to the first anchor 230, from a contracted position, shown in solid in FIGS. 12A-12C and in phantom in FIG. 12D, to an expanded position, shown in solid in FIG. 12D. This deployed second anchor 232 engages the intra-atrial septum 102 within the right atrium 117. Together, the first and second anchors 230, 232 will prevent movement of the tip from the intra-atrial septum 102.

Now that the tip 228 and the anchors 230, 232 are implanted on opposite sides of the intra-atrial septum 102, the delivery sheath 210 can then be removed from the secondary incision site 182 (FIG. 5). The balloon 240 is again deflated and the balloon catheter 238 removed from the secondary incision site 182 (FIG. 5). Finally, the anchoring guide-element is removed by retracting the wire 138 while maintaining the position of the transseptal cannula assembly 224, thereby causing the loop 162 (FIG. 5) or other anchoring portion to collapse and enter the transseptal cannula assembly 224 in a manner that has been described previously. After the anchoring guide-element has been fully removed, only the transseptal cannula assembly 224 remains in place.

In an alternate method of implanting the transseptal cannula assembly, which is not shown in the drawings, the opening through the intra-atrial septum is pre-dilated with a removable obturator or a balloon catheter that expands to a diameter that is approximately equal to the outer diameter of the delivery sheath. A suitable removable obturator may comprise a rod and an expanded portion upon the distal end of the obturator. While the obturator is preferably constructed from Nylon-11, Nylon-12, or PEBAX, other suitable materials are also appropriate. The rod can include a marker band near the expanded portion and aligned with the delivery sheath. The marker band can be made from any material that would enable a surgeon to remotely determine the location of the distal end of the delivery sheath within the heart. The surgeon can advance the obturator over the guidewire and into the right atrium. Continued advancement of the obturator, or the distal cone of the balloon catheter dilates the opening within the intra-atrial septum. Upon retraction of the obturator from the secondary incision site, the opening within the septum does not immediately recoil, but remains slightly stretched, which more easily receives the delivery sheath with the balloon catheter as described above or without the balloon catheter.

In yet another method of implanting the transseptal cannula assembly, the surgeon can include a balloon catheter in a manner different than was described previously. That is, the balloon catheter is inserted within the transseptal cannula assembly while the balloon is in a deflated position. Once the distal portion of the tip of the transseptal cannula assembly is within the left atrium and the delivery sheath is initially being retracted, the balloon catheter is simultaneously inflated. The combined acts of retracting the delivery sheath while inflating the balloon catheter will ensure proper and complete deployment of any of the anchors described herein.

After the transseptal cannula assembly has been implanted in accordance with one of the methods described previously, and all assistant devices (i.e. the guidewires, delivery device, balloon catheters, obturators, etc.) have been removed from the secondary incision site, the circulatory assist system can be implanted.

Figure 13:
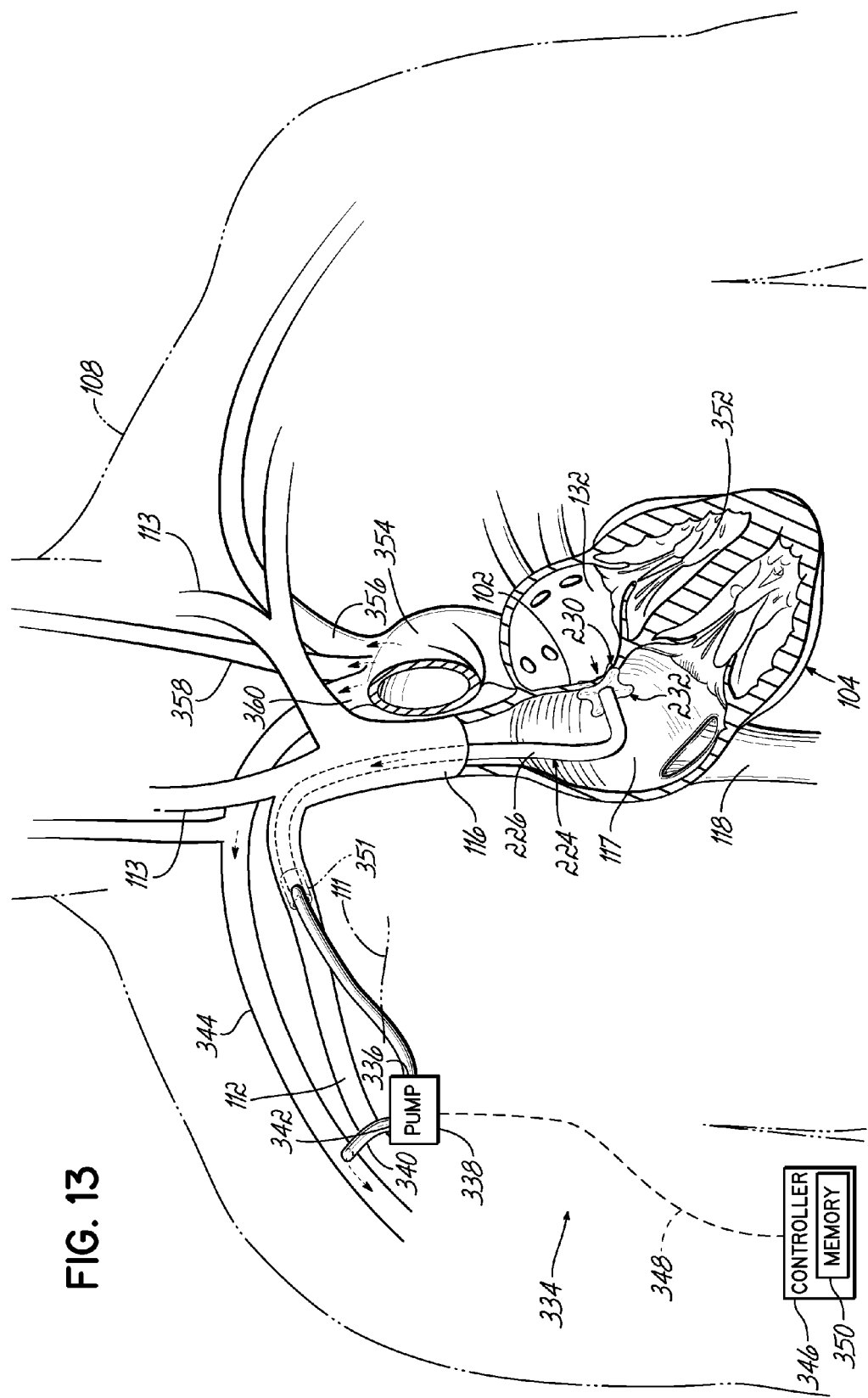
FIG. 13 is a diagrammatic view of an illustrative circulatory assist system positioned in the human heart shown in cross-section.

FIG. 13 illustrates the implanted circulatory assist system 334 in association with the transseptal cannula assembly 224. In that regard, the flexible cannula body 226, which generally extends from the intra-atrial septum 102 to the secondary incision site 111 (via the superior vena cava 116 and right subclavian vein 112), is cut to an appropriate length and attached to the input port 336 of the implantable pump 338. A separate outflow cannula 340 is attached to the output port 342 of the implantable pump 338, which is then surgically attached so as to communicate with a suitable superficial artery, such as the right subclavian artery 344. At this time, the surgeon may position the implantable pump 338 subcutaneously or submuscularly within the secondary incision site 111 or maintain the pump 338 externally even after the secondary incision site 111 is closed.

As also shown in FIG. 13, the pump 338 is operably associated with a controller 346, which may also be implanted or remain external to the patient 108. A signal transmission means 348 is provided between the pump 338 and the controller 346 and may be either a hard-wired or wireless communications device. In operation, the controller 346 may regulate the pumping action of pump 338. Additionally, a memory device 350 may be included within the controller 346 that will record pump activity for subsequent doctor evaluation and interaction.

Alternatively, as also shown in FIG. 13, when only the first anchor on the tip 228 is used, a hemostasis cuff 351 (shown in phantom) can act as the second anchor and can prevent distal movement of the transseptal cannula assembly 224. The hemostasis cuff 351 provides a seal around the transseptal cannula assembly 224 at the wall of the right subclavian vein 112. In construction, the hemostasis cuff 351 can be constructed of an elastic material, such as collagen, that will expand upon contact with a fluid, such as blood.

The completed flow of blood according to a preferred embodiment and as shown in FIG. 13 will be as follows: oxygenated blood will travel from the left atrium 132 via the natural path into the left ventricle 352 to the aorta 354. From the aorta 354, blood moves into the left subclavian artery 356, the left common carotid 358, and the brachiocephalic trunk 360. Oxygenated blood will also enter the transseptal cannula assembly 224 from the left atrium 132. Blood will enter the flexible cannula body 226 and travel through the lumen of the flexible cannula body 226 to the pump 338. The pump 338 actively pumps blood into the outflow cannula 340 and into the right subclavian artery 344. From here, the blood is directed into the remainder of the vascular network.

Figure 14:
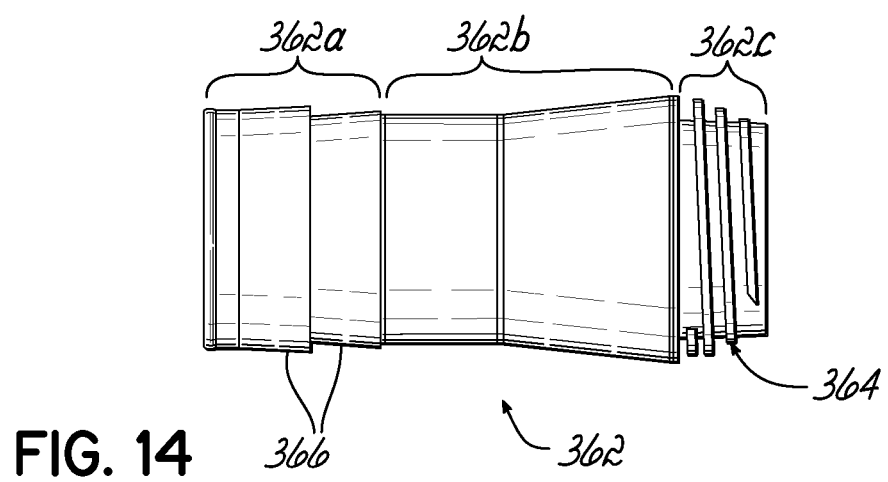
FIG. 14 is a side elevation view of another embodiment of the tip of the transseptal cannula assembly according to another embodiment.

In one alternate embodiment, illustrated in FIG. 14, a tip 362 having proximal, medial, and distal portions 362a-c, can include an anchor constructed to resemble screw threads 364 upon the distal portion 362c. In this way, the surgeon would rotate the tip 362 through the intra-atrial septum (not shown) such that successive screw threads 364 of the anchor will adjoin the walls of the septum. The proximal end 362a could include barbs 366 for attaching the flexible cannula body 226 (FIG. 6) of the transseptal cannula assembly 224 (FIG. 6). While this embodiment is illustrated in isolation, the tip 362 may be used with any of the deployable anchor embodiments described herein.

Figure 15:
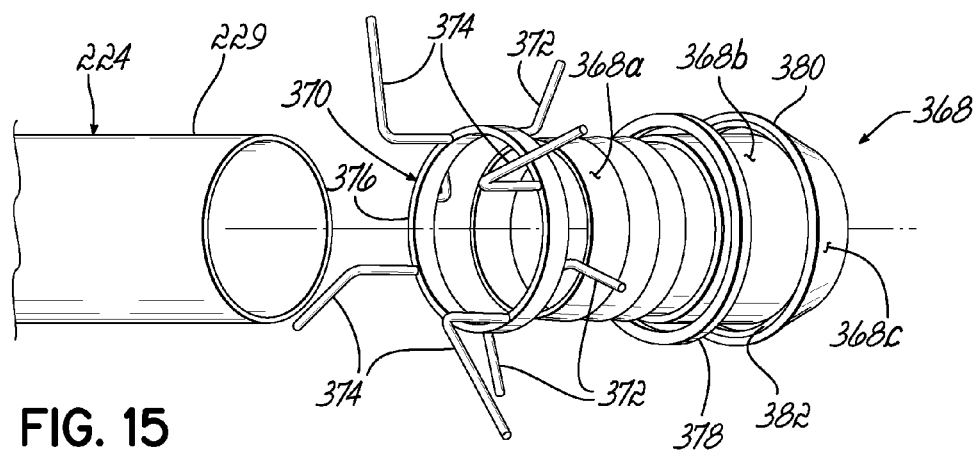
FIG. 15 is a disassembled perspective view of an alternate embodiment of the transseptal cannula assembly.
Figure 16A:
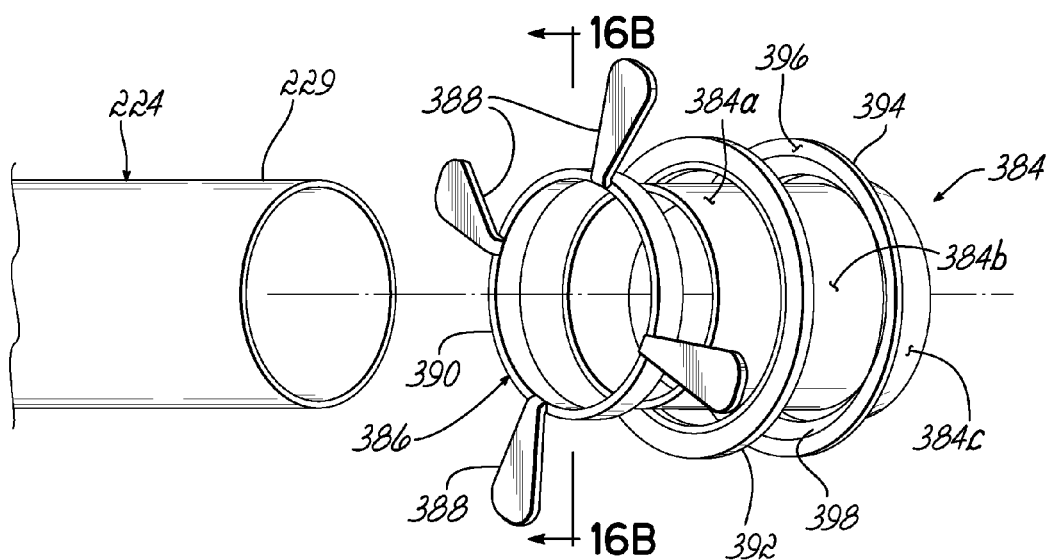
FIG. 16A is a disassembled perspective view of yet another alternative embodiment of the transseptal cannula assembly.
Figure 16B:
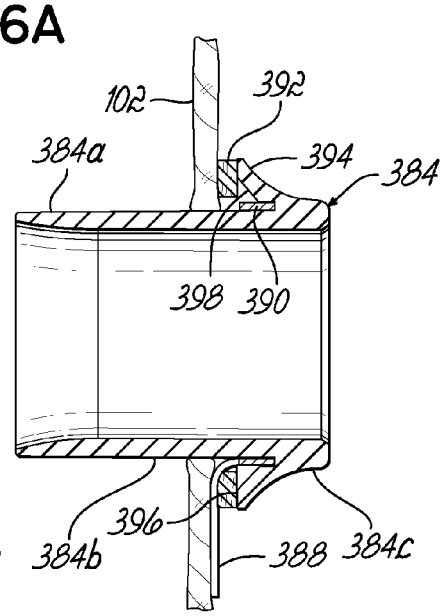
FIG. 16B is a longitudinal cross-section of the transseptal cannula assembly of FIG. 16A along the line 16B-16B.

FIGS. 15, 16A and 16B illustrate two versions of alternate embodiments of the tip and the anchors. Specifically, FIG. 15 illustrates a tip 368 with proximal, medial, and distal portions 386a-c having an anchor 370 formed upon the proximal end 368a and including first and second sets of struts 372, 374 extended from a single central portion 376. This single central portion 376 permits the struts 372, 374 of the anchor 370 to be constructed as a double-sided unit. In this alternative, the struts 374, which remain within the right atrium 117 (FIG. 12D), are constructed to be larger than the struts 372. The struts 372, 374 are slender and long to increase the surface contact area between the intra-atrial septum 102 (FIG. 12D)

and the struts 372, 374 without necessarily including a porous polymeric structure covering the struts 372, 374.

However, as shown in FIG. 15, when the benefit of the porous polymeric structure is desired but space is limited, it would be permissible to include a smaller ring of porous polymeric structure 378 with the tip 368. This ring of porous polymeric structure 378 can act in a manner described previously, i.e. a surface for tissue in-growth but without increasing the size of the anchor 370. The distal end 368c can be shaped to include a flared portion 380 to define a mounting groove 382 for receiving the ring of porous polymeric structure 378. Thus, in assembling the tip 368, the ring of porous polymeric structure 378 and single central portion 376 can be secured within the mounting groove 382 by pressing the components together. Alternatively, the tip 368, ring of porous polymeric structure 378, and the anchors 370 can be secured by welding or other suitable means.

Another embodiment as shown in FIGS. 16A and 16B, is a tip 384 having proximal, medial, and distal portions 384a-c, and includes a single-sided anchor 386 having a plurality of paddle-struts 388 extending from a central portion 390. The paddle-struts 388 are deployed within the left atrium (not shown). The plurality of paddle-struts 388 provides additional surface contact area between the intra-atrial septum 102 (FIG. 12D) and each of the plurality of paddle-struts 388. While not directly shown, it would be possible to construct a double-sided anchor, similar to that of FIG. 15, but with the plurality of paddle-struts 388. Accordingly, the shapes of the struts may vary according to a particular surgical need and need not be limited to those shown herein.

FIGS. 16A and 16B illustrate a ring of porous polymeric structure 392, similar to that described previously, but larger in surface area. In that regard, the distal end 384c of the tip 384 can include an enlarged flared portion 394 to create a surface 396 and mounting groove 398 for engaging the ring of porous polymeric structure 392 and the central portion 390 of the anchor 386. This enlarged flared portion 394 can provide even greater stability and support to the ring of porous polymeric structure 392. Additionally, it would also be permissible to adhere the ring of porous polymeric structure 392 to the surface 396 for even greater stability.

FIG. 16B further illustrates the portions of the ring of porous polymeric structure 392 between each of the plurality of paddle-struts 388 that will engage the intra-atrial septum 102.

In another alternate embodiment, as shown in FIG. 17, the flexible cannula body 400 can include first and second control wires 402, 404 upon the proximal end 406. The control wires 402, 404 allow the surgeon to maintain control of the position of the flexible cannula body 400 and thus the tip 228 (FIG. 6) within the patient's heart while the delivery sheath 210 (FIG. 6) is being removed from the secondary incision site. As shown, the first and second control wires 402, 404 can be constructed from stainless steel and can further be braided, as shown at 408, to increase strength and stability of the individual control wires 402, 404. The overall length of control wires 402, 404 could, for example, extend the total length of the flexible cannula body 400 to at least one and one-half times the length of the delivery sheath 210 (FIG. 6). This would ensure the surgeon's control over the position of the transseptal cannula assembly at any time during the surgical procedure.

A marker band 410, also shown in FIG. 17, can be positioned near the proximal end 406 of the flexible cannula body 400 so that the position of the flexible cannula body 400 can be monitored, in vivo. The marker band 410 can be constructed of radiopaque materials, similar to those described previously.

In other embodiments, at least a portion of the flexible cannula body 400 can include a coil 412 to reinforce the molded flexible cannula body 400. Materials suitable for the coil 412 may include high-elastic or superelastic metallics, including NiTi or spring tempered stainless steel wire.

In operation, as the surgeon retracts the delivery sheath, for deployment or complete retraction from the secondary incision site, the surgeon grasps the control wires 402, 404 of the flexible cannula body 400. In this way, the position of the tip, anchors and flexible cannula body 400 within the intra-atrial septum can be maintained while the delivery sheath is retracted.

In yet another embodiment, the delivery device can include a sheath constructed from a peel away material. In this way, after the transseptal cannula assembly has been properly inserted, the sheath is split and removed.

Finally, FIGS. 18A and 18B illustrate yet another embodiment (see also FIG. 4D) for aiding in the deployment of the anchors, the delivery sheath can be replaced with a truncated sheath 414, which is constructed to cover only the tip 228 (FIG. 6) and anchors (only the first anchor 230 is shown) and thus does not extend the entire length of the flexible cannula body 226. The truncated sheath 414 extends proximally by at least one control wire 416 to the secondary incision site 111 (FIG. 1A). In this way, the surgeon is able to move the truncated sheath 414 by pulling on the control wire 416 and thus deploying the anchors in a manner similar to that described previously. The particular benefit to this embodiment is that the surgeon can have greater control over maintaining the position of the transseptal cannula assembly 224 than was permitted with the previously described delivery sheaths. In essence, much of the length of the delivery sheath 210 has been replaced by one or more control wires 416, which more easily permits blood to continue flowing around the transseptal cannula assembly during the implanting surgical procedure.

Figure 19A:
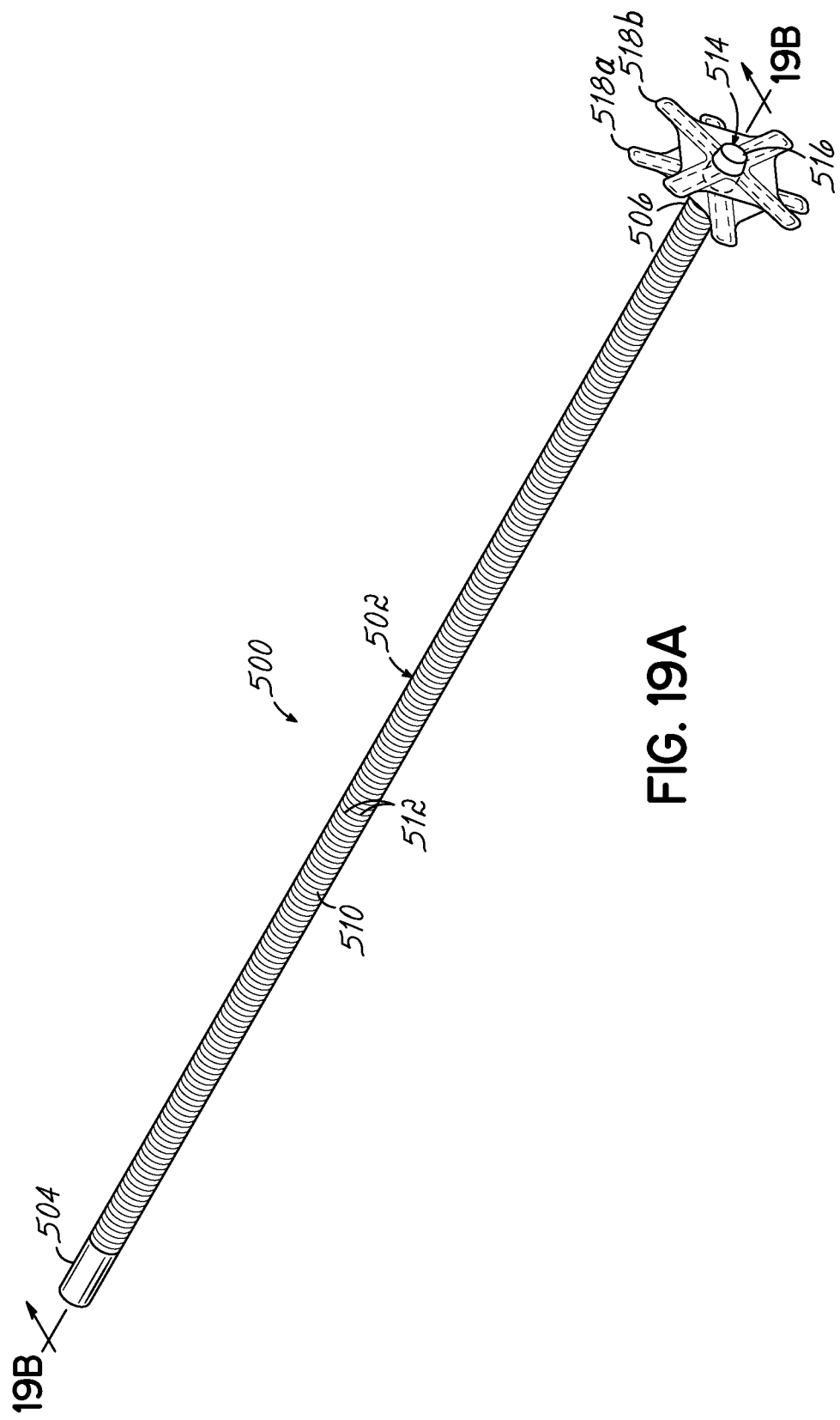
FIG. 19A is a perspective view of one embodiment of the cannula assembly.
Figure 19B:
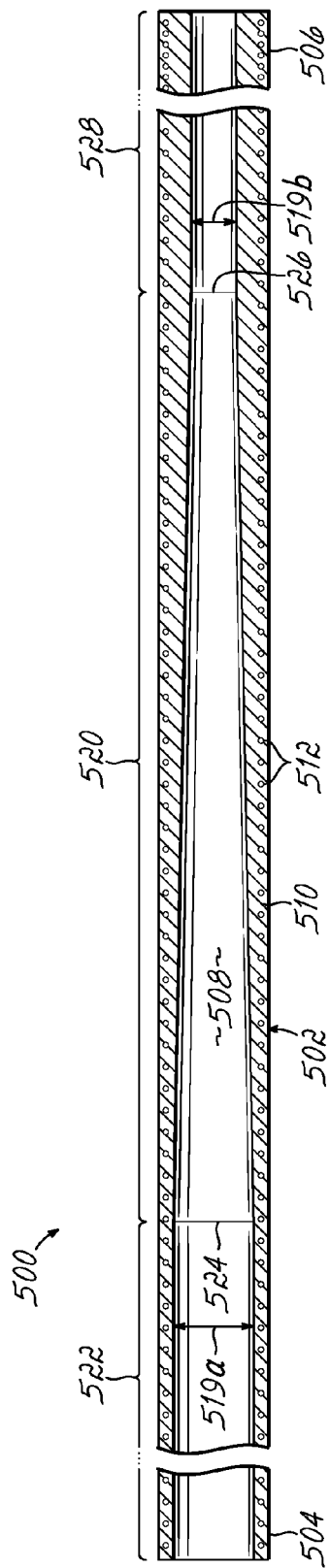
FIG. 19B is a longitudinal cross-sectional view of the cannula assembly of FIG. 19A.

With reference to FIG. 19A-19B, an alternative embodiment of a transseptal cannula assembly 500 of a circulatory assist system is shown. The transseptal cannula assembly 500 includes a cannula body 502 having a proximal end 504, a distal end 506, and a lumen 508 therebetween. The cannula body 502 may include a reinforced portion 510, as shown by coils 512 disposed along the length of the cannula body 502. In an alternative embodiment, instead of having a circular cross-section as shown in FIG. 19A, the coils 512 may have a substantially rectangular cross-section (not shown), thereby reducing the cross-sectional area of the coils 512. Such a configuration of coils 512 may advantageously provide for a reduction in the overall cross-sectional area of the cannula body 502.

A tip 514 is coupled to the distal end 506 of the cannula body 502 and includes an opening 516 communicating with the lumen 508 of the cannula body 502. More specifically, the tip 514 is coupled to the cannula body 502 by an interference fit. Barbs 538 (FIG. 22) may provide resistance against the undesired removal of the cannula body 502 from the tip 514. The tip 514 may also preferably include anchors 518a, 518b.

Figure 23A:
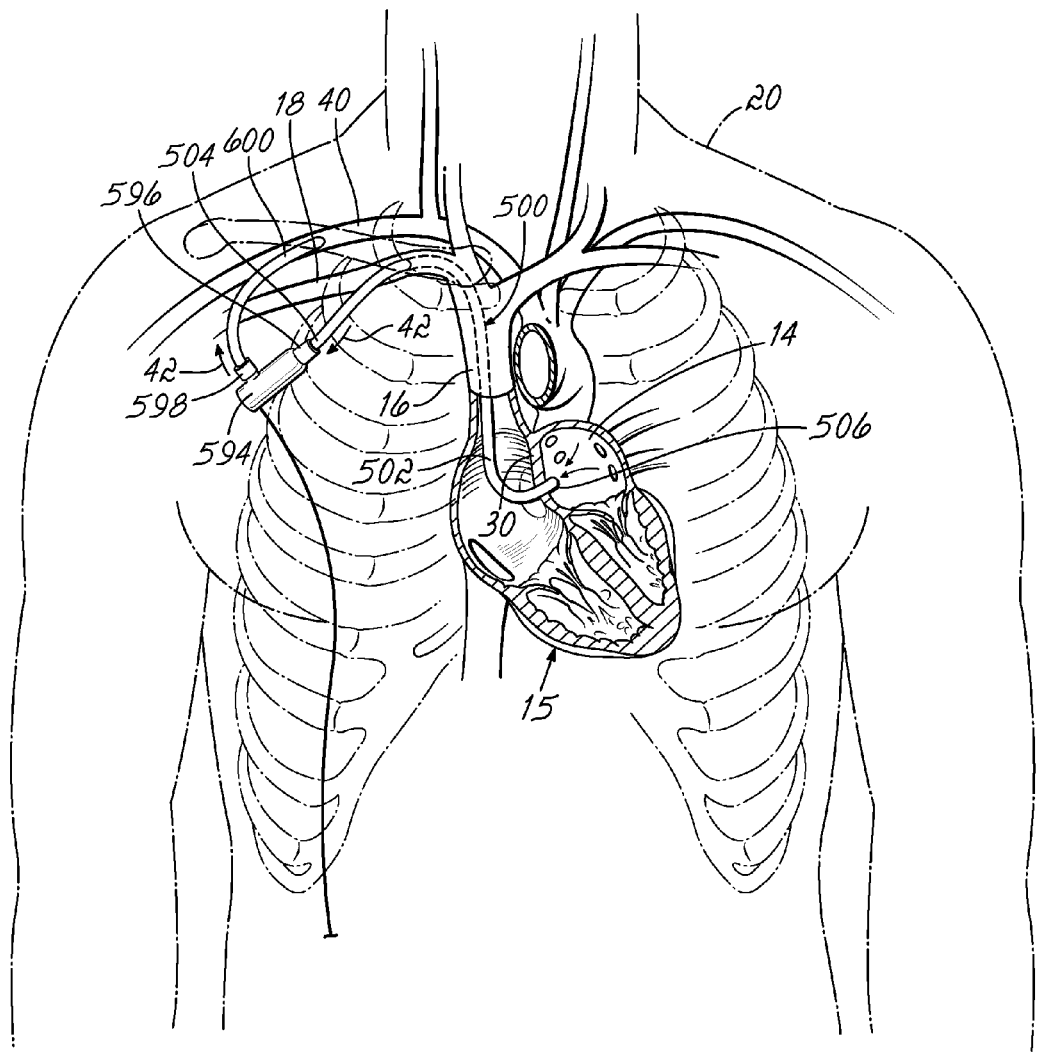
FIG. 23A is a diagrammatic view of an exemplary method of accessing the septum of the human heart, shown in cross-section.
Figure 23B:
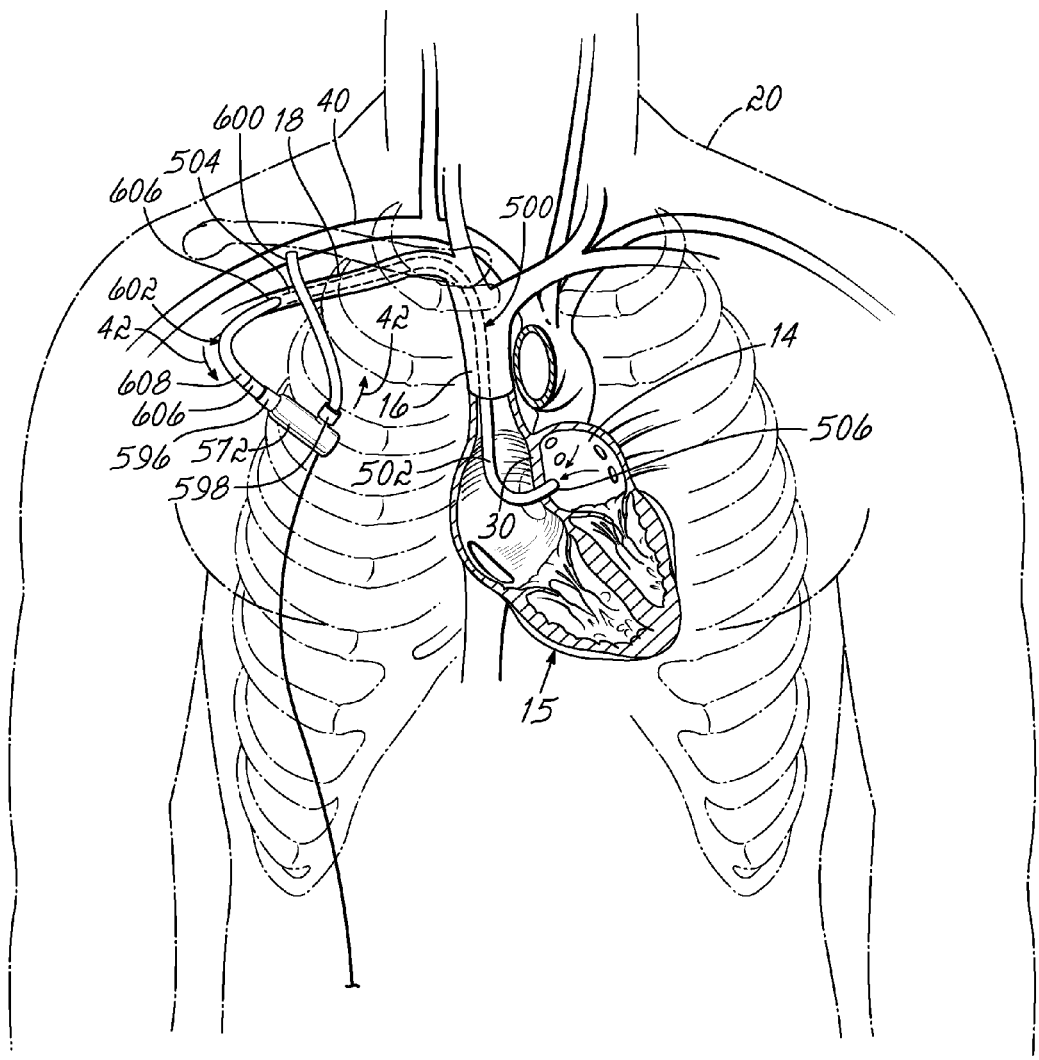
FIG. 23B is a diagrammatic view of an exemplary method of accessing the septum of the human heart, shown in cross-section, showing a cannula adaptor and alternative configuration of a blood pump.

The lumen 508 has a first inner diameter 519a at the proximal end 504 and a second inner diameter 519b at the distal end 506. The first inner diameter 519a is larger than the second inner diameter 519b, thereby defining a tapered portion 520 in the lumen 508. The tapered portion 520 is configured to prevent cavitation of the blood within the lumen 508 as the pressure of the blood decreases from the distal end 506 to the proximal end 504 of the cannula assembly 500, as the blood is drawn from a cavity of the heart 15 and directed into the circulatory system of a patient 14 (FIGS. 23A through 23B).

More specifically, the lumen 508 includes a first inner diameter 519a along a proximal portion 522 of the lumen 508. Along the proximal portion 522, the first inner diameter 519a remains constant. In one embodiment, the first inner diameter 519a along the proximal portion 522 is about 5.75 to 5.8 mm. The tapered portion 520 in the lumen 508 is defined as a stepped tapered portion such that at the beginning of the tapered portion 524, the inner diameter of lumen 508 is about 5.75 to 5.8 mm. At an end point 526 of tapered portion 524, the inner diameter of lumen 508 is about 5 mm. Then, continuing along the distal portion 528, the inner diameter of lumen 508 is about 5 mm until the distal end 506 of the cannula body 502. In a preferred embodiment, cannula body 502 and lumen 508 have a length of about 290 mm. In the lumen 508, proximal portion 522 has a length of about 190 mm, tapered portion 520 has a length of about 30 mm, and distal portion 528 has a length of about 70 mm. In this embodiment, providing a tapered portion 520 within the lumen 508 results in a 25% improvement in pressure loss as blood travels from the cavity of the heart at the distal end 506 of the cannula body 502 to the proximal end 504, where the cannula body 502 communicates with the circulatory system of a patient.

In an alternative embodiment, the lumen 508 may be provided with an alternatively configured tapered portion 520. Instead of having a stepped tapered portion as discussed with respect to FIG. 19A-19B, the tapered portion 520 could be defined as a constant taper between the first inner diameter 519a of the proximal end 504 and the second inner diameter 519b of the distal end 506. Further alternatively, the lumen 508 may include more than one stepped tapered portion between the proximal and distal ends 504, 506 configured to reduce pressure loss and prevent cavitation of blood traveling from the distal end 506 to the proximal end 504. Moreover, these dimensions disclosed above are specific to the embodiment described above and are not meant to limit the disclosure herein.

Figure 20:
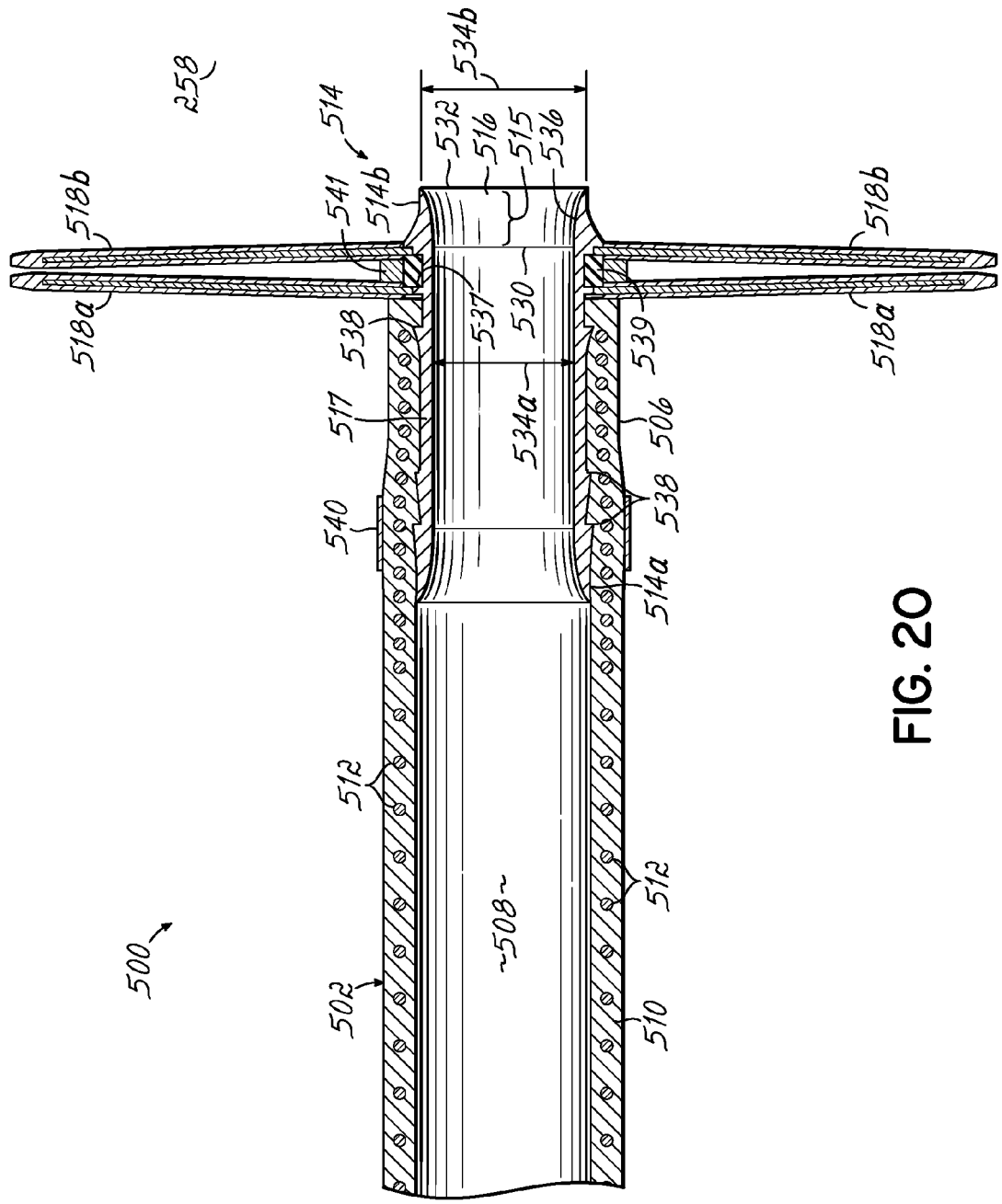
FIG. 20 is a detailed cross-sectional view of the cannula assembly of FIG. 19A.

With reference to FIG. 20, it may be advantageous to provide the tip 514 of the cannula assembly 500 with characteristics that improve blood flow characteristics of the cannula assembly 500. Tip 514 includes a proximal end 514a, a distal end 514b, and a body 517 therebetween. As shown in FIG. 20, distal portion 515 of tip 514 includes first and second ends 530, 532 having first and second inner diameters 534a, 534b, respectively. The second end 532 is more distal than the first end 530 and the second inner diameter 534b is larger than the first inner diameter 534a. In one embodiment of the tip 514, the difference in the first and second inner diameters 534a, 534b defines at least a portion of the tip 514 as a generally campanulate, or bell-shaped, member. More specifically, the tip 514 includes a first end 530 with a first inner diameter 534a and a second end 532 with a second inner diameter 534b. In between the first and second ends 530, 532 is a generally curvilinear portion 536, thereby defining at least a portion of the tip 514 as a generally campanulate shape.

The campanulate shape of the tip 514 provides fluid flow benefits for the circulatory assist system. More specifically, the campanulate shape provides a smoother flow transition, and thus lower pressure losses, as a fluid is moving from the larger heart chamber, into the smaller tip 514 and cannula body 517. Reducing pressure losses of the fluid or blood entering the tip 514 provides for a more advantageous circulatory assist system. Furthermore, advantageously, the campanulate shape reduces the occurrence of turbulence of blood at the tip 514 and in the cannula 502 when blood is drawn into the lumen 508, thereby increasing the overall efficiency and efficacy of the system.

The generally campanulate tip 514 may be free of imperfections that may cause thrombus formation. For example, the tip 514 may be polished in order to remove any imperfections that may lead to thrombus formation. Moreover, the transition between the cannula body 502 and the tip 514 may be smooth and free of irregularities that may cause thrombus.

With further reference to FIG. 20, the tip 514 may further include one or more barbs 538 on the proximal end 514a of the tip 514. Barbs 538 provide resistance against the undesired removal of the cannula body 502 from the tip 514. In addition to barbs, a swaged or crimped band 540 may be provided on the cannula body 502 to provide further resistance against the undesired removal of the cannula body 502 from the tip 514. The swaged or crimped band 540 may be comprised of a malleable material, such as tantalum, to accommodate for large fluctuations in size of the cannula body 502. Advantageously, if desired, the swaged or crimped band 540 may be used as a fluoroscopic visualization marker if constructed from a radiopaque material, such as tantalum.

Continuing with FIG. 20, the tip 514 can further include one or more rings 539, provided for potentially several reasons. For example, these rings 539 may act in a manner as to engage the anchors 518a, 518b. Advantageously, the rings 539 may be provided with a porous polymer structure 541 such as polyester fabric wherein tissue from the septum may grow and embed within the porous polymeric structure 541 to provide greater structural stability. The distal end 506 of cannula body 502 may essentially abut one of the anchors 518. Further, additional rings 537 may be included and could be used to seat the anchors 518a, 518b and can be keyed in a way so as to maintain an orientation of the anchors 518a, 518b.

FIG. 21A shows an alternative embodiment of a delivery sheath 542. The delivery sheath 542 further comprises a distal end 544, a proximal end 546, and a body 548 therebetween. The delivery sheath 542 includes a hub 543 at the proximal end 546 operably connected to tubing 545 connectable to an air source or for venting the hub 543 or delivery sheath 542. Due to the material characteristics of the delivery sheath 542, the delivery sheath 542 tends to deform in the direction of movement of the cannula assembly 500 as the cannula assembly 500 moves relative to the delivery sheath 542 during delivery of the cannula assembly 500 to the septum. The plastic deformation of the sheath 542 is disadvantageous when advancing the cannula anchors 518 out of the tip 514 because the delivery sheath 542 may stretch as the proximal anchors 518a exit, then subsequently recoil in an uncontrolled manner. The sheath behaving in such a manner may inadvertently deploy the distal anchors 518b in the left atrium. The tensile element 550 is used to prevent this and therefore gives the physician precise control of the sheath tip 514 when deploying each anchor 518a, 518b.

As shown in FIG. 21A, the delivery sheath 542 includes a longitudinally disposed tensile element 550. The tensile element 550 prevents the stretching and subsequent recoil as described above, and therefore gives the physician precise control of the sheath tip 514 when deploying each set of anchors 518a, 518b. In an alternative embodiment, however, the delivery sheath 542 could have more tensile elements 550. For example, the body 548 of the delivery sheath 542 could have at least two or more tensile elements 550, preferably equally spaced apart. The tensile element may be flexible such that it does not compromise the bending characteristics of the sheath 542. The tensile element 550 may therefore comprise a material which is configured to provide the desired bending characteristics of the sheath 542. Preferably, the tensile element 550 comprises a monofilament or polyfilament of a polymeric material. More specifically, the tensile element may comprise a polyfilament which may comprise wound or braided polymeric material. The tensile element 550 may be embedded in the body 548 of the delivery sheath 542 such that the tensile element 550 is disposed between inner and outer walls (not shown) of the body. The tensile element 550 may be embedded in the body 548 in such a manner by a variety of manufacturing methods. In one embodiment, the tensile element is held in tension using slots in each end of a mandrel while the sheath 542. A reflow process, using Fluorinated ethylene propylene (FEP) as a compression material allows the elements to be encapsulated between the inner body and coils 555, and the outer body when heated above the melt temperature of the material of the inner and outer portions of the body.

Alternatively, other modes of manufacture are possible and will be apparent to persons skilled in the art. In addition to the tensile element 550, the delivery sheath 542 may include reinforcement structures, such as coils 555 to prevent collapse of the delivery sheath 542 during use thereof.

Figure 21C:
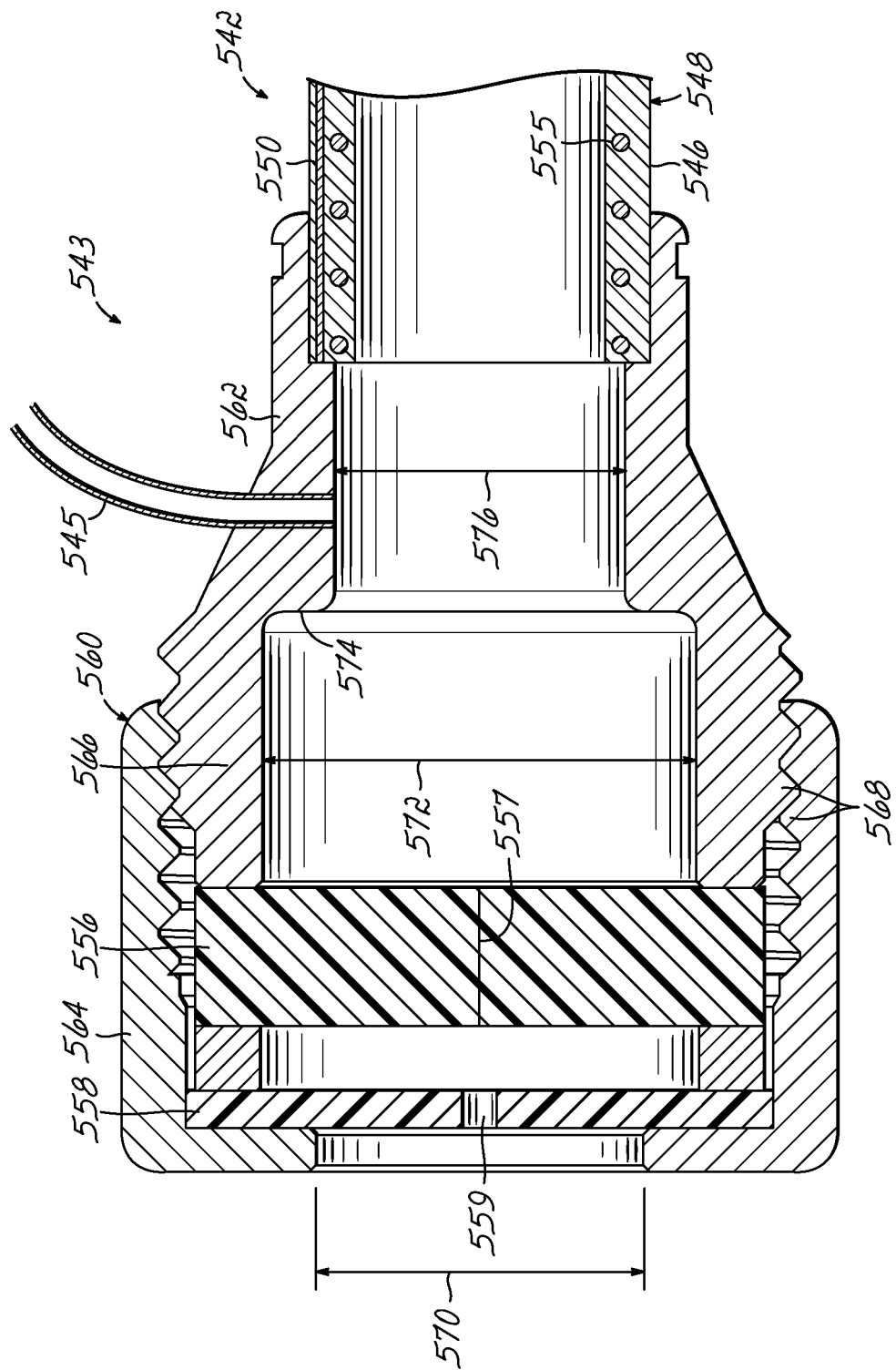
FIG. 21C is a detailed cross-sectional view of the hub of the delivery sheath of FIG. 21A.

FIG. 21C shows an embodiment of a hub 543 of the delivery sheath 542. The hub 543 includes a distal, primary seal 556 having a slit 557 and a proximal secondary seal 558 having an aperture 559. The multiple seals are provided in order to allow for a hemostatic seal where devices of varying sizes are directed into the hub 543 and delivery sheath 542. In one embodiment, the proximal seal has a width 0.050", while the distal seal has a width of 0.25". The multi-stage seal is adapted to provide a hemostatic seal for a guidewire, which may have an outer diameter of 0.035", up to a cannula body, which may have an outer diameter up to 0.5", and possible even greater than 0.5". The tubing 545 is distal of the primary and secondary seals 556, 558 at a point distal of the step 574. The placement of the tubing 545 distal of the seals 556, 558 allows the hub 543 to maintain a hemostatic seal in the system while venting the delivery sheath 548. Tubing 545 may also be utilized for directing fluids into the system.

In one embodiment, the hub 543 comprises a multi-part assembly 560 having a distal portion 562 and a proximal portion 564. The distal portion 562 includes the primary seal 556 and is fixedly coupled to the delivery sheath 542. The distal portion 562 includes a section 566 configured to receive the proximal portion 564 and maintain the position of the proximal portion 564 relative thereto. In one embodiment, the distal portion 562 and proximal portion 564 include threaded portions 568, which threadably engage to thereby couple the distal and proximal portions 562, 564 together and maintain the position of the proximal portion 564 relative to the distal portion 562.

The hub 543 includes a first inner diameter 570 at the proximal portion 564 sized to receive a loading device 578 (FIG. 22A). The distal portion 562 of the hub 543 includes a second inner diameter 572 which is sized to receive the loading device 578. The distal portion 562 of the hub 543 includes a step 574 which is defined as a transition between the second inner diameter 572 and a third inner diameter 576 of the hub. The third inner diameter 576 is the same or similar to the inner diameter 586 (FIG. 22A) of the loading device 578 such that the anchors 518a, 518b remain folded when exiting from the loading device 578 and while being directed into the distal portion 562 of the hub 543.

FIG. 22A shows an alternative configuration of a loading device 578 of the delivery system as discussed herein. In the embodiment as shown in FIG. 22A, the loading device 578 is configured to receive the anchors 518a, 518b in the contracted state and assist the delivery of the cannula assembly 500 into the delivery sheath 542 with the anchors 518a, 518b in the contracted state.

The loading device 578 includes a distal end 580, a proximal end 582 and a lumen 584 therebetween. The distal end 580 has a first inner diameter 586 and the proximal end 582 has a second inner diameter 588. The first inner diameter 586 is smaller than the second inner diameter 588, thereby defining inner and outer stepped portions 590a, 590b in the lumen 584 and on the outer portion 591, respectively, between the distal and proximal ends 580, 582 of the lumen 584. The inner stepped portion 590a includes a taper 592 configured to prevent damage to the anchor 518 when the loading device 578 receives the anchors 518 in the contracted state.

Figure 22E:
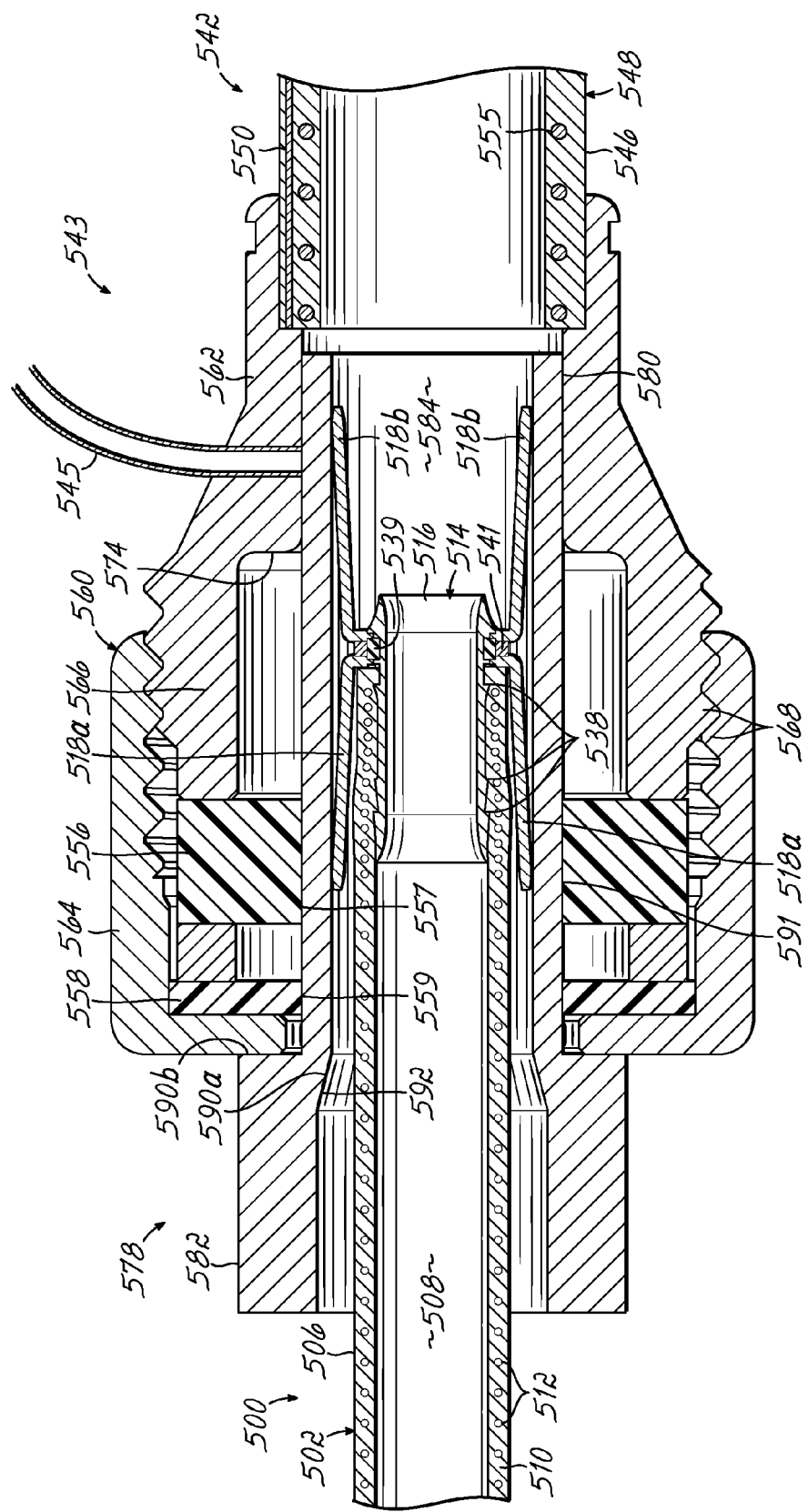
FIG. 22E is a detailed cross-sectional view showing the loading device with the cannula assembly as shown in FIG. 22D as directed into the hub of FIG. 21C.

The loading device 578 is used to fold the anchors 518a, 518b and introduce the cannula assembly 500 into the hub 543 of the delivery sheath 542. To fold the anchors 518a, 518b, the cannula tip 514 is advanced into and through the loading device 578 as shown in the FIG. 22B, thereby folding both sets of anchors 518a, 518b in the proximal direction. As shown in FIG. 22C, the distal anchors 518b are allowed to exit the distal end 580 of the loading device 578 until they extend. The cannula assembly 500 is then retracted slightly in the proximal direction to fold the distal anchors 518b distally and leaving the proximal anchors 518a folded proximally. The loading device 578 is then inserted into the sheath hub 543 (FIG. 22E) through primary and secondary seals 557, 558 and remains engaged with the hub 543 until the tip 514 of the cannula assembly 500 traverses past the distal, primary seal 557. The loading device 578 is removed and the seals 557, 558 provide a hemostatic seal on the cannula body 502. The inner diameter of the delivery sheath 542 may be the same or substantially similar as the inner diameter 586 of the loading device 578 to ensure a smooth transition when advancing the cannula tip 514 out of the loading device and into the sheath 542.

The loading of the cannula assembly 500 to move the anchors 518a, 518b into a folded configuration may be completed without the aid of fluoroscopy. Once the cannula assembly 500 resides within the sheath 542, fluoroscopy may be used to aid the delivery of the cannula assembly 500 to the septum 30. The taper 592 in the loading device 578 prevents damage, such as tearing, of the anchors 518a, 518b as the anchors 518a, 518b are directed into the loading device 578. The taper 592 further prevents tearing of the anchors 518a, 518b as the loading device 578 is retracted from the hub 543 of the delivery sheath 542 and as the cannula assembly 500, with the anchors 518 in a contracted state, is directed further into the delivery sheath 542.

FIG. 23A shows a typical configuration of a circulatory assist system, including a cannula assembly 500 for directing blood from the heart of a patient. More specifically, the distal end 506 of the cannula body 502 is in fluid communication with the right atrium 14 of the heart 15. The cannula body 502 traverses therefrom through the septum 30, up through the superior vena cava 16 and into the subclavian vein 18. At a point in the subclavian vein 18, the cannula body 502 exits therefrom and the proximal end 504 of the cannula body 502 is fluidicly communicated with an inlet portion 596 of a pump 594. The outlet 598 of the pump 594 is in fluid communication with an outflow cannula 600. The outflow cannula 600 communicates with the subclavian artery 40, into which blood is directed from the outflow cannula 600 as the outflow cannula 600 receives blood from the pump 594. In the configuration shown in FIG. 23B, the outflow cannula 600 is positioned over, or posterior to, the subclavian vein. However, depending on the anatomy of a specific patient, the outflow cannula 600 may be placed behind, or anterior to, the subclavian vein 18. In this configuration, the pump 594 is disposed such that the inlet portion 596 is facing a generally medial direction, or towards the center of the body of the patient 20. Blood flows in the direction of arrows 42.

FIG. 23B shows the configuration of a circulatory assist system which includes a cannula adaptor 602. Similar to the configuration as shown in FIG. 23A, the distal end 506 of the cannula body 502 is in fluid communication with the right atrium 14 of the heart 15. The cannula body 502 traverses therefrom through the septum 30, up through the superior vena cava 16 and into the subclavian vein 18. However, at a point in the subclavian vein 18, the cannula body 502 exits and, instead of being coupled directly with the inlet portion 596, the proximal end 504 of the cannula body 502 is coupled to the distal end 604 of the cannula adaptor 602. The proximal end 606 of the cannula adaptor 602 then couples with the inlet portion 596 of the pump 594. In this configuration utilizing the cannula adaptor 602, the inlet portion 596 of the pump 594 is facing in a generally lateral direction, or facing generally away from the center of the body of the patient 20. The outlet 598 of the pump 594 fluidicly communicates with an outflow cannula 600. The outflow cannula 600 then fluidicly communicates with the subclavian artery 40. Blood flows in the direction of arrows 42.

The cannula adaptor 602 is provided for multiple potential advantageous reasons. The cannula adaptor 602 reduces stress on the subclavian vein 18. Rather than bending the cannula body 502 to reach the inlet 596 of the pump 594 and thereby stressing the vein 18 at the point where the cannula body 502 exits therefrom, the cannula adaptor 602 is provided with an essentially curvilinear shape to reach the inlet 596 of the pump 594.

Figure 23C:
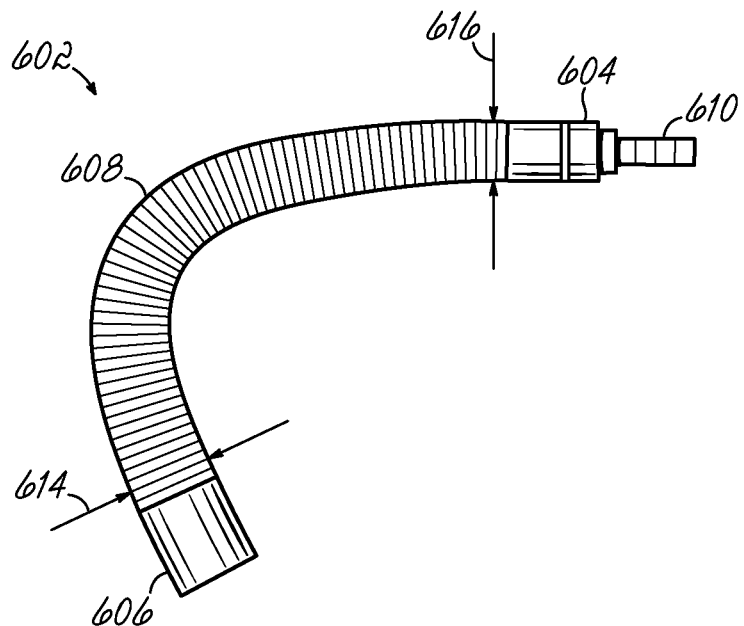
FIG. 23C is a detailed side view of the cannula adaptor shown in FIG. 23B.
Figure 23D:
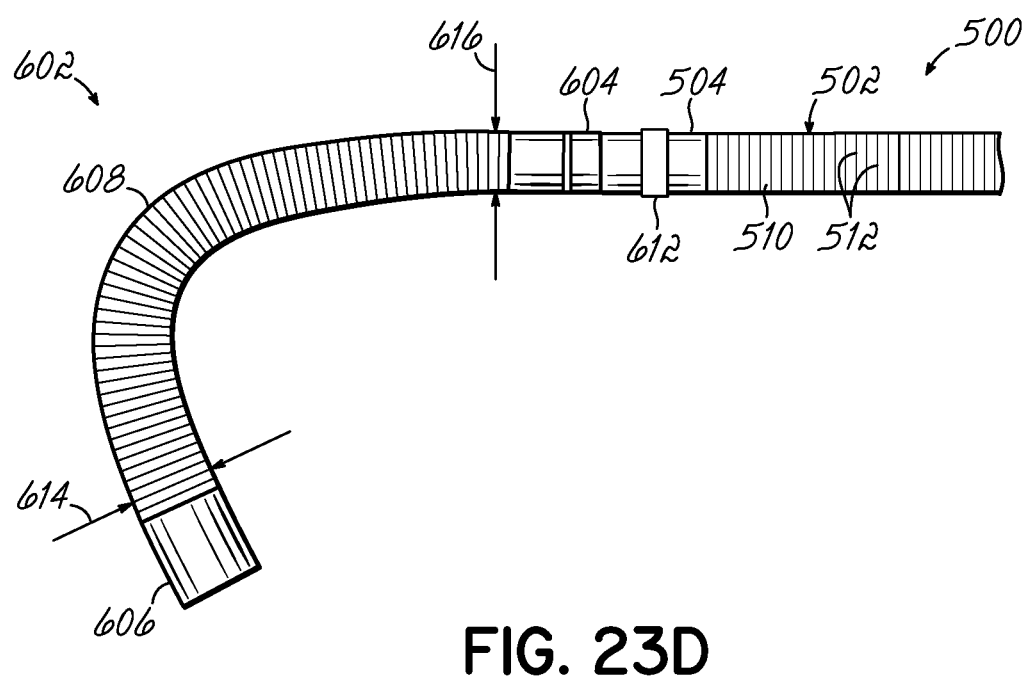
FIG. 23D is a side view of the cannula adaptor of FIG. 23B coupled with the cannula body.

As shown more specifically in FIGS. 23C-23D, the cannula adaptor 602 further comprises a distal end 604, a proximal end 606 and a body 608 therebetween. The distal end 604 of the cannula adaptor 602 couples with the proximal end 504 of the cannula body 502. To facilitate the connection, the distal end 604 of the adaptor device 602 further comprises a fitting 610 adapted to receive the proximal end 504 of the cannula body 502. Furthermore, a swaged or crimped band 612 may be provided on the cannula adaptor 602 to provide further resistance against the undesired removal of the cannula body 502 from the fitting 610 of the cannula adaptor 602. The proximal end 606 of the adaptor device 602 couples with the inlet 574 of the pump 594. In one embodiment, the proximal and distal ends 606, 604 of the cannula adaptor 602 may connect to the pump 594 and the cannula body 502, respectively, using connections not requiring additional fasteners or sutures therebetween. For example, the proximal end 606 of the cannula adaptor 602 may connect to the pump inlet 596 in a snapping or ratcheting fashion.

The cannula adaptor 602 comprises a generally curvilinear shape, which enables the configuration as shown in FIG. 23B. For advantageous fluid flow, the body 608 includes a taper between the proximal and distal ends 606, 604, where the taper is defined as a decrease in diameter from the first diameter 614 to the second diameter 616 between the proximal and distal ends 606, 604. More specifically, the tapered configuration of the body, and thus the lumen therein (not shown) is provided to prevent cavitation in the pump 594 as the pressure decreases along the length of the cannula adaptor 602. In one embodiment, the decrease in diameter is constant along the tapered portion.

Further, advantageously, the tapered configuration of the cannula adaptor 602 further allows for a relatively smaller cannula body 502 to be used during a procedure, while still utilizing existing and/or currently utilized pumps 594. The proximal end 504 of the cannula body 502 is therefore preferably sized to couple to a blood pump known in the art, such as the CircuLite SYNERGY™ Pump. Therefore, because a smaller size cannula body 502 is able to be used, the cannula adaptor 602 enables use of the transseptal device and method described herein with a wider variety of procedures and patients. Utilizing a smaller size cannula body 502, for example, may lessen the constraints of the delivery thereof through the venous system.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A circulatory assist system, comprising:
 a cannula assembly having distal and proximal ends and a lumen therebetween;
 a pump for drawing blood into the cannula assembly and dispensing the blood from the cannula assembly and into the patient circulatory system; and
 a delivery sheath for delivering the cannula assembly through the patient circulatory system, wherein the delivery sheath is configured to receive the cannula assembly and move relative thereto for deploying the cannula assembly adjacent a heart cavity and further comprises a distal end, a proximal end, and a body therebetween; and
 a tensile element carried and extending along a length of the body, the tensile element configured to prevent deformation of the body when the cannula assembly moves relative to the delivery sheath.

2. The delivery system of claim 1, wherein the tensile element is configured to prevent plastic deformation of the delivery sheath in a substantially axial direction.

3. The delivery system of claim 1, wherein the delivery sheath further comprises an inner wall defining a passage for receiving the cannula assembly, and an outer wall, and the tensile element is disposed between the inner and outer walls of the delivery sheath.

4. The delivery system of claim 1, wherein the tensile element comprises at least one of the following: a monofilament or polyfilament.

5. The delivery system of claim 4, wherein the tensile element further comprises at least one of the following: metal, fabric, or polymer.

6. A circulatory assist system for assisting the flow of blood through a patient circulatory system, comprising:
 a cannula assembly for directing blood from the heart of a patient, the cannula assembly comprising a flexible cannula body including a proximal end and a distal end and a lumen therebetween;
 a pump for drawing blood from the heart into the cannula assembly and dispensing the blood from the cannula assembly and into the patient circulatory system, the pump further including an inlet and an outlet;

an outflow cannula configured to provide fluid communication between the outlet and the cardiovascular system of a patient; and an adaptor device configured to fluidicly communicate the inlet and the cannula body, the adaptor device including a proximal end, a distal end, and a lumen therebetween;

wherein the distal end of the adaptor device is configured to couple with the proximal end of the cannula body and the proximal end of the adaptor device is configured to couple with the inlet of the pump;

wherein the adaptor device is configured such that blood flowing into the distal end of the adaptor device flows in a generally lateral direction relative to the patient and blood flowing out of the proximal end of the adaptor device and into the inlet flows in a generally medial direction relative to the patient.

7. The circulatory assist system of claim 6, wherein the lumen of the adaptor device includes a tapered portion between the proximal and distal ends, the tapered portion defined as a decrease in inner diameter from a first inner diameter to a second inner diameter between the proximal and distal ends, respectively.

8. The circulatory assist system of claim 7, wherein the decrease in inner diameter is constant along the tapered portion.

9. The circulatory assist system of claim 6, wherein the distal end of the adaptor device further comprises a fitting adapted to receive the proximal end of the cannula assembly.

10. A method of deploying a circulatory assist system into a circulatory system of a patient, the circulatory assist system including a cannula assembly and a pump, the assist system for assisting the flow of blood through the circulatory system, comprising:

directing a cannula assembly into the circulatory system of a patient, wherein a distal end of the cannula assembly extends into a chamber of the heart, and the proximal end of the cannula assembly extends in a generally lateral direction therefrom;

implanting a pump having an inlet and an outlet such that the inlet faces in a generally lateral direction relative to the patient;

fluidicly communicating the outlet of the pump with the circulatory system using an outflow cannula;

coupling a proximal end of the cannula assembly with a distal portion of an adaptor device;

coupling a proximal portion of the adaptor device with the inlet of the pump;

wherein the adaptor device is configured such that blood flowing into the distal end of the adaptor device flows in a generally lateral direction relative to the patient, and blood flowing out of the proximal end of the adaptor device and into the inlet flows in a generally medial direction relative to the patient.

11. The method of claim 10, wherein the circulatory system is an artery.

12. The method of claim 11, wherein the artery is a subclavian artery.

* * * * *